United States Patent [19]
Brooks et al.

[11] Patent Number: 5,459,150
[45] Date of Patent: Oct. 17, 1995

[54] INDOLE DERIVATIVES WHICH INHIBIT LEUKOTRIENE BIOSYNTHESIS

[75] Inventors: Dee W. Brooks, Libertyville; George W. Carter, Mundelein; Joseph F. Dellaria, Lindenhurst, all of Ill.; Robert G. Maki, Kenosha, Wis.; Karen E. Rodriques, Stow, Mass.

[73] Assignee: Abbott Laboratories, Abbott Park, Ill.

[21] Appl. No.: 969,294

[22] PCT Filed: Aug. 7, 1991

[86] PCT No.: PCT/US91/05621

§ 371 Date: Feb. 16, 1993

§ 102(e) Date: Feb. 16, 1993

[87] PCT Pub. No.: WO92/03132

PCT Pub. Date: Mar. 5, 1992

Related U.S. Application Data

[63] Continuation-in-part of Ser. No. 570,248, Aug. 20, 1990, Pat. No. 5,095,031.

[51] Int. Cl.$^6$ .................... C07D 401/12; A61k 31/475
[52] U.S. Cl. ............... 514/314; 546/176; 546/174
[58] Field of Search .................. 546/176, 174; 514/314

[56] References Cited

U.S. PATENT DOCUMENTS

| | | | |
|---|---|---|---|
| 3,859,305 | 1/1975 | Posselt et al. | 260/326.15 |
| 3,931,229 | 1/1976 | Zinnes et al. | 260/326.12 R |
| 4,021,448 | 5/1977 | Bell | 260/326.13 D |
| 4,119,638 | 10/1978 | Ray | 260/326.12 A |
| 4,464,379 | 8/1984 | Betzing et al. | 424/263 |
| 4,918,094 | 4/1990 | Bernstein et al. | 514/419 |
| 4,992,464 | 2/1991 | Brooks et al. | 514/443 |
| 5,179,703 | 9/1992 | Lou et al. | 546/174 |

FOREIGN PATENT DOCUMENTS 0275667  7/1988  European Pat. Off. .

OTHER PUBLICATIONS

S. Rauscher, et al., J. Am. Chem Soc. 103 (9):2419–2412 (1981).

Kobayashi, et al., Yakugaku Zasshi, 91(II): 1164–1173 (1971 in Japanese).

*Primary Examiner*—David B. Springer
*Attorney, Agent, or Firm*—Jerry F. Janssen

[57] ABSTRACT

Substituted indolyl compounds of the formula

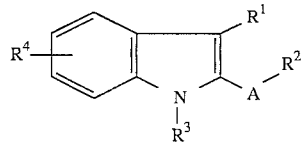

are potent inhibitors of the lipoxygenase enzymes and are useful as agents for the treatment of allergies and inflammatory disease states.

5 Claims, No Drawings

INDOLE DERIVATIVES WHICH INHIBIT LEUKOTRIENE BIOSYNTHESIS

CROSS-REFERENCE TO RELATED APPLICATIONS

This application is a continuation-in-part of application Ser. No. 570,248 filed Aug. 20, 1990, now U.S. Pat. No. 5,095,031.

TECHNICAL FIELD

This invention relates to compounds having pharmacological activity, to pharmaceutical compositions containing such compounds and to medical methods of treatment. More particularly, the present invention concerns certain substituted indole urea, oxime, acetamide and hydroxamic acid compounds, pharmaceutical compositions containing the compounds, and to a method of treating disease states which involve leukotrienes and other metabolic products resulting from the action of 5-lipoxygenase on arachidonic acid.

BACKGROUND OF THE INVENTION

5-Lipoxygenase is the first dedicated enzyme in the pathway leading to the biosynthesis of leukotrienes. This important enzyme has a rather restricted distribution, being found predominantly in leukocytes and mast cells of most mammals. Normally 5-lipoxygenase is present in the cell in an inactive form; however, when leukocytes respond to external stimuli, intracellular 5-lipoxygenase can be rapidly activated. This enzyme catalyzes the addition of molecular oxygen to fatty acids with cis,cis-1,4-pentadiene structures, converting them to 1-hydroperoxy-trans,cis-2,4-pentadienes. Arachidonic acid, the 5-lipoxygenase substrate which leads to leukotriene products, is found in very low concentrations in mammalian cells and must first be hydrolyzed from membrane phospholipids through the actions of phospholipases in response to extracellular stimuli. The initial product of 5-lipoxygenase action on arachidonate is 5-hydroperoxyeicosatetraenoic acid (5-HPETE) which can be reduced to hydroxyeicosatetraenoic acid (5-HETE) or converted to leukotriene $A_4$ ($LTA_4$). This reactive leukotriene intermediate is enzymatically hydrated to leukotriene $B_4$ ($LTB_4$) or conjugated to the tripeptide, glutathione, to produce leukotriene $C_4$ ($LTC_4$). $LTA_4$ can also be hydrolyzed nonenzymatically to form two isomers of $LTB_4$. Successive proteolyfic cleavage steps convert $LTC_4$ to leukotrienes $D_4$ and $E_4$ ($LTD_4$ and $LTF_4$). Other products resulting from further oxygenation steps have also been described in the literature. Products of the 5-lipoxygenase cascade are extremely potent substances which produce a wide variety of biological effects, often in the nanomolar to picomolar concentration range.

The remarkable potencies and diversity of actions of products of the 5-lipoxygenase pathway have led to the suggestion that they play important roles in a variety of diseases. Alterations in leukotriene metabolism have been demonstrated in a number of disease states including asthma, allergic rhinitis, rheumatoid arthritis, gout, psoriasis, adult respiratory distress syndrome, inflammatory bowel disease, endotoxin shock syndrome, atherosclerosis, ischemia induced myocardial injury, and central nervous system pathology resulting from the formation of leukotrienes following stroke or subarachnoid hemorrhage.

The enzyme 5-lipoxyganase catalyzes the first step leading to the biosynthesis of all the leukotrienes and therefore inhibition of this enzyme provides an approach to limit the effects of all the products of this pathway. Compounds which inhibit 5-lipoxygenase are thus useful in the treatment of disease states such as those listed above in which the leukotrienes play an important role.

U.S. Pat. No. 3,859,305 to Posselt, et at. discloses certain indole aminoketones which are useful as cardiovascular agents.

U.S. Pat. No. 3,931,229 to Zinnes, et at. discloses and claims certain 3-thiomethyl-(2-[2-(dialkylamino)ethyt]indoles having utility as central nervous system depressants and anti-aggression agents.

U.S. Pat. No. 4,021,448 to Bell discloses and claims certain 2-substituted-indole-1-(lower alkane)carboxarnides having utility for decreasing gastric secretions and as antiulcer agents.

U.S. Pat. No. 4,119,638 to Ray discloses and claims certain thioesters of 1-(4-chlorobenzoyl)-5-methoxy-2-methylindole-3-acetic acid useful as antiinflammatory agents.

U.S. Pat. No. 4,464,379 to Betzing, et at. discloses and claims certain 1-(4-chlorobenzoyl)-2-methyl-5-methoxyindole-3-acetic acid derivatives having antithrombic, antiarteriosclerotic, and antiphlogisfic activity.

European Patent Application 87 31103 1.6 (Publication No. 0 275 667) to Gillard, et at. discloses and claims certain 3-(hetero-substituted)-N-benzylindoles as leukotriene biosynthesis inhibitors.

S. Raucher, et at., in "Indole Alkaloid Synthesis via Claissen Rearrangement," *J. Am. Chem. Soc.*, 103(9):2419–2412 (1981), disclose certain 1H-indole-2-acetic acid derivatives.

Kobayashi, et al., in "Indole Derivatives XII. Reaction of Indole-2-carboxylic Acid Derivatives with Carbon Disulfide," *Yakugaku Zasshi*, 91(11): 1164–1173 (1971) (in Japanese; *Chemical Abstracts* English-language abstract: CA76: 46033k (1972)), disclose the synthesis of certain 1-methyl-2-carboxarnido- 3-(dithioester)-indoles.

SUMMARY OF THE INVENTION

It has been found, in accordance with the present invention that certain substituted indolyl compounds are effective inhibitors of leukotriene biosynthesis and are thus useful for the treatment or amelioration of inflammatory disease states in which the leukotrienes play a role. In one embodiment of the present invention, there are provided compounds of Formula I:

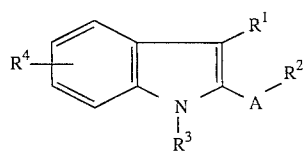

or a pharmaceutically acceptable salt, ester, or amide thereof.

In the compounds of this invention, A is selected from the group consisting of straight or branched divalent alkylene of from one to twelve carbon atoms, straight or branched divaient alkenylene of from two to twelve carbon atoms, and divalent cycloalkylene of from three to eight carbon atoms.

The substituent group $R^1$ is selected from the group consisting of hydrogen; alkylthio of from one to six carbon atoms; phenylthio; phenylalkylthio in which the alkyl portion contains from one to six carbon atoms; 2-, 3-, and 4-pyridylthio; 2- and 3-thienylthio; 2-thiazolylthio; and a group having the structure

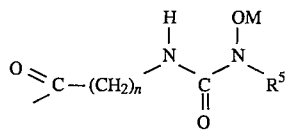

with the proviso that when $R^1$ is $-C(O)(CH_2)_n NHC(O)N(OM)R^5$, then $R^2$ is selected from $-COOH$, $-COO^- B^+$ where B is a pharmaceutically acceptable cation, and $-COO(alkyl)$ where the alkyl group is of from one to six carbon atoms. In the foregoing definition of $R^1$, the phenyl ring of the phenylthio or phenylalkylthio groups are optionally substituted with one or two groups selected from alkyl of from one to six carbon atoms, haloalkyl of from one to six carbon atoms, alkoxy of from one to twelve carbon atoms, hydroxy and halogen.

The substituent group $R^2$ is selected from the group consisting of

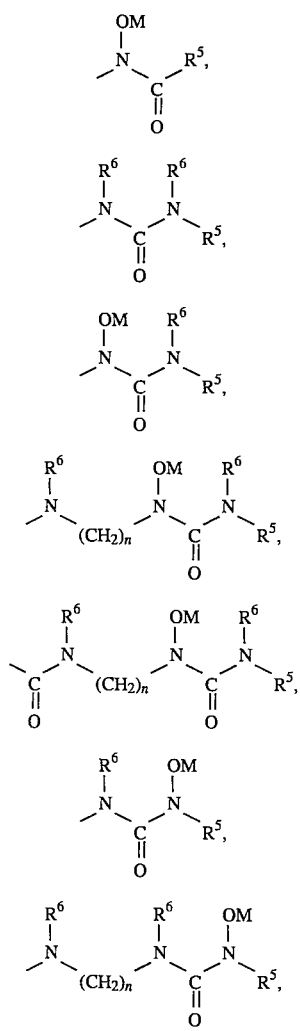

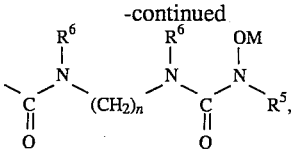

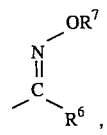

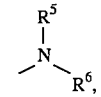

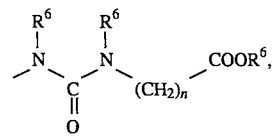

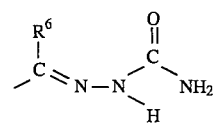

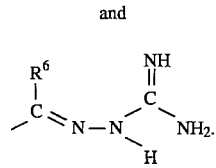

In the foregoing definitions of $R^2$, n is an integer of from one to four, and $R^5$ is selected from the group consisting of (1) alkyl of from one to six carbon atoms, (2) hydroxyalkyl of from one to six carbon atoms, (3) phenylalkyl in which the alkyl portion contains from one to six carbon atoms, (4) alkoxyalkyl in which the alkoxy and alkyl portions each, independently, contain from one to six carbon atoms, (5) phenoxyalkyl in which the alkyl portion contains from one to six carbon atoms, (6) (alkoxyalkoxyl)alkyl in which each alkoxy portion, independently, contains from one to six carbon atoms, and the alkyl portion contains from one to six carbon atoms, (7) (alkoxycarbonyl)alkyl in which the a/koxycarbonyl portion contains from two to six carbon atoms and the alkyl portion contains from one to six carbon atoms, (8) (aminocarbonyl)alkyl in which the alkyl portion contains from one to six carbon atoms, (9) ((alkylamino)carbonyl)alkyl in which each alkyl portion independently contains from one to six carbon atoms,

(10) ((dialkylamino)carbonyl)alkyl in which each alkyl portion independently contains from one to six carbon atoms,

(11) 2-, 3-, and 4-pyridylalkyl in which the alkyl portion contains from one to six carbon atoms,

(12) (2-furyl)alkyl in which the alkyl portion contains from one to six carbon atoms,

(13) (3-thienyl)alkyl in which the alkyl portion contains from one to six carbon atoms,

(14) (2-benzo[b]thienyl)alkyl in which the alkyl portion contains from one to six carbon atoms,

(15) (2-benzo[b]furyl)alkyl in which the alkyl portion contains from one to six carbon atoms,

(16) (5-(1,2,4-triazolyl))alkyl in which the alkyl portion contains from one to six carbon atoms,

(17) (2-imidazolyl)alkyl in which the alkyl portion contains from one to six carbon atoms,

(18) (2-thiazolyl)alkyl in which the alkyl portion contains from one to six carbon atoms,

(19) (2-pyrimidyl)alkyl in which the alkyl portion contains from one to six carbon atoms, and

(20) (5-tetrazolyl)alkyl in which the alkyl portion contains from one to six carbon atoms.

In the foregoing definition of $R^2$, the substituent group $R^6$ is, at each occurrence, selected from hydrogen, and alkyl of from one to six carbon atoms and the substituent group $R^7$ is selected from the group consisting of (1) alkyl of from one to six carbon atoms, (2) hydroxyalkyl of from one to six carbon atoms, (3) phenylalkyl in which the alkyl portion contains from one to six carbon atoms, (4) ((carboxy)phenyl)alkyl in which the alkyl portion contains from one to six carbon atoms, (5) alkoxyalkyl in which the alkoxy and alkyl portions each, independently, contain from one to six carbon atoms, (6) phenoxyalkyl in which the alkyl portion contains from one to six carbon atoms, (7) (carboxyl)alkyl in which the alkyl portion contains from one to six carbon atoms, (8) (C-malanato)alkyl in which the alkyl portion contains from one to six carbon atoms, (9) (C-(dialkylmalanato))alkyl in which each alkyl portion, independently, contains from one to six carbon atoms,

(10) (alkoxyalkoxyl)alkyl in which each alkoxy portion, independently, contains from one to six carbon atoms, and the alkyl portion contains from one to six carbon atoms,

(11) (alkoxycarbonyl)alkyl in which the alkoxycarbonyl portion contains from two to six carbon atoms and the alkyl portion contains from one to six carbon atoms,

(12) ((N-alkyl-N-hydroxyamino)carbonyl)alkyl in which each alkyl portion, independently, contains from one to six carbon atoms,

(13) (aminocarbonyl)alkyl in which the alkyl portion contains from one to six carbon atoms,

(14) ((alkylamino)carbonyl)alkyl in which each alkyl portion independently contains from one to six carbon atoms,

(15) ((dialkylamino)carbonyl)alkyl in which each alkyl portion independently contains from one to six carbon atoms,

(16) (N-morpholinyl)alkyl in which the alkyl portion contains from one to six carbon atoms,

(17) (N-thiomorpholinyl)alkyl in which the alkyl portion contains from one to six carbon atoms,

(18) (N-piperidinyl)alkyl in which the alkyl portion contains from one to six carbon atoms,

(19) (N-piperazinyl)alkyl in which the alkyl portion contains from one to six carbon atoms,

(20) 2-, 3-, and 4-pyridylalkyl in which the alkyl portion contains from one to six carbon atoms,

(21) (2-furyl)alkyl in which the alkyl portion contains from one to six carbon atoms,

(22) (3-thienyl)alkyl in which the alkyl portion contains from one to six carbon atoms,

(23) (2-benzo[b]thienyl)alkyl in which the alkyl portion contains from one to six carbon atoms,

(24) (2-benzo[b]furyl)alkyl in which the alkyl portion contains from one to six carbon atoms,

(25) (5-(1,2,4-triazolyl))alkyl in which the alkyl portion contains from one to six carbon atoms,

(26) (2-imidazolyl)alkyl in which the alkyl portion contains from one to six carbon atoms,

(27) (2-thiazolyl)alkyl in which the alkyl portion contains from one to six carbon atoms,

(28) (2-pyrimidyl)alkyl in which the alkyl portion contains from one to six carbon atoms, and

(29) (5-tetrazolyl)alkyl in which the alkyl portion contains from one to six carbon atoms.

The group M is selected from the group consisting of hydrogen, a pharmaceutically acceptable cation, and a pharmaceutically acceptable metabolically cleavable group.

$R^3$ is selected from the group consisting of phenylalkyl in which the alkyl portion contains from one to six carbon atoms; and heteroarylalkyl in which the alkyl portion contains from one to six carbon atoms and the heteroaryl group is selected from the group consisting of 2-, 3- and 4-pyridyl, 2- and 3-thienyl, 2- and 3-furyl, indolyl, pyrazinyl, isoquinolyl, quinolyl; imidazolyl, pyrrolyl, pyrimidyl, benzofuryl, benzothienyl, thiazolyl; and carbazolyl.

In the foregoing definition of $R^3$, the rings of the phenylalkyl or heteroarylalkyl groups are optionally substituted with one or two groups selected from alkyl of from one to six carbon atoms; alkoxy of from one to twelve carbon atoms; halogen; hydroxy phenyl, optionally substituted with alkyl of from one to six carbon atoms, haloalkyl of from one to six carbon atoms, alkoxy of from one to six carbon atoms, hydroxy, or halogen; phenoxy, optionally substituted with alkyl of from one to six carbon atoms, haloalkyl of from one to six carbon atoms, alkoxy of from one to six carbon atoms, hydroxy, or halogen; 2-, 3-, or 4-pyridyl, optionally substituted with alkyl of from one to six carbon atoms, haloalkyl of from one to six carbon atoms, alkoxy of from one to six carbon atoms, hydroxy, or halogen; and 2-, 3-, or 4-pyridyloxy, optionally substituted with alkyl of from one to six carbon atoms, haloalkyl of from one to six carbon atoms, alkoxy of from one to six carbon atoms, hydroxy, or halogen; and $—(CH_2)_nN(OH)C(O)NRSR^6$; and $—(CH_2)_nN(RS)C(O)N(OM)R^6$; with the proviso that when $R^3$ is $—(CH_2)_nN(OH)C(O)NRSR^6$ or $—(CH_2)_nN(R^6)C(O)N(OM)R^6$, then $R^2$ is selected from —COOH, —COO$^-$ B$^+$ where B is a pharmaceutically acceptable cation, and —COO(alkyl) where the alkyl group is of from one to six carbon atoms.

In the compounds of this invention, $R^4$ is selected from the group consisting of (1) alkyl of from one to six carbon atoms; (2) alkoxy of from one to twelve carbon atoms; (3) phenyl; (4) phenoxy; (5) phenylalkyloxy in which the alkyloxy portion contains from one to six carbon atoms; and (6) 1- and 2-naphthylalkyloxy in which the alkyloxy portion contains from one to six carbon atoms; in which the ting portion of each of the foregoing is optionally substituted with (a) alkyl of from one to six carbon atoms, (b) haloalkyl of from one to six carbon atoms, (c) alkoxy of from one to six carbon atoms, (d) hydroxy or (e) halogen. Additionally, $R^4$ is selected from heteroarylalkyloxy in which the alkyloxy portion contains from one to six carbon atoms and the heteroaryl portion is selected from the group consisting of (7) 2-, 3-, and 6-quinolyl; (8) 2-, 3-, and 4-pyridyl; (9) 2-benzothiazolyl; (10) 2-quinoxalyl; (11) 2- and 3-indolyl; (12) 2- and 3-benzimidazolyl; (13) 2- and 3-benzo[b]thienyl; (14) 2- and 3-benzo[b]furyl; (15) 2-benzimidazolyl; (16) 2-thiazolyl, and (17) 1-, 3-, and 4-isoquinolyl, wherein the ting portion of each of the foregoing groups (7) through (17) is optionally substituted with alkyl of from one to six carbon atoms, haloalkyl of from one to six carbon atoms, alkoxy of from one to twelve carbon atoms, halogen, or hydroxy.

DETAILED DESCRIPTION AND PREFERRED EMBODIMENTS

As used throughout this specification and the appended claims, the term "alkyl" refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The term "alkylene" denotes a divalent group derived from a straight or branched chain saturated hydrocarbon by the removal of two hydrogen atoms, for example methylene, 1,2-ethylene, 1,1-ethylene, 1,3-propylene, and the like.

The term "alkenyl" denotes a monovalent group derived from a hydrocarbon containing at least one carbon-carbon double bond by the removal of a single hydrogen atom. Alkenyl groups include, for example, ethenyl, propenyl, butenyl, 1-methyl-2-buten-1-yl and the like.

The term "alkenylene" denotes a divalent group derived from a straight or branched chain hydrocarbon containing at least one carbon-carbon double bond. Examples of alkenylene include —CH=CH—, —CH$_2$CH=CH—, —C(CH$_3$)=CH—, —CH$_2$CH=CHCH$_2$—, and the like.

The term "cycloalkylene" refers to a divalent group derived from a saturated carbocyclic hydrocarbon by the removal of two hydrogen atoms, for example cyclopropylene, cyclopentylene, cyclohexylene, and the like.

The term "alkylthio" denotes an alkyl group, as defined above, attached to the parent molecular moiety through a sulfur atom.

The terms "heterocyclic aryl" and "heteroaryl" as used herein refers to substituted or unsubstituted 5- or 6-membered ring aromatic groups containing one, two or three nitrogen atoms, one nitrogen and one sulfur atom, or one nitrogen and one oxygen atom. The term heteroaryl also includes bi- or tricyclic groups in which the aromatic heterocyclic ting is fused to one or two benzene rings. Representative heteroaryl groups are pyridyl, thienyl, furyl, indolyl, pyrazinyl, isoquinolyl, quinolyl, imidazolyl, pyrrolyl,-pyrimidyl, benzofuryl, benzothienyl, carbazolyl, and the like.

The term "metabolically cleavable group" denotes a group which is cleaved in vivo to yield the parent molecule in which M is hydrogen. Examples of metabolically cleavable groups include —COR, —COOR, —CONRR and —CH$_2$OR radicals where R is selected independently at each occurrence from alkyl, trialkylsilyl, carbocyclic aryl or carbocyclic aryl substituted with one or more of C$_1$–C$_4$ alkyl, halogen, hydroxy or C$_1$–C$_4$ alkoxy. Representative metabolically cleavable groups include acetyl, methoxycarbonyl, benzoyl, methoxymethyl and trimethylsilyl groups.

The term "hydroxyalkyl" means an alkyl group as defined above, having one, two or three hydrogen atoms replaced by hydroxyl groups, with the proviso that no more than one hydroxy group may be attached to a single carbon atom of the alkyl group.

The term "phenylalkyl" denotes a phenyl group attached to the parent molecular moiety through an alkylene group.

"Alkoxy" means an alkyl group, as defined above, attached to the parent molecular moeity through an oxygen atom. Representative alkoxy groups include methoxy, ethoxy, propoxy, tert-butoxy and the like.

"Alkoxyalkyl" means an alkoxy group, as defined above, attached to the parent molecular moiety through an alkylene group.

The term "phenoxy" represents a phenyl group attached to the parent molecular moiety through an oxygen atom.

The term "phenoxyalkyl" denotes a phenoxy group attached to the parent molecular moiety through an alkylene group. Typical phenoxyalkyl groups include phenoxymethyl, phenoxyethyl, and the like.

"(Alkoxyalkoxy)alkyl stands for a group in which an alkoxy group, as defined above is attached through its oxygen atom to a second alkoxy group which, in turn, is attached through an alkylene group to the parent molecular moiety. Representative (alkoxyalkoxy)alkyl groups include methoxymethoxymethyl, methylethoxymethyl, ethoxyethoxymethyl, and the like.

The term "(alkoxycarbonyl)alkyl denotes an ester group (—COOalkyl)) attached through an alkylene group to the parent molecular moiety, for example, ethoxycarbonylmethyl, ethoxycarbonylethyl, and the like.

The terms "(aminocarbonyl)alkyl," "(alkylaminocarbonyl)alkyl," and "(dialkylaminocarbonyl)Alkyl" mean, respectively, an amino group, or an amino group substituted by one or two alkyl groups, as defined above, attached through a carbonyl group and thence through an alkylene group to the parent molecular moiety. Representative groups of this type include —(CH$_2$)C(O)NH$_2$, —(CH$_2$)C(O)NHCH$_3$, —(CH$_2$)C(O)N(CH$_3$)$_2$ and the like.

The term "(C-malanato)alkyl" represents a malonic acid group, attached through its methylene carbon to the parent molecular moiety through an alkylene group; i.e. a group of the formula

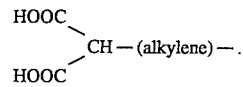

Similarly, the term "(C-(dialkylmalanato))alkyl represents a malonic acid group in which the two acid functional groups have been esterified with alkyl groups, attached to the parent molecular moiety at its methylene carbon through an alkylene group.

The term "((N-alkyl-N-hydroxyamino)carbonyl)alkyl" stands for a group of the formula

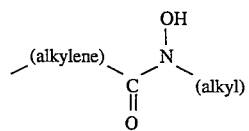

in which "alkylene" and "alkyl" are as defined above.

The compounds of the present invention comprise a class of substituted indoles in which the 3-position is substituted by an alkylthio group or an

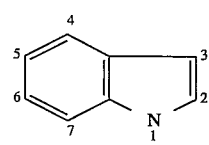

(N-hydroxyamido)alkylcarbonyl group of the formula

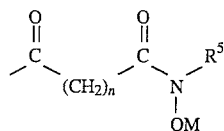

in which n is an integer of from one to four, M is as previously defined, and $R^5$ is hydrogen or lower alkyl. Preferred compounds of the present invention are those in which the 3-position substituent is alkylthio.

The 2-position of the indole nucleus of the compounds of the present invention is substituted with a urea, N-hydroxyurea, hydroxamate, guanidyl, or hydroximino group, any of which may be further substituted. These groups are attached to the indole nucleus through an alkylene, alkenylene, or cycloalkylene spacing group. Preferred compounds of the present invention are those in which the substituent at the 2-position of the indole nucleus is selected from N-hydroxyurea groups of the structures

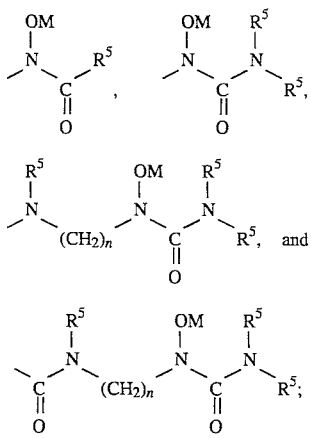

N'-hydroxyurea groups of the structures

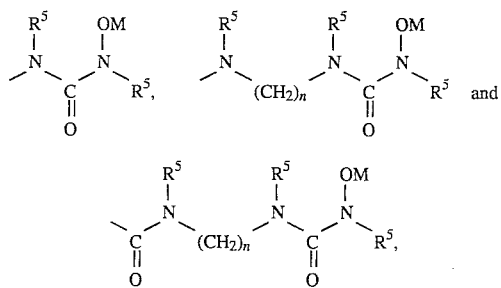

urea groups of the structure

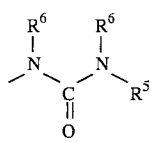

and O-substituted oxime groups of the structure

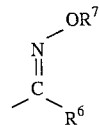

where $R^5$, $R^6$ $R^7$ and are as defined above.

The 1-position of the indole nucleus of compounds of this invention is substituted by an alkyl-substituted carbocyclic aromatic group, an alkyl-substituted heteroaryl group, an N-hydroxyurea of the structure —$(CH_2)_nN(OH)C(O)NRSR^6$ or —$CH_2)_nN(R^5)C(O)N(OH)R^6$, where $R^5$ at each occurrence selected from hydrogen and lower alkyl and $R^6$ has the values defined above. The integer, n, is 1 to 4, inclusive. Preferred compounds of the present invention are those where the substituent at position 1 of the indole nucleus is benzyl or benzyl substituted by $C_1-C_6$ alkyl, $C_1-C_6$ alkoxy, phenoxy, halogen, or hydroxy.

Specific examples of compounds contemplated as falling within the scope of this invention include, but are not limited to the following examples, including the pharmaceutically acceptable salts and esters thereof:

N'-hydroxy-N'-methyl-N-2-[2-methyl-3-(1-(4-chlorophenylmethyl)-3-(1,1 -dimethylethylthio)-5-(1-methylethyl)indol-2-yl)]propyl urea;

2,2-dimethyl-3-[1-(4-chlorophenylmethyl)-3-(1,1-dimethylethylthio)-5-(1 -methylethyl)indol-2-yl]propionaldehyde oxime;

N-hydroxy-N-2,2-dimethyl- 3-[(1-(4-chlorophenylmethyl )-3-(1,1 -dimethylethylthio)-5-(1-methylethyl))indol-2-yl]propyl urea;

N'-hydroxy-N'methyl-N-2-[(1-(4-chlorophenylmethyl)-3-(1,1-dimethylethylthio)- 5-(1-methylethyl))indol-2-yl] ethyl urea;

N-2,2-dimethyl-3-[(1 -(4-chlorophenylmethyl)-3-(1,1-dimethylethyl-thio)-5-(1 -methylethyl))indol-2-yl]propyl urea;

N'-hydroxy-N'-methyl-N-2-[3-(1-(4-chlorophenylmethyl)-3-(1,1 -dimethylethylthio)-5-(1-methylethyl)indol-2-yl)-2,2dimethylpropionylamino] ethyl urea;

1-(4-chlorophenylmethyl)-2-[2,2-dimethyl-3-((3-hydroxypropyl)-amino)propyl] -3-(1.1-dimethylethylthio)-5-(1-methylethyl)indole;

N-2-[2-methyl-3-(1-(4-chlorophenylmethyl)-3-(1,1-dimethylethylthio)-5-(1 -methylethyl)indol-2-yl)]propyl urea;

3-[3-(1-(4-chlorophenylmethyl)-3-(1,1-dimethylethylthio)-5-(1 -methylethyl)indol-2-yl)-2-aminocarbonylamino-2-methylpropyl]propanoic acid, ethyl ester;

3-[3-(1-(4-chlorophenylmethyl)-3-(1,1-dimethylethylthio)-5-(1 -methylethyl)indol-2-yl)-2-aminocarbonylamino-2-methylpropyl]propanoic acid;

N'-hydroxy-N'-methyl-N-[1-(4-chlorophenylmethyl)-5-(1-methylethyl)-2-((2 -methyl-2-ethoxycarbonyl)propyl)indol-2-yl]-3-oxopropylurea;

1-(4-chlorophenylmethyl)-3-(1,1-dimethylethylthio)-2-[3-(2,2-dimethyl-1 -guanidinylimino)propyl]-5-(1-methylethyl)indole;

N-hydroxy-N-[trans-2-(1-(4-chlorophenylmethyl)-3-(1,1-dimethylethylthio)-5-(1 -methylethyl)indol-2-yl)cyclopropyl]methylurea;

3-[3-(1,1-dimethylethylthio)-5-(1-methylethyl)-1-(4-pyridinylmethyl)indol-2-yl]- 2,2-dimethylpropanoic acid;

3-[3-(1, 1-dimethylethylthio)-5-(1-methylethyl)-1-(2-thienylmethyl)indol-2-yl]- 2,2-dimethylpropanoic acid;

N-hydroxy-N-trans-[3-(1-(4-chlorophenylmethyl)-3-( I, 1-dimethylethylthio)-5-(1 -methylethyl)indol-2-yl)]prop-2-enylurea;

N-[3-(1-(4-chlorophenylmethyl)-3-(1,1-dimethylethylthio)-5-(1-methylethyl)indol-2-yl)-2,2dimethylpropyl]acetohydroxamic acid;

N-hydroxy-N-3-[3-(1-(4-chlorophenylmethyl)-3-(1,1-dimethylethylthio)-5-(1-methylethyl)indol-2-yl)-2,2-dimethylpropionylamino]propyl urea;

3-[1-(4-chlorophenylmethyl)-3-(1,1-dimethylethylthio)-5-(1-methylethyl)indol-2-yl]-2,2-dimethylpropionaldehyde oxime-O-2-acetic acid;

2-(3-amino-2,2-dimethylpropyl)-1-(4-chlorophenylmethyl)-3-(1,1-dimethylethylthio)-5-(1-methylethyl)indole;

N-[3-(1-(4-chlorophenylmethyl)-3-(1,1-dimethylethylthio)-5-(1-methylethyl)indol-2-yl)-2,2-dimethylpropyl]acetamide;

N-[trans-2-(1-(4-chlorophenylmethyl)-3-(1,1-dimethylethylthio)-5-(1-methylethyl)indol-2-yl)cyclopropyl]methyl urea;

N'-hydroxy-N-3-[3-(1.1-dimethylethylthio)-5-(1-methylethyl)-2-((2-methyl-2-ethoxycarbonyl)propyl)indol-1-yl] propyl urea;

2,2-dimethyl-3-[1-(2-thiophenylmethyl)-3-(1,1-dimethylethylthio)-5-(1-methylethyl)indol-2-yl]propionaldehyde oxime;

N-2,2-dimethyl-3-[(1-(2-thiophenylmethyl)-3-(1,1-dimethylethyl-thio)-5-(1-methylethyl)indol-2-yl]propyl urea;

3-[1-(4-chlorophenylmethyl)-3-(1,1-dimethylethylthio)-5-(methoxy)indol-2-yl]-2,2-dimethylpropionaldehyde oxime-O-2-acetic acid;

3-[1-(4-chlorophenylmethyl)-3-(1,1-dimethylethylthio)-5-(1-methylethyl)indol-2-yl]-2,2-dimethylpropionaldehyde oxime-O-3-propionic acid;

N-{3-[1-(4-chlorophenylmethyl)-3-(1,1-dimethylethylthio)-5-(1-methylethyl)indol-2-yl]-2,2-dimethylpropionaldehyde oxime-O}-methyl urea;

N-2-[1-(4-chlorophenylmethyl)-3-(1,1-dimethylethylthio)-5-(1-methylethyl)indol-2-yl)-2,2-dimethylpropionylamino]ethyl urea;

3-[1-(4-fluorophenylmethyl)-3-(1,1-dimethylethylthio)-5-(1-methylethyl)-indol-2-yl]-2,2-dimethylpropionaldehyde oxime-O-2-acetic acid;

3-[1-(4-chlorophenylmethyl)-3-(1,1-dimethylethylthio)-5-(1-methylethyl)-indol-2-yl]-2,2-dimethylpropionaldehyde oxime-O-2-propionic acid;

3-[3-(1,1-dimethylethylthio)-5-(quinolin-2-ylmethoxy)-1-(4-chlorophenylmethyl)-indol-2-yl]-2,2-dimethylpropionaldehyde oxime-O-2-acetic acid;

3-[3-(1,1-dimethylethylthio)-5-(quinolin-2-ylmethoxy)-1-(4-chlorophenylmethyl)-indol-2-yl]-2,2-dimethylpropionaldehyde oxime-O-2-(3-methyl)butyric acid 3-[3-(1,1-dimethylethylthio)-5-(6,7-dichloroquinolin-2-ylmethoxy)-1-(4-chlorophenylmethyl) indol-2-yl]-2,2-dimethylpropionaldehyde oxime-O-2-acetic acid;

3-[3-(1,1-dimethylethylthio)-5-(6-fluoroquinolin-2-ylmethoxy)-1-(4-chlorophenylmethyl)indol-2-yl]-2,2-dimethylpropionaldehyde oxime-O-2-propionic acid;

3-[3-(1,1-dimethylethylthio)-5-(6-methoxycarbonyloxy quinolin-2-ylmethoxy)-1-(4-chlorophenylmethyl) indol-2-yl]-2,2-dimethylpropionaldehyde oxime-O-2-propionic acid;

3-[3-(1,1-dimethylethylthio)-5-(quinoxalin-2-ylmethoxy)-1-(4-chlorophenylmethyl) indol-2-yl]-2,2-dimethylpropionaldehyde oxime-O-2-acetic acid;

3-[3-(1,1-dimethylethylthio)-5-(6-methoxynaphth-2-ylmethoxy)-1-(4-chlorophenylmethyl) indol-2-yl]-2,2-dimethylpropionaldehyde oxime-O-2-acetic acid;

3-[3-(1,1-dimethylethylthio)-5-(2-oxyquinolin-6-ylmethoxy)-1-(4-chlorophenylmethyl) indol-2-yl]-2,2-dimethylpropionaldehyde oxime-O-2-acetic acid;

3-[3-(1,1-dimethylethylthio)-5-(pyrid-2-ylmethoxy)-1-(4-chlorophenylmethyl) indol-2-yl]-2,2-dimethylpropionaldehyde oxime-O-2-acetic acid;

3-[3-(1,1-dimethylethylthio)-5-(N-methylindol-2-ylmethoxy)-1-(4-chlorophenylmethyl) indol-2-yl]-2,2-dimethylpropionaldehyde oxime-O-2-acetic acid;

3-[3-(1,1-dimethylethylthio)-5-(4-fluorophen-2-ylmethoxy)-1-(4-chlorophenylmethyl) indol-2-yl]-2,2-dimethylpropionaldehyde oxime-O-2-acetic acid; and 3-[3-(1,1-dimethylethylthio)-5-((3-(4-fluorophenoxy)-4-fluorophen-2-ylmethoxy)-1-(4-chlorophenylmethyl)) indol-2-yl]-2,2-dimethylpropionaldehyde oxime-O-2-acetic acid.

Certain compounds of this invention may exist in geometric or stereoisomeric forms. The present invention contemplates all such compounds, including cis- and trans-geometric isomers, R- and S-enantiomers, diastereomers, and mixtures thereof as falling within the scope of the invention. If a particular enantiomer is desired, it may be prepared by chiral synthesis or by derivatization with a chiral auxiliary where the resulting diastereomeric mixture is separated and the auxiliary group cleaved to provide the pure desired enantiomers. Alternatively, where the molecule contains a basic functional group such as amino or an acidic functional group such as carboxyl, diastereomeric salts are formed with an appropriate optically active acid or base, followed by resolution of the diastereomers thus formed by fractional crystallization or chromatographic means well known in the art and subsequent recovery of the pure enantiomers.

Certain compounds of the present invention may contain a basic functional group such as amino, alkylamino, or dialkylamino and are thus capable of forming salts with pharmaceutically acceptable acids. The term "pharmaceutically acceptable salts" in this respect, refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, titrate, maleate, fumarate, succinate, tartrate, naphthylate, mesylate, glucoheptonate, lactobionate, laurylsulphonate salts and the like. (See, for example S. M. Berge, et al., "Pharmaceutical Salts," *J. Pharm. Sci.,* 66: 1–19 (1977) which is incorporated herein by reference.)

In other cases, the compounds may contain one or more acidic functional groups such as carboxyl and the like and are capable of forming salts with pharmaceutically acceptable bases. The term "pharmaceutically acceptable salts" in these instances refers to the relatively non-toxic, inorganic and organic base addition salts of compounds of the present invention. These salts can be likewise prepared in situ during the final isolation and purification of the compounds or by separately reacting the purified compound in its free acid form with a suitable base such as the hydroxide, carbonate or bicarbonate of a pharmaceutically acceptable metal cation or with ammonia, or an organic primary, secondary, or tertiary amine. Representative alkali or alkaline earth salts include the lithium, sodium, potassium, calcium, magnesium and aluminum salts and the like. Representative organic amines useful for the formation of base addition salts include ethylamine, diethylamine, ethylenediamine, ethanolamine, diethanolamine, piperazine, and the like.

(See, for example S. M. Berge, et al., "Pharmaceutical Salts," *J. Pharm. Sci.*, 66:1–19 (1977) which is incorporated herein by reference.)

Synthesis of the Compounds

The compounds of the present invention are synthesized by the following general synthetic mutes. One general method for the synthesis of intermediate indoles used to prepare compounds of this invention, shown in Reaction Scheme 1, employs the Fischer indole synthesis (cf. Advanced Organic Chemistry, Reactions, Mechanisms, and Structure, 3rd Ed. by J. March, John Wiley and Sons, 85, p. 1032). In this method a hydrazine I is reacted with ketone II in a suitable solvent at a temperature between 20° C. and the refluxing temperature of the chosen solvent to provide the indole product III. The intermediate indole III is subsequently transformed by the procedures described for individual examples to provide the final products of this invention.

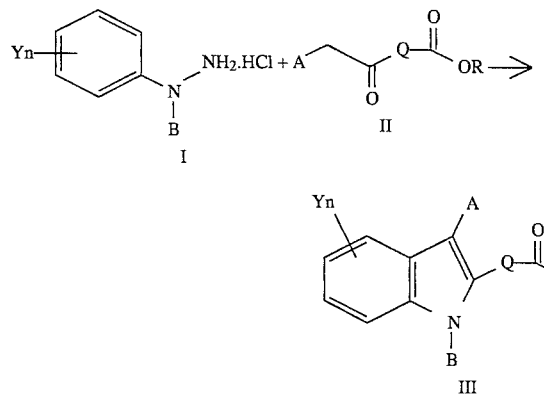

Another general method illustrated in Reaction Scheme 2, involves the reaction of hydrazine intermediate IV with the ketone intermediate V to provide the indole intermediate VI. The intermediate VI is then treated under basic conditions with a halogenated alkylaryl compound VII, where aryl is a heteroaryl group such as furanyl, thienyl, pyridyl, pyrimidyl, thiazoyl, benzothiazolyl, benzothiophenyl, benzofuranyl, or substituted phenyl.

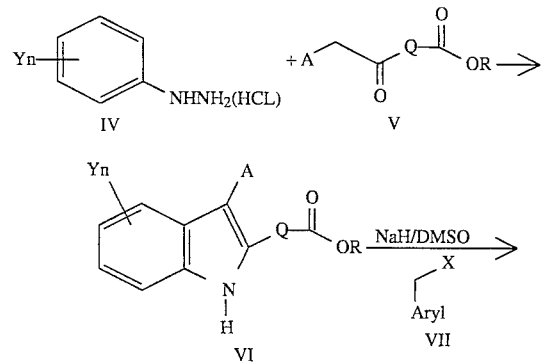

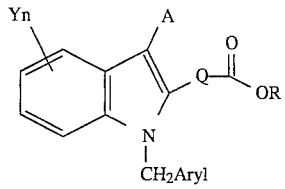

Inhibition of Leukotriene Biosynthesis In Vitro

Inhibition of leukotriene biosynthesis by representative compounds of the present invention was evaluated in assays involving calcium ionophore-induced $LTB_4$ biosynthesis expressed by human polymorphonuclear leukocytes (PMNL) or human whole blood. Human PMNL were isolated from heparinized (20 USP units/mL) venous blood using Ficoll-Hypaque Mono-Poly Resolving Medium. Human PMNL suspensions ($5 \times 10^6$ cells/250 µL) were pre-incubated with test compounds or vehicle for 15 min at 37° C. followed by calcium ionophore A23187 challenge (final concentration of 8.3 µM) and the reaction terminated after 10 rain by adding two volumes of methanol containing prostaglandin $B_2$ as an internal recovery standard. The methanol extracts were analyzed for $LTB_4$ content by HPLC or radioimmunoassay.

The assay using human heparinized whole blood was incubated for 30 minutes at 37° C. after adding 50 µm of ionophore A23187. The plasma layer was obtained by centrifugation and deproteinized by the addition of four volumes of methanol. The methanol extract was analyzed for $LTB_4$ by HPLC or radioimmunoassay.

The inhibitory activity of representative examples is shown in Table 1.

TABLE 1

| Inhibition of $LTB_4$ Biosynthesis in Human PMNL and Human Whole Blood | | |
|---|---|---|
| | Blood | |
| Example | Human PMNL $IC_{50}$ (µM) | Human Whole Blood $IC_{50}$ (µM) |
| 1 | 0.15 | 1.3 |
| 2 | 0.27 | 2.2 |
| 3 | 0.17 | 1.6 |
| 4 | 0.57 | 6.7 |
| 5 | 0.18 | 0.71 |
| 6 | 0.15 | 1.2 |
| 6.2 | 0.31 | 1.4 |
| 7 | 4.2 | 6.9 |
| 8 | 0.4 | 5.2 |
| 9 | 77% @ 1.6 | 5.6 |
| 10 | 70% @ 1.6 | 2.5 |
| 11 | 1.5 | 6.9 |
| 12 | 100% @ 3.1 | 1.3 |
| 13 | — | 3.0 |
| 14 | 40% @ 0.78 | 2.5 |
| 15 | 0.09 | 0.9 |
| 16 | — | 5.5 |
| 20 | — | 0.68 |
| 21 | — | 1.1 |
| 22 | — | 2.1 |
| 23 | 0.4 | 2.7 |
| 24 | 1.1 | — |

Inhibition of Leukotriene Biosynthesis In Vivo

Inhibition of the biosynthesis of leukotrienes in vivo after oral administration of compound was determined using a rat peritoneal anaphylaxis model in a similar manner as that described by Young and coworkers (Young, P. R.; Dyer, R. D.; Carter, G. W. *Fed. Proc., Fed. Am. Soc. Exp. Biol.* 1985, 44, 1185). In this model rats were injected intraperitoneally (ip) with rabbit antibody to bovine serum albumin (BSA) and three hours later injected ip with BSA to induce an antigen-antibody response. Rats were sacrificed 15 minutes after this challenge and the peritoneal fluids were collected and analyzed for leukotriene levels. Test compounds were administered by garage one hour prior to the antigen challenge. Percent inhibition values were determined by comparing the treatment group to the mean of the control group. Compounds of this invention are orally effective in preventing the in vivo bio-synthesis of leukotrienes as illustrated for representative examples shown in Table 2.

TABLE 2

Inhibition of Leukotriene (LT) Biosynthesis In Vivo

| Example | Percent Leukotriene inhibition at 100 μmol/kg oral dose |
| --- | --- |
| 2 | 46% |
| 3 | 68% |
| 5 | 86% |
| 6 | 86% |
| 20 | 99% |

Pharmaceutical Compositions

The present invention also provides pharmaceutical compositions which comprise one or more of the compounds of formula I above formulated together with one or more non-toxic pharmaceutically acceptable carriers. The pharmaceutical compositions may be specially formulated for oral administration in solid or liquid form, for parenteral injection, or for rectal or vaginal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of suffactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like, Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(onhoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated

17 form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g. two to four separate doses per day.

The following examples are presented to enable one skilled in the art to practice the present invention. These examples are merely illustrative and should not be read as limiting the invention as it is defined by the appended claims.

18

EXAMPLE 1

Preparation of
N'-hydroxy-N'-methyl-N-2-[2-methyl-3-(1-(4-chlorophenylmethyl)-3-(1,1-dimethylethylthio)-5-(1-methylethyl)indol-2-yl)propyl urea

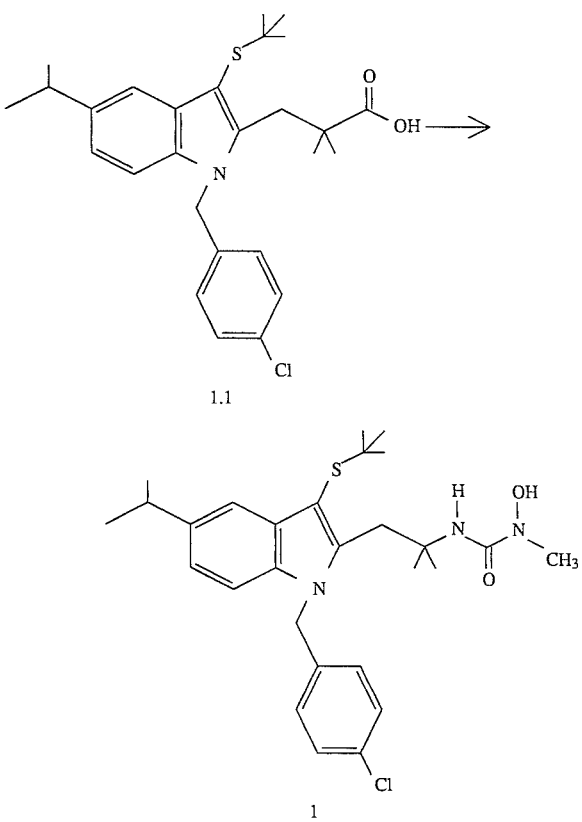

Compound 1.1 was prepared by adaptation of the procedure reported in EPA 87311031.6. To a stirring benzene (7.4 mL) solution of Compound 1.1 (525 mg, 1.11 mmol), triethylamine (0.16 mL, 1.17 mmol) and diphenylphosphorylazide (0.25 mL, 1.11 mmol) were added. The reaction was refluxed for one hour;, N-methyl-hydroxylamine hydrochloride (96 mg, 1.12 mmol) in triethylamine (0.16 mL, 1.13 mmol) and $H_2O$ (0.25 mL) was added, and the reaction stirred two hours at reflux. The cooled reaction mixture was poured into aq. sat'd $NH_4Cl$ and extracted with EtOAc (2×). The combined organic extracts were washed (sat'd, aq $NaHCO_3$, $H_2O$, and brine), dried ($MgSO_4$), and concentrated in vacuo to yield 362 mg of desired product 1 as a cream-colored amorphous solid, after purification by chromatography (silica gel, 35% EtOAc/hexanes). m.p. 95°–100° C.; $^1H$ NMR (300 MHz, DMSO-$d_6$); 1.20 (9H, s), 1.23 (6H, d, 7.5 Hz), 1.3 (6H, s), 2.95 (4H, m), 3.38 (2H, s), 5.57 (2H, s), (1H, s), 6.87 (2H, d, J=8.4 Hz), 6.97 (1H, dd, .[=8.4, 1.5 Hz), 7.27 (1H, d, 9Hz), 7.34 (2H, d, J=9Hz), 7.48 (1H, d, J=1.5 Hz), 9.42 (1H, s); MS $(M+H)^+$ =516. Analysis calc'd for $C_{28}H_{38}ClN_3O_2S$: C, 65.16; H, 7.42; N, 8.14; Found: C, 64.87; H, 7.45; N, 7.94.

EXAMPLE 2

Preparation of 2,2-dimethyl-3-[1-(4-chlorophenylmethyl)-3-(1,1-dimethylethylthio)-5-(1-methylethyl)indol-2-yl]propionaldehyde oxime

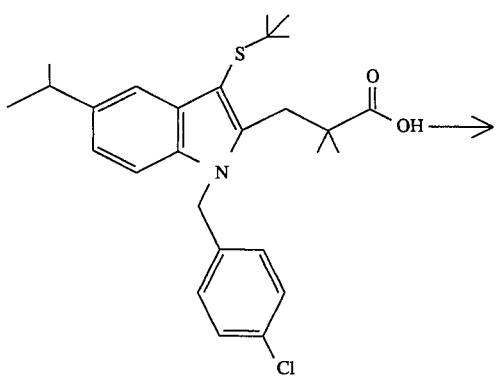

1.1

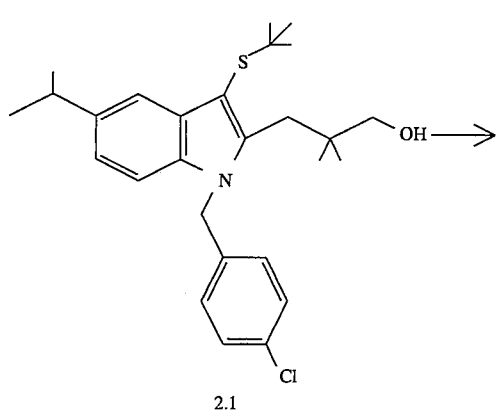

2.1

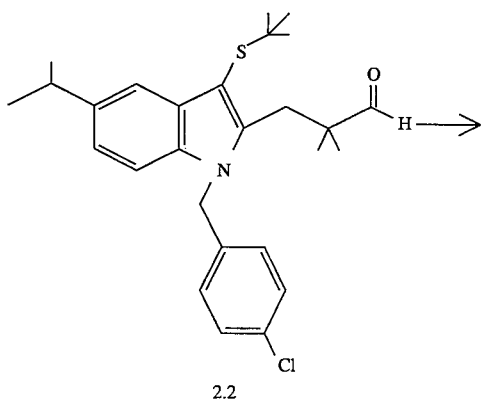

2.2

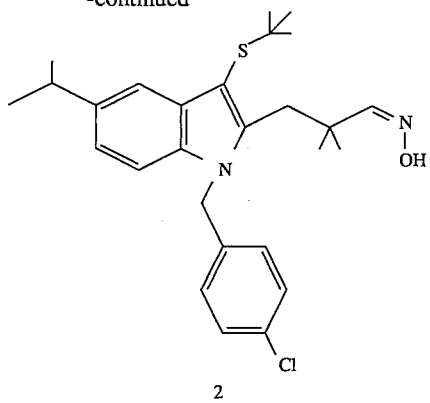

2

Compound 2.1 was prepared by reduction of compound 1.1 as follows. To a 0° C. solution of Compound 1.1 (2.61 g, 5.53 mmol) in 50 mL of dry THF, a 2.0 M (THF) borane dimethylsulfide solution was added dropwise (5.80 mL, 11.6 retool). The reaction was stirred 17 hours at room temperature; methanol (10 mL) was added, and it was then concentrated in vacuo, filtered through a silica gel pad, and purified by chromatography (silica gel, 20% EtOAc/hexanes) to obtain 1.69 g of compound 2.1 as a white, amorphous solid. m.p. 67°–70° C.; $^1$H NMR (300 MHz, DMSO-$d_6$); 0.82 (6H, s), 1.18 (9H, s), 1.22 (6H, d, J=7.75 Hz), 2.93 (3H, m), 3.15 (2H, d, J=6 Hz), 4.82 (1H, t, J=6 Hz), 5.58 (2H, s), 6.87 (2H, d, J= 8.25 Hz), 6.97 (1H, dd, J -8.25 and 1.5 Hz), 7.25 (1H, d, J=8.25), 7.33 (2H, d, J=8.25 Hz), 7.47 (1H, d, J=1.5 Hz); MS (M+H)$^+$=458.

To a −63° C. solution of oxalylchloride (0.41 mL, 4.66 mmol) in dry methylene chloride (4.7 mL), the following reagents were added: DMSO (0.41 mL, 5.32 mmol) in dry methylene chloride (5.32 mL) (dropwise over a five minute period) and Compound 2 (1.22 g, 2.66 mmol) in dry methylene chloride (18 mL) (also dropwise over a five minute period). The reaction was stirred ten minutes after the addition of Compound 2 was completed, and then triethylamine (1.67 mL, 12.0 mmol) in dry methylene chloride (4.0 mL) was added dropwise over a five minute period and stirred one hour before quenching the cold reaction mixture with 10% KHSO$_4$ (aq). This solution was poured into a separatory funnel containing hexanes. The layers were separated, and the aqueous back extracted with ether. The organic layers were combined, washed (1×sat'd, aq NaHCO$_3$; 1 ×H$_2$O; and 3×brine), dried (MgSO$_4$), and concentrated in vacuo to yield 1.16 g of a yellow, amorphous solid aldehyde intermediate 2.2.

To a stirring solution of Compound 2.2 (1.16 g, 2.54 mmol) in ethanol(8.5 mL), under N$_2$(g), pyridine (0.26 mL, 3.18 mmol) and hydroxylamine hydrochloride (210 mg, 3.05 mmol) were added neat and sequentially. The reaction was stirred 16 hours before concentrating in vacuo to yield 1.20 g of Compound 2 as a pale, yellow amorphous solid. A portion of oxime was purified by flash chromatography (silica gel, 10% EtOAc/hexanes) to yield 179 mg of the title compound as an amorphous white solid. m.p. 80°–85° C.; ¹H NMR (300 MHz, DMSO-$d_6$); 1.08 (6H, s), 1.20 (9H, s), 1.23 (6H, d, J=6.75 Hz), 2.95 (1H, septet, J=6.75 Hz), 3.08 (2H, br s), 5.45 (2H, s), 6.88 (2H, d, J=8.25 Hz), 6.97 (1H, dd, J=1.5 and 8.25 Hz), 7.26 (1H, d, J=8.25 Hz), 7.32 (2H, d, J=8.25 Hz), 7.39 (1H, s), 7.46 (1H, d, J=1.5 Hz), 10.43 (1H, s); MS (M+H)⁺=471. Analysis calc'd for $C_{27}H_{35}ClN_2OS$: C, 68.84; H, 7.49; N, 5.95; Found: C, 68.56; H, 7.58; N, 5.70.

EXAMPLE 3

Preparation of N-hydroxy-N-2,2-dimethyl-3-[(1-(4-chlorophenylmethyl)-3-(1,1-dimethylethylthio)-5-(1-methylethyl))indol-2-yl]propyl urea

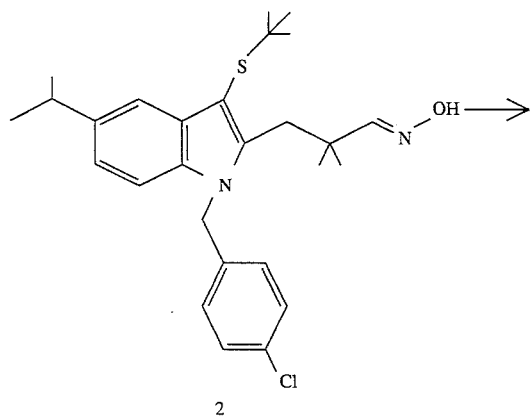

2

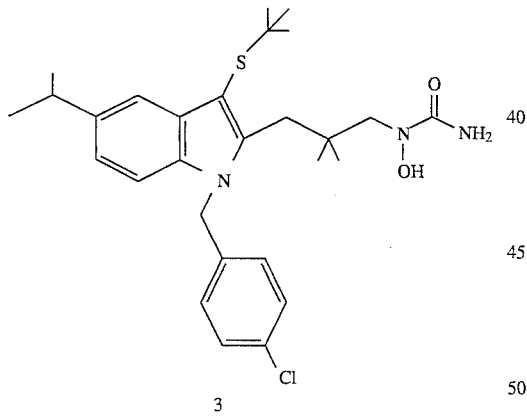

3

To a stirring solution of Compound 2 (1.16 g, 2.46 mmol) in ethanol (5.0 mL), under $N_2$(g) atmosphere, borane pyridine complex (0.84 mL, 8.33 mmol) was added neat. The reaction was stirred for two hours, cooled to 0° C., and 12M HCl (1.4 mL, 16.7 mmol) in ethanol (1.0 mL) added dropwise over a 30 minute period. After stirring 16 hours at room temperature, 50 mL of $H_2O$ was added to the reaction, and 4N NaOH(aq) added to raise the pH to 14. The basic solution was extracted with ether. The organic layer was washed (brine), dried ($MgSO_4$), and concentrated in vacuo. The crude material was purified by chromatography (silica gel, 50% EtOAc/hexanes), yielding 898 mg of hydroxylamine intermediate 3.1 as an amorphous, white solid.

To a stirring solution of 3.1 (642 mg, 1.36 mmol) in THF (5 mL) was added trimethylsilyl isocyanate (0.24 mL, 1.5 mmol). After stirring 90 minutes, additional trimethylsilyl isocyanate(TMSNCO) (0.10 mL, 0.73 mmol) was added. The reaction was stirred for one hour then poured into a separatory funnel containing $NH_4Cl$ (sat'd, aq) and extracted with ethyl acetate. The organic layer was washed (brine), dried ($MgSO_4$), concentrated in vacuo, and purified by chromatography (silica gel, 50–75% EtOAc/hexane) to yield 427 mg of desired product 3 as a white amorphous solid. m.p. 95°–100° C.; ¹H NMR (300 MHz, DMSO-$d_6$); 0.90 (6H, s), 1.18 (9H, s), 1.22 (6H, d, J=6.75 Hz), 2.95 (3H, m), 3.35 (2H, s), 5.52 (2H, s), 6.25 (2H, s), 6.90 (2H, d, J=9 Hz), 6.95 (1H, dd, J= 1.5, 9 Hz), 7.23 (1H, d, J=9 Hz), 7.33 (2H, d, J=9 Hz), 7.47 (1H, d, 1.5 Hz), 9.28 (1H, s); MS (M+H)⁺=516. Analysis calc'd for $C_{28}H_{38}ClN_3O_2S$ (0.25 $H_2O$): C, 64.59; H, 7.45; N, 8.07; Found: C, 64.58; H, 7.45; N, 7.95.

EXAMPLE 4

Preparation of N'-hydroxy-N'methyl-N-2-[(1-(4-chlorophenylmethyl)-3-(1,1-dimethylethylthio)-5-(1-methylethyl))indol-2-yl]ethyl urea

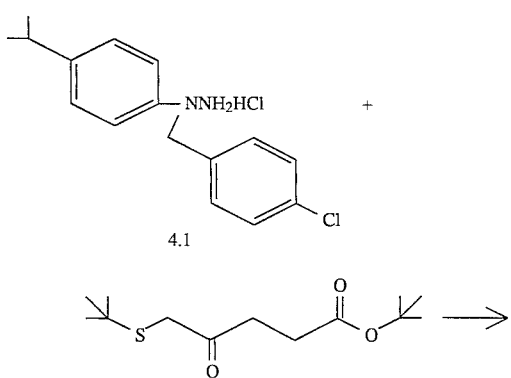

4.1

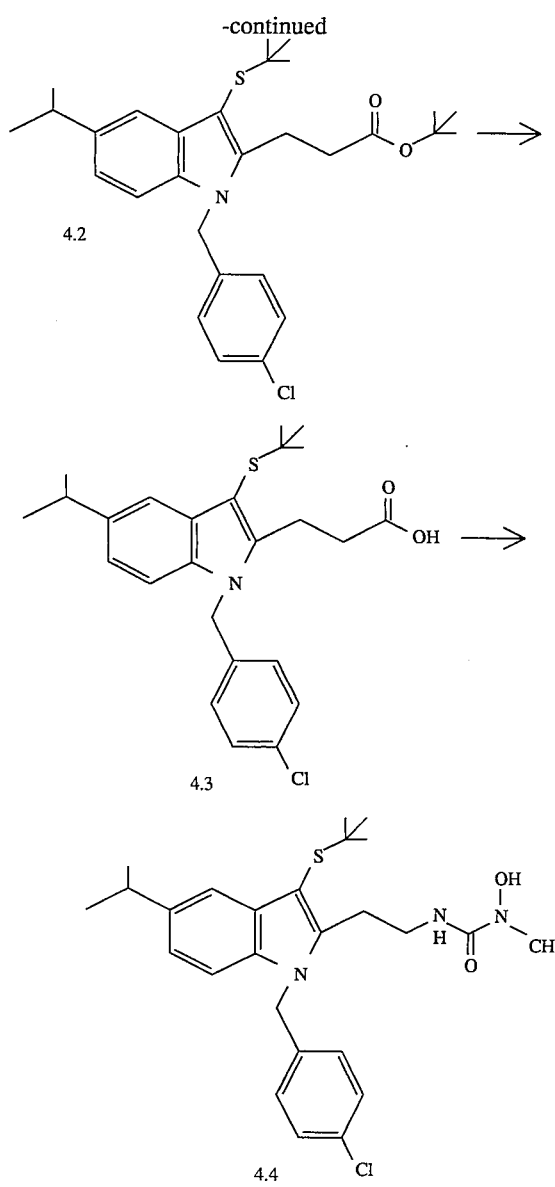

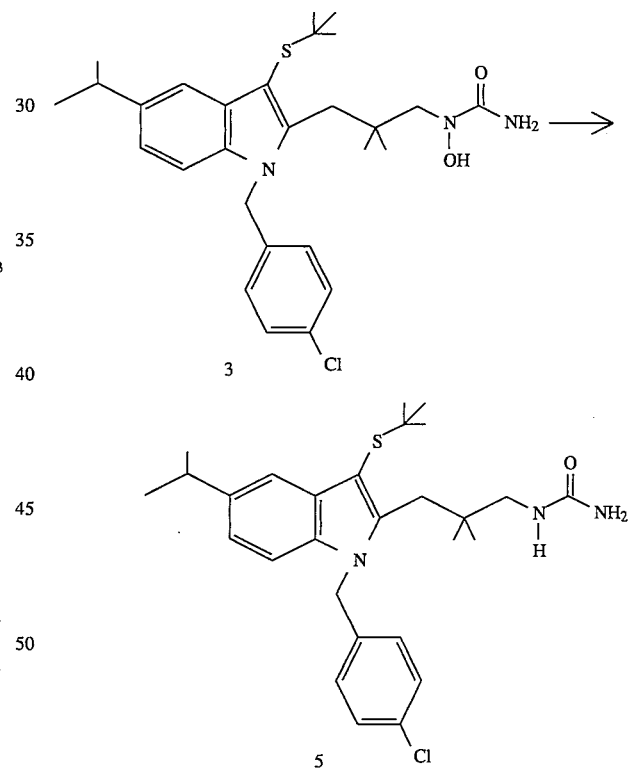

matography (silica gel, 5% EtOAc/hexane). Compound 4.2 (293 mg, 0.586 mmol) was stirred in $CH_2Cl_2$ (2.5 mL), TFA 0.45 mL (5.86 mmol), and anisole (0.13 mL, 1.17 mmol) overnight. After purification by chromatography (silica gel, EtOAc and 5–10% $MeOH/CHCl_3$), 187 mg of the acid intermediate 4.3 was obtained.

Starting with intermediate 4.3 (161 mg, 0.363 mmol) and following the procedure outlined in Example 1, 100 mg of desired product 4 was obtained as a white solid after purification by chromatography (silica gel, 50% EtOAc/ hexane). m.p. 87°–93° C.; $^1$H NMR (300 MHz, DMSO-$d_6$); 1.23 (6H, d, J=7.5 Hz), 1.28 (9H, s), 2.95 (4H, m), 3.08 (2H, m), 3.15 (2H, m), 5.62 (2H, s), 6.98 (3H, m), 7.20 (1H, d, J=8.25 Hz), 7.25 (1H, m), 7.37 (2H, m), 7.46 (1H, d, J=1.5 Hz), 9.33 (1H, m); MS $(M+H)^+$=488, $(M+NH_4)^+$=505. Analysis calc'd for $C_{26}H_{34}ClN_3O_2S$: C, 63.98; H, 7.02; N, 8.61; Found: C, 63.69; H, 7.13; N, 8.37.

EXAMPLE 5

Preparation of N-2,2-dimethyl-3-[(1-(4-chlorophenylmethyl)-3-(1,1-dimethylethyl-thio)-5-(1-methylethyl))indol-2-yl]propyl urea To a solution of diisopropylamine (11.5 mL, 81.1 mmol) in dry THF (175 mL) at 0° C., under $N_2$(g) atmosphere, n-BuLi (2.5M in hexanes) (31.0 mL, 77 mmol) was added over a fifteen minute interval. The reaction was stirred for 15 additional minutes at both 0° C. and −78° C.; t-butyl acetate (10.0 mL, 69.9 mmol) in dry THF (15 mL) was added dropwise over a 15 minute period. After stirring 45 minutes at −78° C., 2-chloro, 3-iodo-1-propene (15.8 g, 78 mmol) was added, and the reaction stirred for 15 minutes at −78° C. and 15 minutes at 0° C. before quenching with excess $NH_4Cl$ (sat'd, aq). The quenched reaction mixture was poured into a separatory funnel and extracted with EtOAc (2×). The combined organic layers were washed (10% aq HCl, $H_2O$, and brine), dried ($MgSO_4$), and concentrated in vacuo to yield 18.87 g of a dark red oil. 10.18 g of intermediate 4.1, as a pale red oil, was obtained after distillation (b.p. 79.5°–83° C.).

Starting with Compound 4.1 (2.5 g, 13.11 mmol) and adapting the procedure reported in EPA 8731103 1.6 used in Example 1, 1.09 g of the Fischer-Indole product 4.2, was obtained as a yellow waxy solid after purification by chro- A stirring solution of 3 (632 mg, 1.22 mmol) in methanol (10 mL), under $N_2$(g) atmosphere, was warmed to 45° C. ( $H_2O$ bath). To this solution was added NaOAc×3$H_2O$ (2.0 g, 14.64 mmol) in $H_2O$ (3 mL). After stirring a few minutes the reaction became homogeneous, and 3.1 mL of a 1.2 M $TiCl_3$ aqueous was added dropwise over a few minutes. After stirring 24 hours, the reaction was partially concentrated in vacuo. The resultant concentrate was poured into 50% aq NaCl (100 mL) and extracted carefully with a 2/1 THF/ethyl acetate (2×100 mL) solution. The organic extracts were combined, washed (sat'd, aq $NaHCO_3$ and brine), dried (MgSO₄), concentrated in vacuo, and purified by chromatography (silica gel, 5% MeOH/CH₂Cl₂) to yield 350 mg of desired product 5 as a white amorphous solid. m.p. 109°–112° C.; ¹H NMR (300 MHz, DMSO-d₆); 0.82 (6H, s), 1.20 (9H, s), 1.23 (6H, d, 6.75 Hz), 2.83–2.98 (5H, m), 5.43 (2H, s), 5.52 (2H, s), 6.06 (1H, br t, J=6 Hz), 6.88 (2H, d, J=8.25 Hz), 6.97 (1H, dd, J=8.25, 1.5 Hz), 7.24 (1H, d, J=8.25 Hz), 7.32 (2H, d, J=8.25 Hz), 7.47 (1H, d, J=1.5 Hz); MS (M+H)⁺=500. Analysis calc'd for $C_{28}H_{38}ClN_3OS$: C, 67.24; H, 7.66; N, 8.40; Found: C, 67.11; H, 7.74; N, 8.25.

EXAMPLE 6

Preparation of N'-hydroxy-N'-methyl-N-2-[3-(1-(4-chlorophenylmethyl)-3-(1,1-dimethylethylthio)-5-(1-methylethyl)indol-2-yl)-2,2-dimethylpropionylamino]ethyl urea

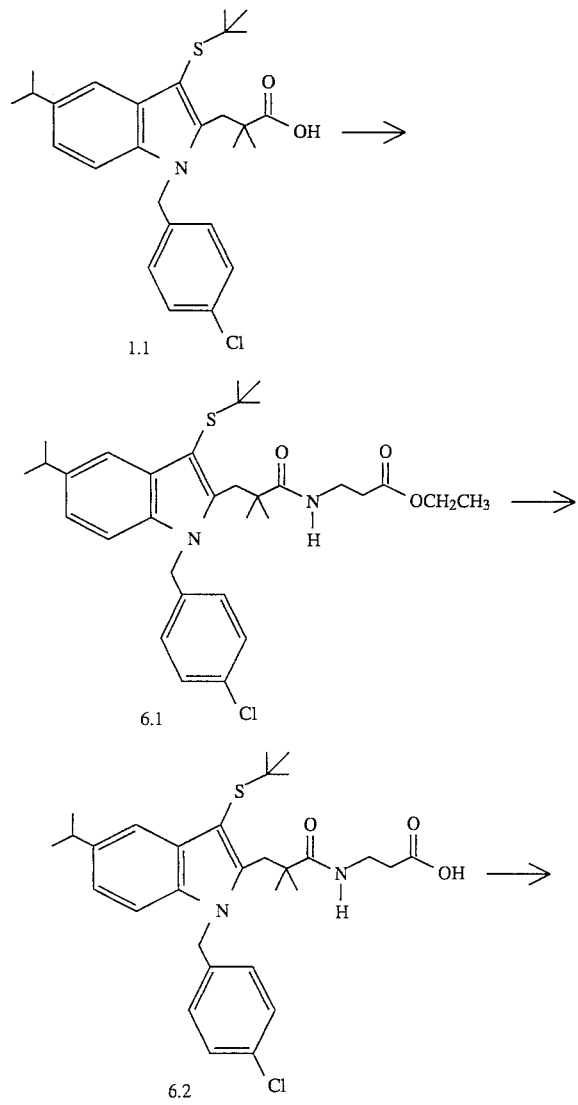

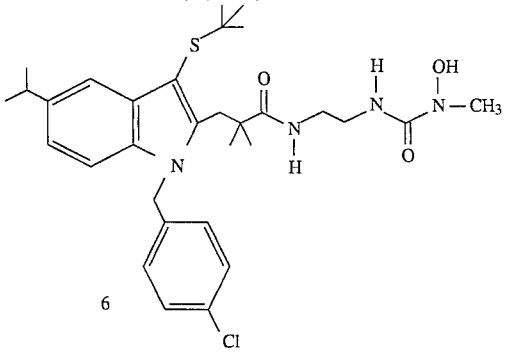

The following reactants were combined in a round-bottom flask: Compound 1.1 (8.0 g, 16.9 mmol), β-alanine ethyl ester hydrochloride (2.65 g, 16.9 mmol), and 1-hydroxybenztriazole hydrate (6.85 g, 50.7 mmol). The vessel was placed under N₂(g) atmosphere; DMF (43 mL) and N-methyl morpholine (3.70 mL, 33.8 mmol) were then added. The reaction was cooled to −23° C. (CCl₄/CO₂ bath) and stirred ten minutes before adding 1-ethyl-3-(3-aminomethyl) carbodiimide hydrochloride (3.24 g, 16.9 mmol). The reaction was allowed to slowly warm to room temperature and stir overnight. The reaction mixture was poured into NaHCO₃ (200 mL) (aq, sat'd) and extracted with EtOAc (2×500 mL). The combined organic extracts were washed (4×H₂O, 3×brine), dried (MgSO₄), concentrated in vacuo, and purified by chromatography (silica gel, 20–35% EtOAc/hexane) to yield 8.83 g of intermediate ester 6.1. m.p. 45°–50° C.; ¹H NMR (300 MHz, DMSO-d₆); 1.08 (6H, s), 1.14 (3H, t, J=6.75 Hz), 1.19 (9H, s), 1.23 (6H, d, J=6.75 Hz), 2.42 (2H, t, J=7.50 Hz), 2.95 (1H, septet, J= 6.75 Hz), 3.15 (2H, s), 3.22–3.32 (2H, m), 4.0 (2H, quartet, J=6.75 Hz), 5.45 (2H, s), 6.86 (2H, d, J=8.25 Hz), 6.97 (1H, dd, J=8.25, 1.5 Hz), 7.24 (1H, d, 8.25 Hz), 7.32 (2H, d, J=8.25 Hz), 7.47 (1H, d, 1.5 Hz), 7.58 (1H, br t, J=5.25 Hz); MS (M+H)⁺=571.

To a stirring solution of ester 6.1 (7.31 g, 12.8 mmol) in THF (40 mL), LiOH (880 mg, 21.0 mmol) in H₂O (23 mL) was added. The reaction was stirred for four hours then acidified with HCl (12M). The aqueous solution was extracted with EtOAc (2×300 mL). The combined aqueous extracts were dried (MgSO₄), concentrated in vacuo and purified by chromatography (silica gel, 20–50% EtOAc/hexane/2%HOAc) to yield 6.80 g of acid 6.2 as a white, amorphous solid. m.p. 80.3°–83.0° C.; ¹H NMR (300 MHz, DMSO-d₆); 1.08 (6H, s), 1.20 (9H, s), 1.23 (6H, d, J=6.75 Hz), 2.36 (2H, t, J=7.50 Hz), 2.95 (1H, septet, J= 6.75 Hz), 3.17 (2H, s), 3.20–3.30 (2H, m), 5.45 (2H, s), 6.87 (2H, d, J= 8.25 Hz), 6.97 (1H, dd, J=1.5 Hz, 8.25 Hz), 7.24 (1H, d, J=8.25 Hz), 7.32 (2H, d, J= 8.25 Hz), 7.47 (1H, d, J=1.5 Hz), 7.57 (1H, br t, J=5.25 Hz); MS (M+H)⁺=543.

Starting with acid intermediate 6.2 (746 rag, 1.37 mmol) and following the procedure of Example 1 listed above, 315 mg of desired product 6 was obtained as a white, amorphous solid. m.p. 99.3°–105° C.; ¹H NMR (300 MHz, DMSO-d₆); 1.08 (6H, s), 1.20 (9H, s), 1.23 (6H, d, J=7.5 Hz), 2.88–3.00 (4H, m), 3.05– 3.15 (4H, m), 3.17 (2H, s), 5.43 (2H, s), 6.87 (2H, d, J=8.25 Hz), 6.98 (1H) dd, J=1.5, 8.25 Hz), 7.05 (1H, m), 7.25 (1H, d, J=8.25 Hz), 7.32 (2H, d, J= 8.25 Hz), 7.47

(1H, d, J=1.5 Hz), 7.59 (1H, m), 9.32 (1H, s); MS (M+H)+ =587. Analysis calc'd for $C_{31}H_{43}ClN_4O_3S(0.5\ H_2O)$: C, 62.45; H, 7.44; N, 9.40; Found: C, 62.71; H, 7.33; N, 9.38.

EXAMPLE 7

Preparation of 1-(4-chlorophenylmethyl)-2-[2,2-dimethyl-3-((3-hydroxypropyl)amino)propyl]-3-(1,1-dimethylethylthio)-5-(1-methylethyl)indole

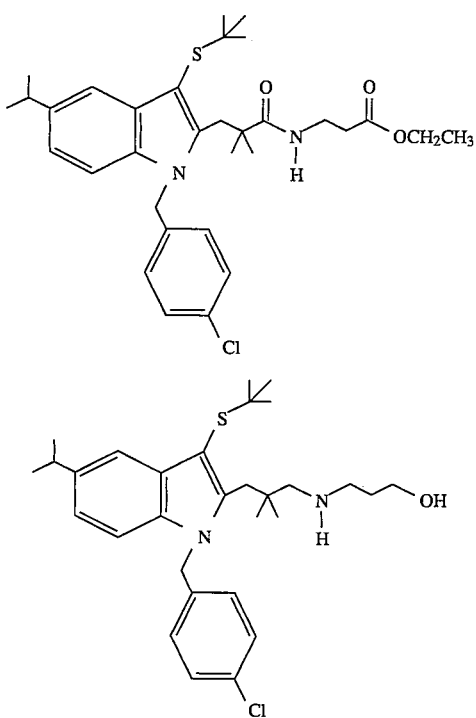

To a stirring solution, under $N_2$ (g) atmosphere, of ester 6.1 (964 mg, 1.69 mmol) in $Et_2O$ (4 mL) and THF (10 mL), 1.0M LAH (ether) solution (3.38 mL, 3.38 mmol with respect to aluminum) was added dropwise over a 90 second period. After stirring 3 hours, the reaction mixture was quenched with $H_2O$ (0.2 mL), 15% aqueous NaOH (0.2 mL), and $H_2O$ (0.6 mL). The resulting aluminum salts were filtered off through a celite pad with EtOAc (200 mL). The filtrate was concentrated in vacuo and purified by chromatography (silica gel, 10–35% EtOAc/hexane/2%isopropylamine) to yield 680 mg of desired product 7 as a clear, colorless oil. $^1$H NMR (300 MHz, DMSO-$d_6$); 0.87 (6H, s), 1.20 (9H, s), 1.23 (6H, d, J=7.5 Hz), 1.55–1.64 (3H, m), 2.27 (2H, br s), 2.58 (2H, br t, Hz), 2.90–3.00 (3H, m), 3.48 (2H, t, J=6.0 Hz), 4.50 (1H, br s), 5.65 (2H, br s), 6.87 (2H, d, J=8.25 Hz), 6.95 (1H, dd, J=1.5, 8.25 Hz), 7.23 (1H, d, J=8.25 Hz), 7.32 (2H, d, J=8.25 Hz), 7.47 (1H, d, J=1.5 Hz); MS (M+H)+=515. Analysis calc'd for $C_{30}H_{43}ClN_2OS$: C, 69.94; H, 8.41; N, 5.44; Found: C, 70.56; H, 8.57; N, 5.49.

EXAMPLE 8

Preparation of N-2-[2-methyl-3-(1-(4-chlorophenylmethyl)-3-(1,1-dimethylethylthio)-5-(1-methylethyl)indol-2-yl)]propyl urea

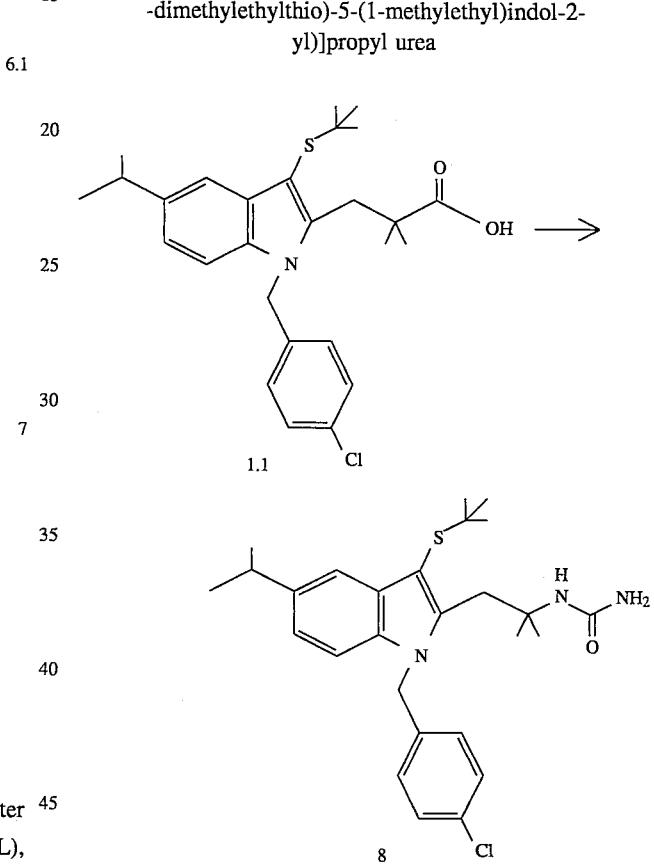

Starting with Compound 1.1 (1.00 g, 2.12 mmol) and 14.8 N ammonium hydroxide (0.90 g, 2.23 mmol) and following the procedure outlined in Example 1, 344 mg of desired product 8 was obtained as white, powdery solid after recrystallization ($Et_2O/CH_2Cl_2$/hexane). m.p. 206.1°–206.5° C.; $^1$H NMR (300 MHz, DMSO-$d_6$); 1.18 (15H, s), 1.23 (6H, d, J=6.75 Hz), 2.95 (1H, septet, J= 6.75 Hz), 3.4 (2H, s), 5.41 (2H, s), 5.58 (2H, s), 5.92 (1H, s), 6.90 (2H, d, J=8.25 Hz), 6.97 (1H, dd, J=1.5 and 8.25 Hz), 7.28–7.35 (3H, m), 7.46 (1H, d, J=1.5 Hz); MS (M)+=485. Analysis calc'd for $C_{27}H_{36}ClN_3OS$: C, 66.71; H, 7.46; N, 8.64; Found: C, 66.89; H, 7.51; N. 8.59.

EXAMPLE 9

Preparation of 3-[3-(1-(4-chlorophenylmethyl)-3-(1,1-dimethylethylthio)-5-(1-methylethyl)indol-2-yl)-2-aminocarbonylamino-2-methylpropyl]propanoic acid, ethyl ester

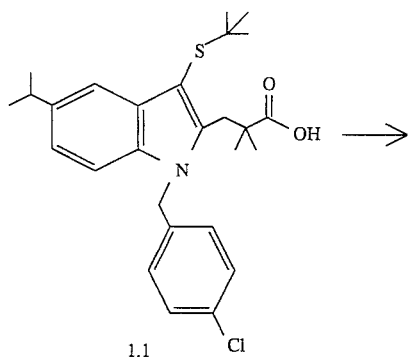
1.1

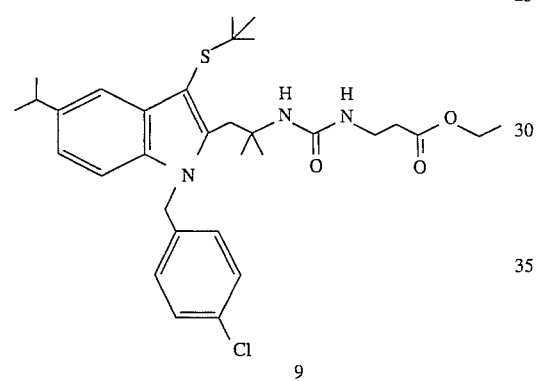
9

Starting with Compound 1.1 (1.34 g, 2.84 mmol) and β-alanine ethyl ester hydrochloride (445 mg, 2.84 mmol) and following the procedure outlined in Example 1, 1.28 g of Compound 9 was obtained as a white, amorphous solid after purification by chromatography (silica gel, 30% EtOAc/hexane). m.p. 131° C.; $^1$H NMR (300 MHz, DMSO-$d_6$); 1.18–1.21 (18 H, m), 1.23 (6H, d, J= 6.9 Hz), 2.42 (2H, t, J=6.7 Hz), 2.95 (1H, septet, J=7.5 Hz), 3.23 (2H, quartet, J=6.0 Hz), 3.38 (2H, br s), 4.08 (2H, quartet, J=7.2 Hz), 5.52 (2H, s), 5.83 (1 H, t, J=6.25 Hz), 5.87 (1H, s), 6.89 (2H, d, J=8.6 Hz), 6.97 (1H, dd, J=1.5 and 8.4 Hz), 7.22 (1H, d, J=8.2 Hz), 7.32 (2H, d, J=8.4 Hz), 7.46 (1H, d, J=1.7 Hz); MS (M+H)$^+$=586. Analysis calc'd for $C_{32}H_{44}ClN_3O_3S$: C, 65.56; H, 7.56; N, 7.17; Found: C, 65.76; H, 7.65; N, 7.12.

EXAMPLE 10

Preparation of 3-[3-(1-(4-chlorophenylmethyl)-3-(1,1-dimethylethylthio)-5-(1-methylethyl)indol-2-yl)-2-aminocarbonylamino-2-methylpropyl]propanoic acid

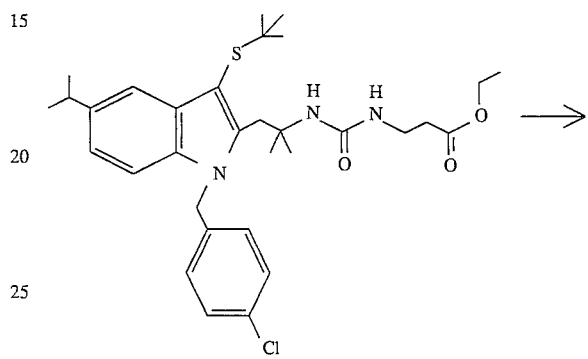
9

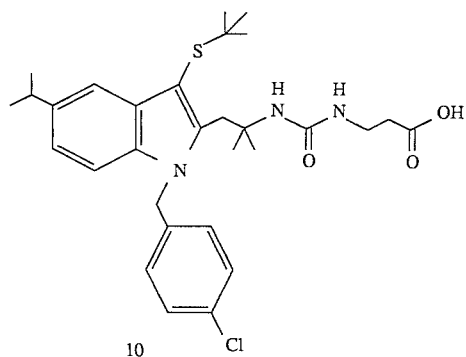
10

Starting with Compound 9 (1.00 g, 1.71 mmol) and following the procedure outlined in Example 6, 930 mg of desired product 10 was obtained as white, amorphous solid after purification by chromatography (silica gel, 15–50%EtOAc/2%HOAc/hexane). m.p. 139°–141° C.; $^1$H NMR (300 MHz, DMSO-$d_6$); 1.18 (15H, s), 1.23 (6H, d, J=6.9 Hz), 2.36 (2H, t, J=6.5 Hz), 2.95 (1H, septet, J -6.9 Hz), 3.20 (2H, quartet, J=6.0 Hz), 3.37 (2H, br s), 5.52 (2H, s), 5.83 (1H, t, J -6.25 Hz), 5.89 (1H, s), 6.88 (2H, d, J= 8.6 Hz), 6.97 (1H, dd, J=1.7 and 8.6 Hz), 7.22 (1H, d, J=8.2 Hz), 7.32 (2H, d, J=8.2 Hz), 7.46 (1H, J=1.7 Hz); MS (M+H)$^+$ =558/560. Analysis calc'd for $C_{30}H_{40}ClN_3O_3S$: C, 62.54; H, 7.35; N, 7.29; Found: C, 62.56; H, 7.12; N, 6.97.

EXAMPLE 11

Preparation of
N'-hydroxy-N'-methyl-N-'[1-(4-chlorophenylmethyl)-5-(1-methylethyl)-2-((2-methyl-2-ethoxycarbonyl)propyl)indol-2-yl]-3-oxopropylurea

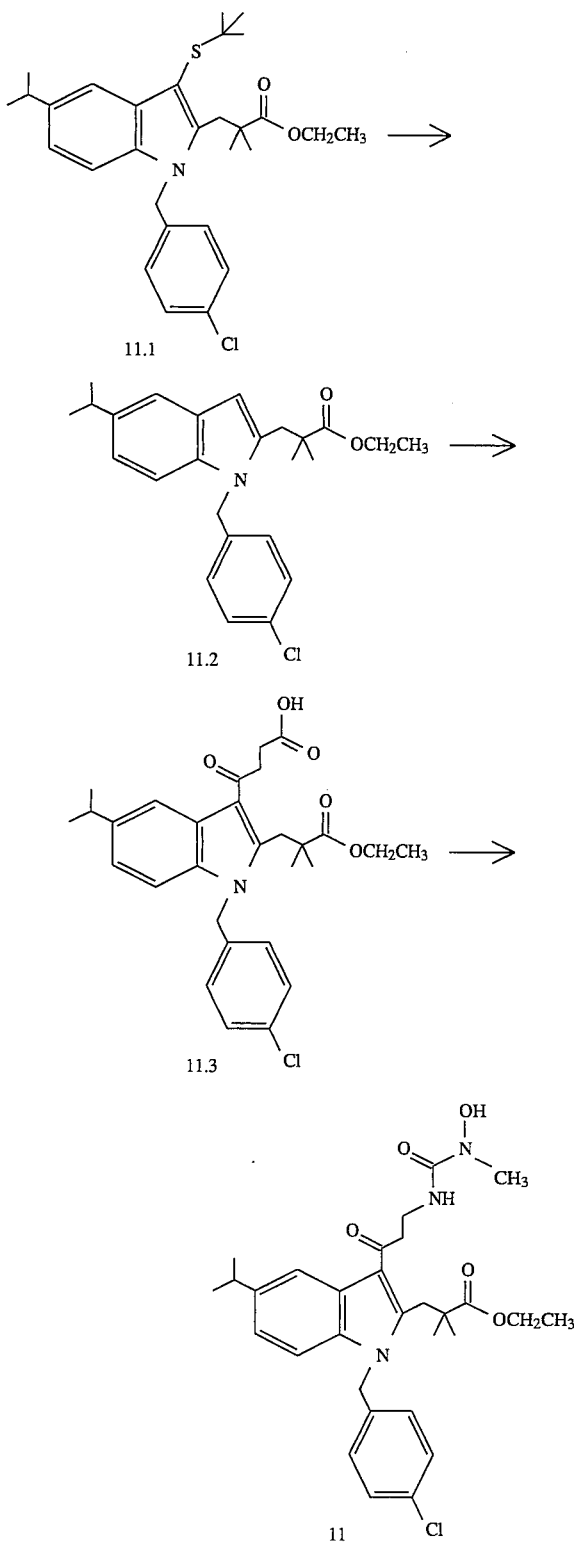

Starting with Compound 11.1 (3.60 g, 7.20 mmol), the ethyl ester of Compound 1.1, in benzene (70 mL), AlCl$_3$ (2.88 g, 21.6 mmol) was added neat. The reaction was stirred for one hour, under N$_2$(g) atmosphere. The brown reaction mixture was poured into a separatory funnel containing 10% aqueous HCl and extracted with EtOAc. The combined organic extracts were washed (2×H$_2$O and 1×brine), dried (MgSO$_4$), and concentrated in vacuo to yield 3.63 g of a dark orange syrup. After purification by chromatography (silica gel, 10–20% Et$_2$O/hexane), 1.68 g of Compound 11.2 was obtained as a viscous oil.

To a stirring solution, under N$_2$ (g) atmosphere, of Compound 11.2 (1.68 g, 4.08 mmol) in distilled CH$_2$Cl$_2$ (35 mL), succinic anhydride (410 mg, 4.10 mmol) was added neat. The reaction was cooled to 0° C., and AlCl$_3$ (1.25 g, 9.40 mmol) added via a powder addition funnel (over a three minute interval). After stirring overnight at room temperature, the reaction mixture was poured into dilute aqueous HCl and extracted with EtOAc. The combined organic extracts were washed (1×brine), dried (MgSO$_4$), and concentrated in vacuo. The crude concentrate was purified by chromatography (silica gel, 20% EtOAc/2%HOAc/hexane), followed by recrystallization (CH$_2$Cl$_2$/hexane) to yield 535 mg of Compound 11.3 as a fine white solid. m.p. 172.5°–174° C..

Starting with Compound 11.3 (385 mg, 0.752 mmol) and following the procedure outlined in Example 1, 30 mg of Compound 11 as a salmon-colored solid was obtained after purification by chromatography (silica gel, 20–50% EtOAc/hexane/2%HOAc) and recrystallization (EtOAc/hexane). m.p. 150.5°– 152° C.; $^1$H NMR (300 MHz, DMSO-d$_6$); 1.10 (3H, t, J=6.75 Hz), 1.16 (9H, s), 1.25 (6H, d, J=6.75 Hz), 2.95 (3H, s), 3.02 (1H, septet, J=6.75 Hz), 3.23 ( 2H, t, J=6.75 Hz), 3.45 (2H, quartet, J=6.0 Hz), 3.58 (2H, s), 4.0 (2H, quartet, J= 6.75 Hz), 5.50 (2H, br s), 6.92 (3H, m), 7.08 (1H, dd, J=1.5 and 8.25 Hz), 7.32 (1H, d, J=8.25 Hz), 7.35 (2H, d, J=8.25 Hz), 7.76 (1H, br s), 9.39 (1H, s); MS (M+H)$^+$=556. Analysis calc'd for C$_{30}$H$_{38}$ClN$_3$OS(0.25 H$_2$O): C, 64.28; H, 6.92; N, 7.50; Found: C, 64.33; H, 6.86; N, 7.35.

EXAMPLE 12

Preparation of
1-(4-chlorophenylmethyl)-3-(1,1-dimethylethylthio)-
2-[3-(2,2-dimethyl-
1-guanidinylimino)propyl]-(1-methylethyl)indole

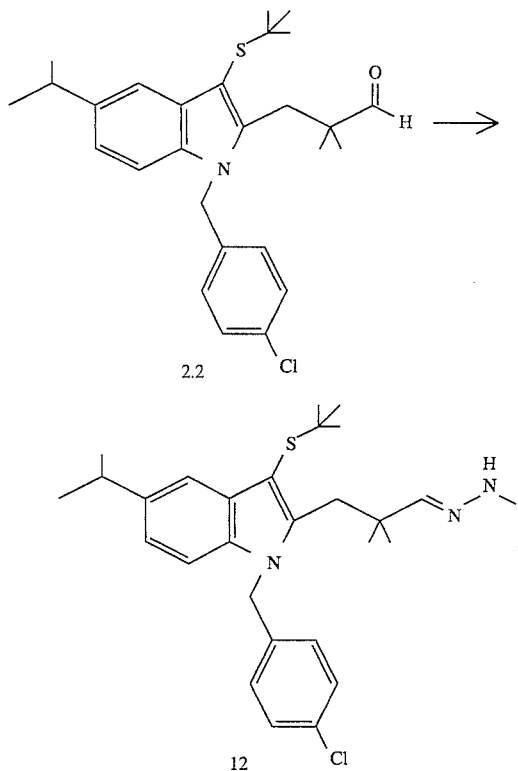

Compound 2.2 (676 mg, 1.48 mmol) was suspended in EtOH (3 mL) and stirred under $N_2(g)$ atmosphere. Aminoguanadinium hydrogen carbonate (205 mg, 1.50 mmol) was suspended in MeOH (3 mL) and 6N HCl aqueous added until all of the solid dissolved. The aminoguanidinium solution was added to the solution of Compound 2.2, and the reaction allowed to stir 16 hours. The reaction was concentrated in vacuo and purified by chromatography (silica gel, 5.5% MeOH/2% isopropylamine/$CHCl_3$) to yield 374 mg of Compound 12 as a cream-colored amorphous solid. m.p. 105°–107° C.; $^1H$ NMR (300 MHz, DMSO-$d_6$); 1.07 (6H, s), 1.20 (9H, s), 1.22 (6H, d, J=6.75 Hz), 2.95 (1H, septet, J=6.75 Hz), 3.05 (2H, br s), 5.22 (2H, br s), 5.40 (2H, s), 5.51 (2H, br s), 6.85 (2H, d, J=8.25 Hz), 6.97 (1H, dd, J=8.25 and 1.5 Hz), 7.27 (1H, d, J=8.25 Hz), 7.32 ( 3H), m), 7.46 (1H, d, J=1.5 Hz); MS $(M+H)^+$=512/514. Analysis calc'd for $C_{28}H_{38}ClN_5S(0.25\ H_2O)$: C, 65.09; H, 7.51; N, 13.67; Found: C, 64.97; H, 7.51; N, 13.47.

EXAMPLE 13

Preparation of
3-[3-(1-(4-chlorophenylmethyl)-3-(1,1dimethylethylthio)-5
-(1-methylethyl)indol-2-yl)-2-aminocarbonylamino-2-
methylpropyl]propanoic acid, sodium salt

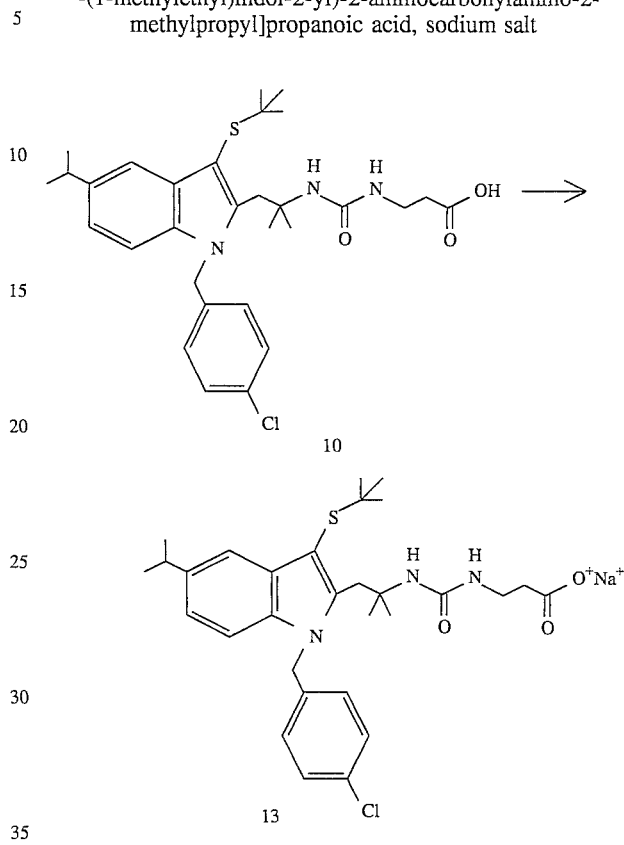

To a stirring THF (2 mL) solution of Compound 10 (314 mg, 0.563 mmol), NaOMe (30.4 mg, 0.563 mmol) was added and the reaction stirred at room temperature. The reaction was carried out under $N_2(g)$ atmosphere. After one hour the reaction was taken up in 50% EtOAc/THF, washed (2×brine), dried ($MgSO_4$), and purified by chromatography (silica gel, 5% MeOH/$CH_2C_2$) to yield 236 mg of Compound 13 as an off-white amorphous solid. m.p. 176°– 185° C.; $^1H$ NMR (300 MHz, DMSO-$d_6$); 1.18 (15H, s), 1.22 (6H, d, J=6.75 Hz), 2.26 (2H, t, J=6.0 Hz), 2.95 (1 H, septet, J=6.75 Hz), 3.17 (2H, m), 3.38 (2H, br s), 5.53 (2H, br s), 5.88 (1 H. br s), 6.0 (1H, br s), 6.89 (2H, d, J=8.2 Hz), 6.96 (1H, dd, J=8.25 and 1.5 Hz), 7.23 (1H, d, J=8.25 Hz), 7.32 (2H, d, J= 8.25 Hz), 7.46 (1H, d, J=1.5 Hz); MS $(M+H)^+$= 580 and (M+Na)=602. Analysis calc'd for $C_{30}H_{39}ClN_3O_3$: C, 62.12; H, 6.78; N, 7.24; Found: C, 62.21; H, 6.78; N, 7.34.

EXAMPLE 14

Preparation of
N-hydroxy-N-[trans-2-(1-(4-chlorophenylmethyl)-3-(1,1
-dimethylethylthio)-5-(1
-methylethyl)indol-2-yl)cyclopropyl]methylurea

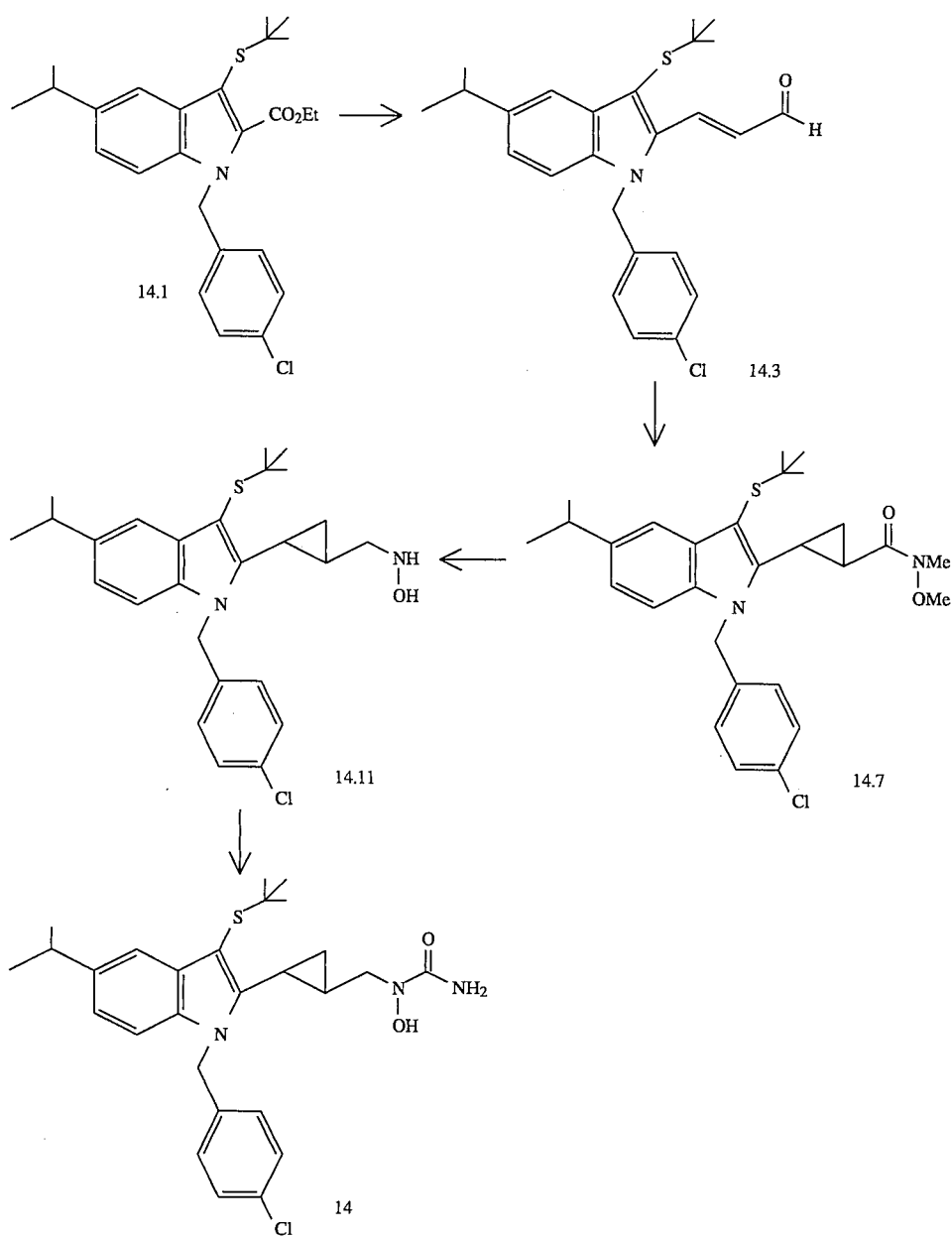

To a solution of ethyl bromopyruvate (10.00 g, 51.3 mmol) in THF (250 mL) at 0° C., was added 2-methyl-2-propanethiol (4.86 g, 53.87 mmol) followed by the dropwise addition of triethylamine (6.22 g, 61.56 mmol). The cooling bath was removed and the reaction allowed to come to rt and stir for 15 h. The reaction was then diluted with brine (250 mL) and extracted with ethyl acetate (3×250 mL). The organics were combined, dried with MgSO₄ and concentrated. Vacuum distillation of the resulting residue (0.7 mm Hg) afforded 6.47 g (62%) of distillation of the resulting residue (0.7 mm Hg) afforded 6.47 g (62%) of ethyl t-butylthiopyruvate as a colorless oil (b.p. 89°–92° C.) which was used immediately.

To a solution of ethyl t-butylpyruvate (6.46 g, 31.7 mmol) in toluene (120 mL) was added N-(4-isopropylphenyl)-N-(4-chlorobenzyl)-hydrazine (11.43 g, 36.7 mmol), sodium acetate (3.30 g, 40.26 mmol) and acetic acid (60 mL). The reaction was stirred for 24 h in the dark. It was then diluted with brine (200 mL) and extracted with ethyl acetate (3×200 mL). The organics were combined, dried with MgSO₄ and concentrated. The resulting residue was chromatographed (silica gel, ether:hexanes, 2:98) to afford 7.53 g (46%) of intermediate 14.1.

To a solution of intermediate 14.1 (7.51 g, 16.91 mmol) in toluene (25 mL) at −78° C., was added diisobutylaluminum hydride (50.73 mL of a 1.0M solution in hexanes, 50.73 mmol) dropwise. Upon completion of addition, the reaction was stirred for 30 min at −78° C. It was then quenched with aqueous 10% HCl (75 mL) and warmed to rt and extracted with ethyl acetate (3×75 mL). The organics were combined, dried with MgSO₄ and concentrated. The unpurified residue was taken up in CH₂Cl₂ (80 mL) and pyridinium dichromate (9.54 g, 25.37 mmol) was added. The reaction was stirred for 15 h, then filtered through Celite. The filtrate was concentrated. The resulting residue was chromatographed (silica gel, ether:hexanes, 3:97) to afford 4.16 g (61% over the two steps) of intermediate 14.2 as an off-white solid.

A solution of intermediate 14.2 (4.15 g, 10.4 mmol) and malonic acid (1.40 g, 13.5 mmol) in pyridine (5 mL) containing piperidine (177 mg, 2.08 mmol) was refluxed for 18 h. It was then cooled to rt and poured into ice/conc. HCl (50 mL). This aqueous solution was then extracted with ethyl acetate (3×50 mL). The organics were combined, dried with MgSO$_4$ and concentrated. The resulting residue was chromatographed (silica gel, ether:hexanes:acetic acid, 30:69:1 ) to afford 1.06 g (23%) of intermediate 14.3 as a gold foam.

To a solution of intermediate 14.3 (1.05 g, 2.4 mmol) in CH$_2$Cl$_2$ (10 mL) was added oxalyl chloride (362 mg, 2.9 mmol) followed by a drop of N,N-dimethylformamide. The reaction was stirred for 1 hr, then concentrated. The resulting residue was taken up in CH$_2$Cl$_2$ (10 mL) and cooled to 0° C. N,O-Dimethylhydroxylamine hydrochloride (283 mg, 2.9 mmol) was added followed by pyridine (456 mg, 5.76 mmol). The cooling bath was withdrawn and the reaction allowed to warm to rt, diluted with brine (10 mL), and the layers were separated. The aqueous layer was extracted with CH$_2$Cl$_2$ (2×10 mL). The organics were combined, dried with MgSO$_4$ and concentrated. The resulting residue was chromatographed (silica gel, ether:hexanes, 1:1 ) to afford 1.04 g (89%) of intermediate 14.4 as a brown oil.

To a suspension of trimethylsulfoxonium iodide (514 mg, 2.3 mmol) in DMSO (5 mL) was added sodium hydride (57 mg of 97% dry, 2.3 mmol) and the resulting mixture was stirred for 20 min. Intermediate 14.4 (1.03 g, 2.1 mmol) was then added dropwise as a solution in DMSO (5 mL) and the reaction was stirred for 2 h at rt then brought to 50° C. for 18 h. It was then cooled to rt and diluted with brine (15 mL). This aqueous solution was extracted with ethyl acetate (3×20 mL). The organics were combined, dried with MgSO$_4$ and concentrated. The resulting residue was chromatographed (silica gel, ether:hexanes, 25:75) to afford intermediate 972 mg (93%) of intermediate 14.7 as a colorless oil.

To a solution of intermediate 14.7 (962 mg, 1.93 mmol) in THF (9 mL) at 0° C., was added diisobutylaluminum hydride (2.02 mL of a 1.0M solution in hexanes, 2.02 mmol) dropwise. Upon complete addition, the reaction was stirred for 30 min. It was then diluted with 10% aqueous HCl (10 mL) and extracted with ethyl acetate (3×10 mL). The organics were combined, dried with MgSO$_4$ and concentrated. The resulting residue was chromatographed (silica gel, ether:hexanes, 15:85) to afford 349 mg (41%) of intermediate 14.8 along with 372 mg (44%) of intermediate 14.9. Intermediate 14.9 (362 mg, 0.819 mmol) was recycled to intermediate 14.8 (218 mg, 61%) following the oxidation procedure described for the conversion of 2.1 to 2.2.

A solution of intermediate 14.8 (567 mg, 1.29 mmol) in 1:1 ethanol:pyridine (6 mL) was stirred for 18 h and concentrated. The resulting residue was taken up in brine (5 mL) and extracted with ethyl acetate (3×5 mL). The organics were combined, dried with MgSO$_4$ and concentrated to afford intermediate 14.10.

To a solution of intermediate 14.10 from above in ethanol (6 mL) was added borane-pyridine (264 mg, 2.84 mmol) and the mixture was stirred for 30 min. Aqueous 6N HCl (0.516 mL, 3.10 mmol) was added dropwise and the reaction was stirred for 1 hr. It was then neutralized by the addition of aqueous 2N NaOH, diluted with brine (5 mL) and extracted with ethyl acetate (3×10 mL). The organics were combined, dried with MgSO$_4$ and concentrated to afford intermediate 14.11.

To a solution of intermediate 14.11 in THF (6 mL) was added trimethylsilyl isocyanate (163 mg, 1.42 mmol) and the reaction was stirred for 10 rain and concentrated. The resulting residue was chromatographed (silica gel, ether:hexanes to ether:methanol, 70:30 to 90:10) to afford the desired material as a foam. $^1$H NMR (300MHz, DMSO-d$_6$): 0.98 (m, 1H), 1.22 (d, 6H), 1.24 (s, 9H), 1.31 (m, 1H), 1.62 (m, 1H), 1.72 (m, 1H), 2.95 (septet, 1H), 3.21 (m, 1 H), 7.24 (d, 1H, J=8.5 Hz), 7.35 (m, 2H), 7.46 (m, 1H), 9.30 (s, 1H); MS (M+H)$^+$=500; Analysis calc'd for C$_{27}$H$_{34}$ClN$_3$O$_2$S.¼H$_2$O: C, 64.27, H, 6.89, N, 8.33; Found: C, 64.26, H, 6.82, N, 7.92.

EXAMPLE 15

Preparation of
3-[3-(1,1-dimethylethylthio)-5-(1-methylethyl)-1-(4-pyridinylmethyl)indol-2-yl]-2,2-dimethylpropanoic acid

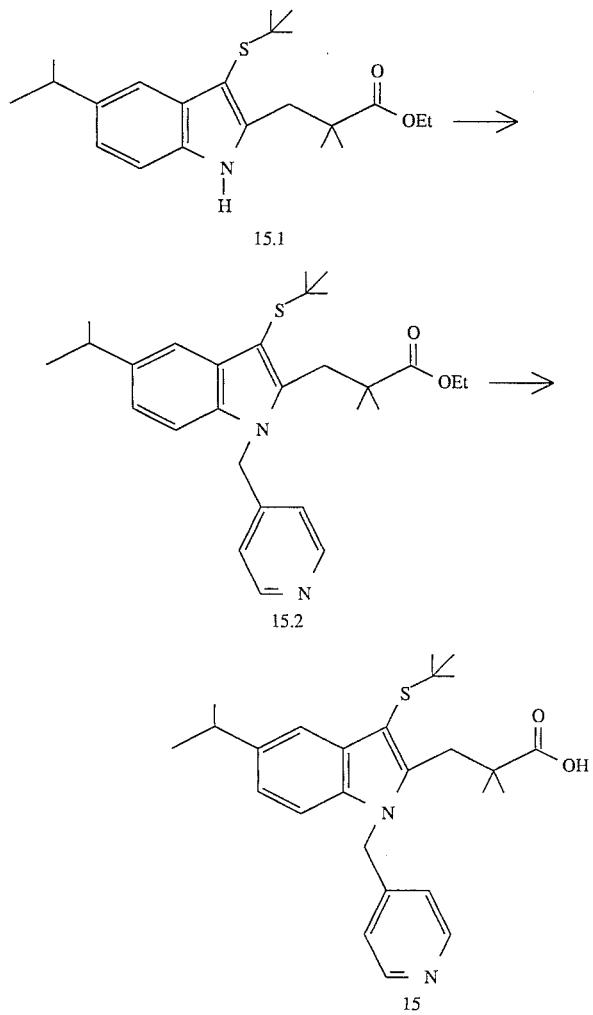

15

Compound 15.1 was prepared by adaptation of the procedure reported in EPA 87311031.6 using 4-isopropylphenyl hydrazine hydrochloride hydrate. To a –23° C. (CO₂(s)/CCl₄ bath) stirred THF (80 mL) solution of 4-pyridinemethanol (2.18 g, 20 mmol) under N₂(g) atmosphere, methanesulfonyl chloride (1.60 mL, 20 mmol) and triethylamine (2.88 mL, 20 6 mmol) were added neat and sequentially. The reaction was stirred at −23° C. one hour to give the corresponding mesylate. To a stirred DMSO (25 mL) solution of 15.1 (5.0 g, 13.3 mmol) under N₂(g) atmosphere, neat NaH (1.08 g, 35.9 mmol) was added. The above-formed mesylate was cannulated into the reaction mixture within 2 minutes of adding the NaH. The reaction was stirred for 120 minutes before it was quenched with sat'd aqueous NH₄Cl and extracted with EtOAc (2×200 mL) and 1/1 THF/EtOAc (1×100 mL). The combined organic extracts were washed (brine), dried (Na₂SO₄), and concentrated in vacuo to yield 1.24 g of compound 15.2 as a pale yellow solid.

15.2 (1.24 g, 2.66 mmol) was converted to 15 by adapting the procedure outlined in Example 1, to provide 0.60 g of 15 as a white, fibrous solid after recrystallization from CH₂Cl₂/EtOAc/hexane. m.p. 258 ° C.; $^1$H NMR (300 MHz, DMSO-d₆); 1.01 (6H, s), 1.18–1.27 (15H, m), 2.96 (1H, septet, J=6.75 Hz), 3.18 (2H, br s), 5.55 (2H, s), 6.77 (2H, d, J=6.75 Hz), 7.0 (1H, dd, J=8.25 and 1.5 Hz), 7.27 (1H, d, J=8.25 Hz), 7.50 (1H, d, J=1.5 Hz), 8.45 (2H, d, J=6.75 Hz), 12.45 (1H, br s). MS (M+H)⁺=439. Analysis calc'd for C₂₆H₃₄N₂O₂S(0.5 H₂O): C, 70.47; H, 7.85; N, 6.32; Found: C, 70.57; H, 7.82; N, 6.30.

EXAMPLE 16

Preparation of 3-[3-[(1,1-dimethylethylthio)-5-(1-methylethyl)-1-(2-thienylmethyl)indol-2-yl]-2,2-dimethylpropanoic acid

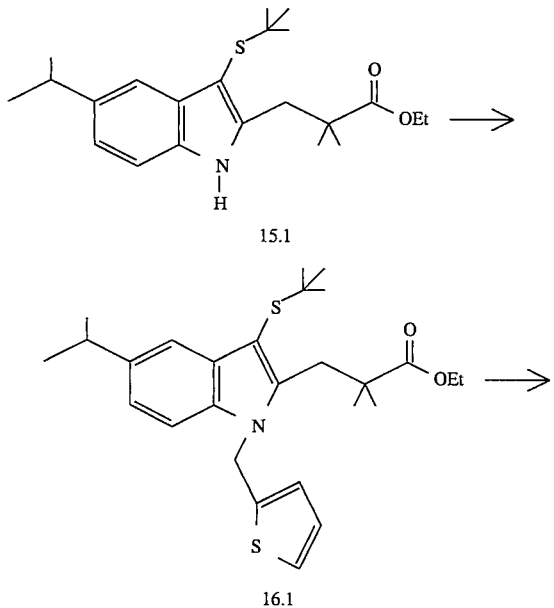

15.1

16.1

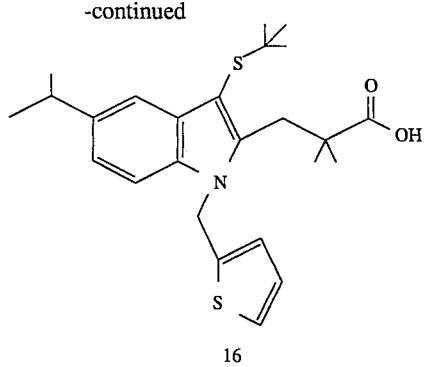

16

Compound 16 was prepared following the procedure described in Example 15 where 2-thiophenemethanol was substituted for 4-pyridinemethanol. Purification by flash chromatography (sg, 5–10% EtOAc/CCl₄/2% HOAc) afforded 1.95 g of Compound 16 as a pale yellow solid. m.p. 130.5°–132 ° C.; $^1$H NMR (300M Hz, DMSO-d₆); 1.12 (6H, s), 1.18 (9H, s), 1.23 (6H, d, J=7 Hz), 2.95 (1H, septet, J=7 Hz), 3.31 (2H, s), 5.65 (2H, s), 6.91 (1H, dd, J= 4 and 5 Hz), 6.97 (1H, dd, J=1.5 and 4 Hz), 7.02 (1H, dd, J=1.5 and 8.25 Hz), 7.33 (1H, dd, J=1.5 and 5 Hz), 7.42–7.48 (2H, m), 12.47 (1H, br s). MS (M+H)⁺=444 and (M+NH₄)⁺=461. Analysis calc'd for C₂₅H₃₃NO₂S₂: C, 67.68; H, 7.50; N, 3.16; Found: C, 67.45; H, 7.50; N, 3.10.

EXAMPLE 17

Preparation of N-hydroxy-N-trans-[3-(1-(4-chlorophenylmethyl)-3-(1,1-dimethylethylthio)-5-(1-methylethyl)indol-yl]prop-2-enylurea

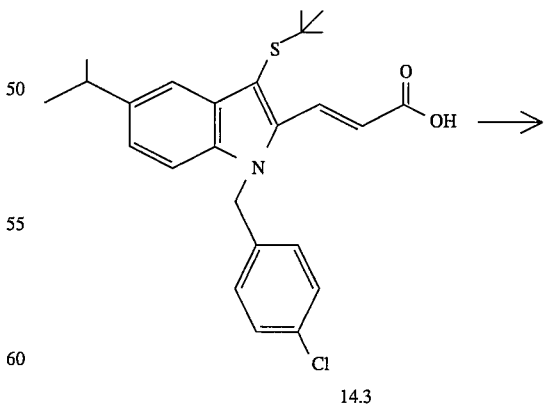

14.3

-continued

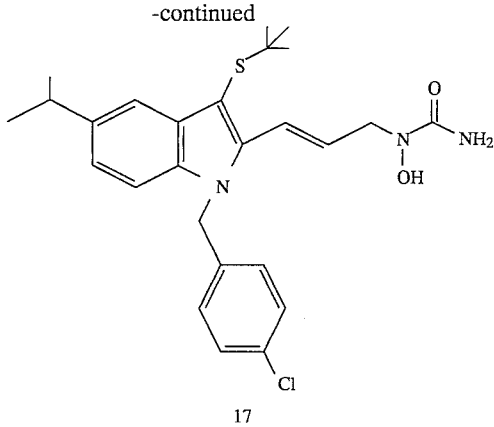

17

Compound 14.3 is converted to the corresponding oxime, 17.1, following the procedures described for the conversion of 1.1 to 2. Subsequently, 17.1 is converted into 17 following the procedures for the conversion of 2 into 3.

EXAMPLE 18

Preparation of N-[3-(1-(4-chlorophenylmethyl)-3-(1,1-dimethylethylthio)-5-(1-methylethyl)indol-2-yl)-2,2dimethyl-propyl]acetohydroxamic acid

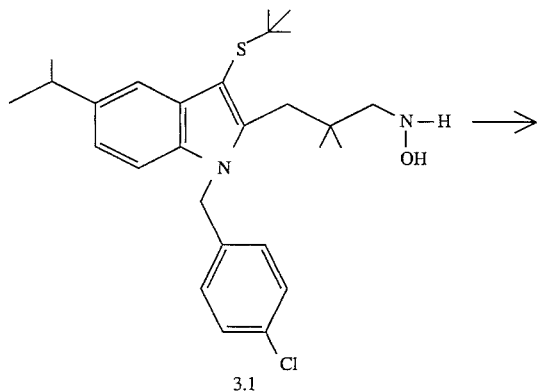

3.1

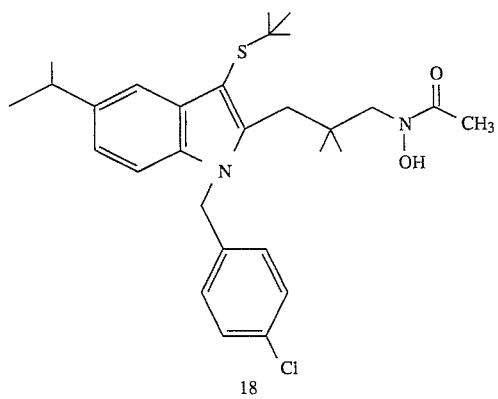

18

Hydroxylamine 3.1 is convened to 18 by treatment with acetyl chloride (2 equiv) and triethylamine to give the N,O-diacetate 18.1, which is O-deprotected by treatment with aqueous NaOH to provide 18.

EXAMPLE 19

Preparation of N-hydroxy-N-3-[3-(1-(4-chlorophenylmethyl)-3-(1,1-dimethylethylthio)-5-(1-methylethyl)indol-2-yl)-2,2-dimethylpropionylamino]propyl urea

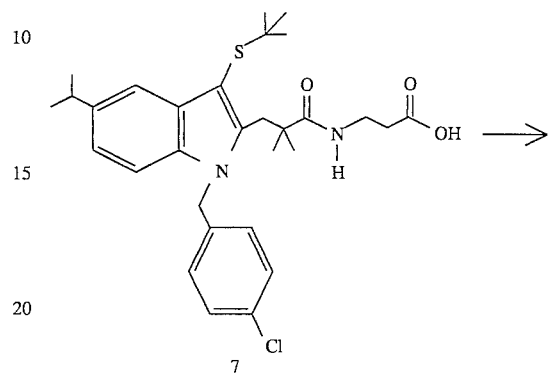

7

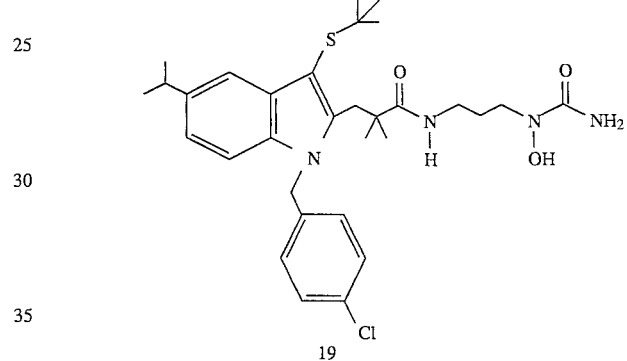

19

Compound 7 is reduced to the corresponding alcohol, 19.1, following the procedure employed for the conversion of 1.1 to 2.1, and is subsequently converted to 19 following the procedure employed to transform 15.3 into 15.

EXAMPLE 20

Preparation of 3-(4-chlorophenylmethyl)-3-(1,1-dimethylethylthio)-5-(1-methylethyl)indol-2-yl]-2,2-dimethylpropionaldehyde oxime-O-2-acetic acid

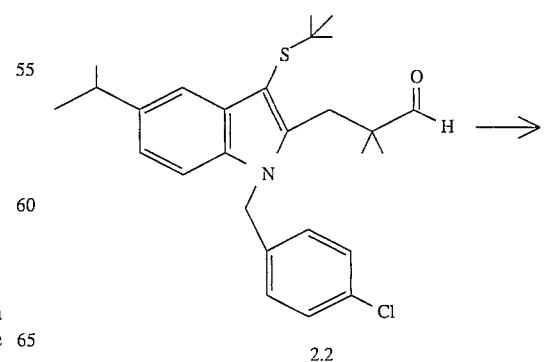

2.2

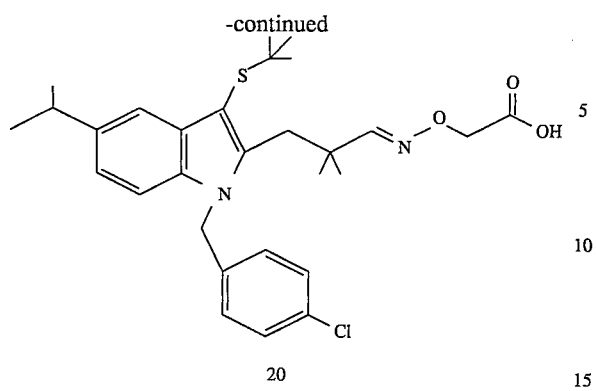

Compound 20 was prepared by following the procedure employed for the conversion of 2.2 to 2 where Carboxymethoxylamine hemihydrochloride was used in place of hydroxylamine hydrochloride. After purification by flash chromatography (silica gel, 20/75/5 EtOAc/Hexane/HOAc), 500 mg of a white-amorphous solid was obtained. m.p. 65°–75° C.; $^1$H NMR (300M Hz, DMSO-d$_6$); 1.08 (6H, s), 1.20 (9H, s), 1.23 (6H, d, J=7 Hz), 2.95 (1H, septet, J=7 Hz), 3.09 (2H, bs), 4.43 (2H, s), 5.47 (2H, s), 6.88 (2H, d, J=8.25 Hz), 6.98 (1H, dd, J= 1.5 and 8.25 Hz), 7.25 (1H, d, J=8.25 Hz), 7.34 (2H, d, J=8.25 Hz), 7.47 (1H, d, J=1.5 Hz), 7.55 (1H, s), 12.67 (1H, bs); MS (M+H)$^+$=529. Analysis calc'd for $C_{29}H_{37}ClN_2O_3S$: C, 65.83; H, 7.05; N, 5.29; Found: C, 66.07; H, 7.09; N, 5.15.

EXAMPLE 21

Preparation of
2-(3-amino-2,2-dimethylpropyl)-1-(4-chlorophenylmethyl)-3
-(1,1-dimethylethylthio-5-(1-methylethyl)indole

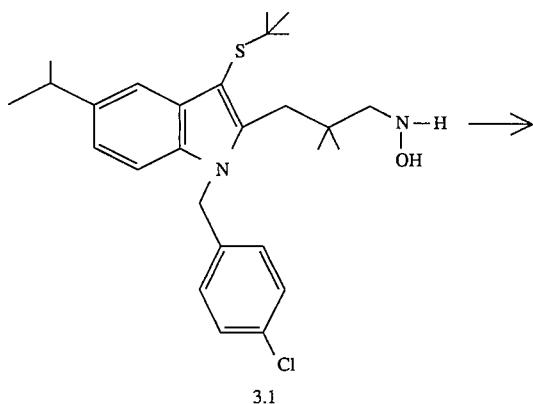

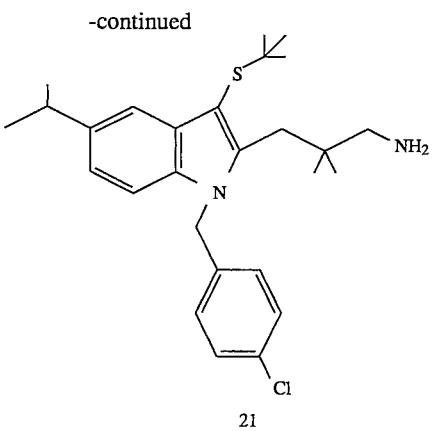

To a stirring solution of Compound 3.1 (10.9 g, 23.1 mmol) in 2/1/1 EtOH-EtOAc/THF, 20 g of an aqueous preparation of RaNi (50% in H$_2$O) was added. After stirring for thirty minutes, the reaction was carefully filtered. The catalyst was washed with THF—making sure it was not allowed to go completely dry. The resulting filtrate was concentrated and purified by flash chromatography (silica gel, 3.3/96.5 MeOH/CH$_2$Cl$_2$) to yield 7.84 g of Compound 21 as an amorphous white solid.

M.p. 58°–68° C.; $^1$H NMR (300M Hz, DMSO-d$_6$); 0.82 (6H, s), 1.20 (9H, s), 1.23 (6H, d, J=7 Hz), 1.85 (2H, bs), 2.38 (2H, s), 2.87–3.00 (3H, m), 5.58 (2H, s), 6.88 (2H, d, J=8.25 Hz), 6.96 (1H, dd, J=1.5 and 8.25 Hz), 7.23 (1H, d, J=8.23 Hz), 7.33 (2H, d, J=8.25 Hz), 7.46 (1H, d, J=1.5 Hz); MS (M+H)$^+$=457. Analysis calc'd for $C_{27}H_{37}ClN_2S$: C, 70.94; H, 8.16; N, 6.13; Found: C, 70.64; H, 8.13; N, 6.11.

EXAMPLE 22

Preparation of
N-[3-(1-(4-chlorophenylmethyl-3-(1,1-dimethylethylthio)-5-(1
-methylethyl)indol-2-yl)-2,2-dimethylpropyl]acetamide

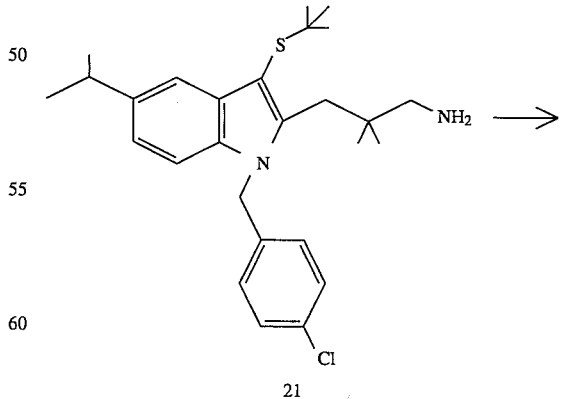

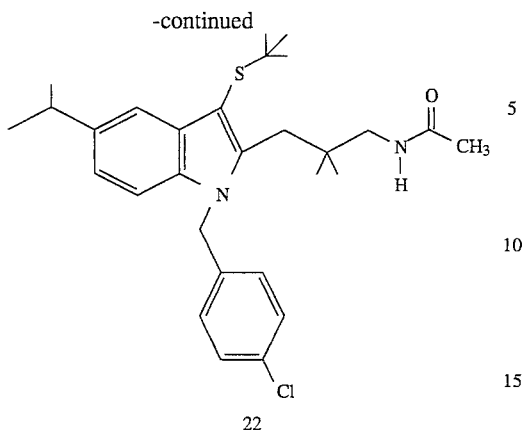

22

To a 0° C. stirring solution of Compound 21 (525 mg, 1.15 mmol) in CH₃CN (4 mL), diisopropylethylamine (0.40 mL, 2.3 mmol) and acetic anhydride (0.11 mL, 1.15 mol) were added neat and sequentially. The cooling bath was removed immediately. After five minutes, the reaction was poured into 10-% HCl (aq) and extracted with EtOAc (2×50 mL). The organic layers were combined, washed (3×brine), dried (MgSO₄), and concentrated in vacuo to yield 591 mg of an off-white solid. Recrystallization from Et₂O/CH₂CL₂/EtOAc/Hexane afforded 130 mg of a white solid.

M.p. 137.8°–139° C.; $^1$H NMR (300M Hz, DMSO-d₆); 0.82 (6H, s), 1.20 (9H, s), 1.22 (6H, d, J=7 Hz), 1.85 (3H, s), 2.82–3.08 (5H, m), 5.52 (2H, s), 6.87 (2H, d, J=8.25 Hz), 6.97 (1H, dd, J=1.5 and 8.25 Hz), 7.23 (1H, d, J= 8.25 Hz), 7.33 (2H, d, J=8.25 Hz), 7.47 (1H, d, J=1.5 Hz), 7.83 (1H, t, J=6Hz); MS (M+H)⁺=499. Analysis calc'd for C₂₉H₃₉ClN₂OS: C, 69.78; H, 7.88; N, 5.16; Found: C, 69.87; H, 7.91; N, 5.60.

EXAMPLE 23

Preparation of
N-[trans-2-(1-(4-chlorophenylmethyl)-3-(1,1-dimethylethylthio)-5
-(1-methylethyl)indol-2-yl)cyclopropyl]methyl urea

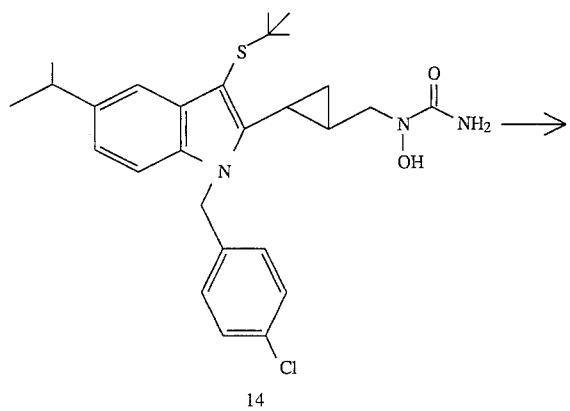

14

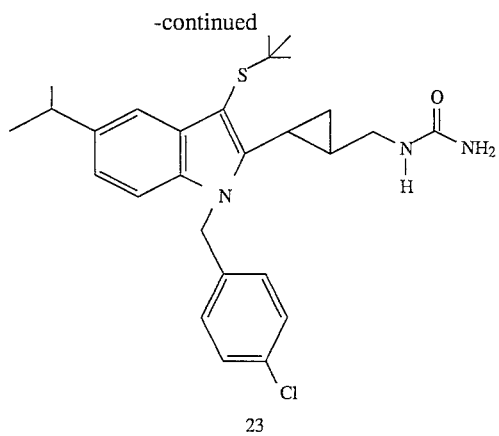

23

Compound 23 was prepared starting with Compound 14 and following the procedure employed for the conversion of 3 to 5. Purification by flash chromatography (silica gel, 95/5 Et₂O/MeOH) afforded 20 mg of 23 as an amorphous white solid. $^1$H NMR (300M Hz, DMSO-d₆); 0.89 (1H,m), 1.18 (1H, m), 1.21 (6H, d, J=7Hz), 1.24 (9H, s), 1.45 (1H, m), 1.68 (1H, m), 2.94 (2H, m), 3.30 (1H, m), 5.44 (2H, bs), 5.58 (2H, bs), 6.06 (1H, J=6 Hz); MS (M+H)⁺=484 and (M+NH₄)=501.

EXAMPLE 24

Preparation of
N'-hydroxy-N-3-[3-(1,1-dimethylethylthio)-5-(1-methylethyl)-2
-((2-methyl-2-ethoxycarbonyl)propyl)indol-1-yl]propyl urea

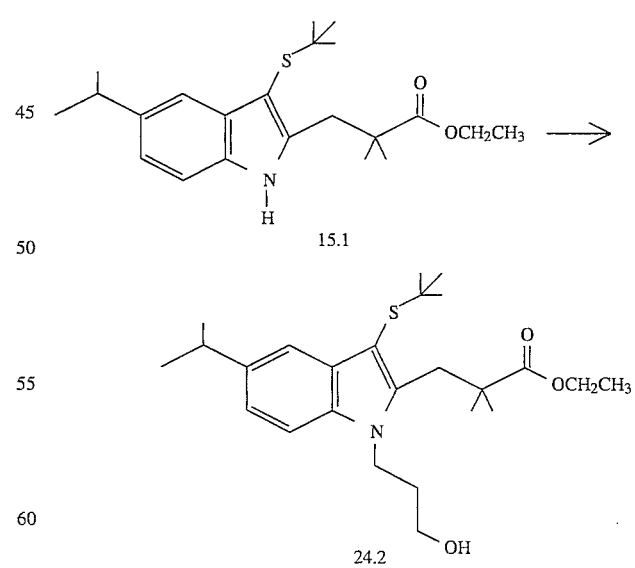

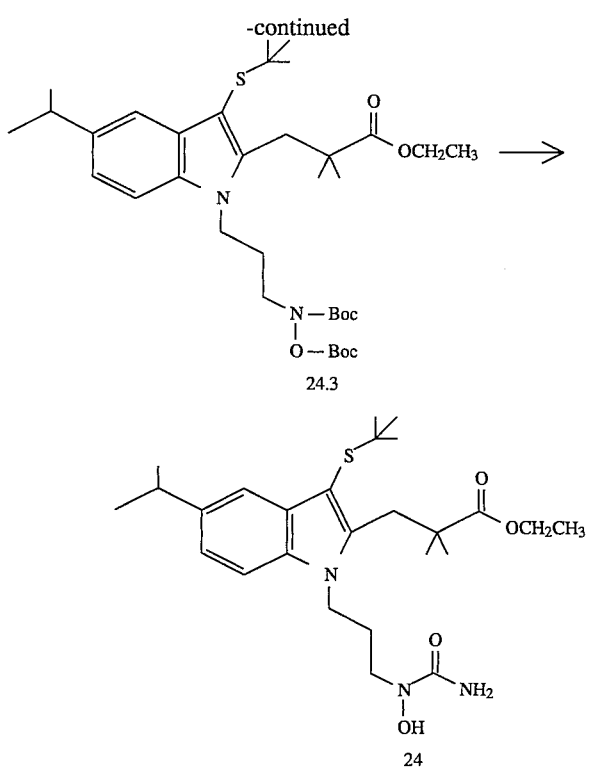

To a stirring DMSO solution (15 mL) of 15.1 (2.91 g, 8.22 mmol), NaH (271 mg, 9.05 mmol) and allyl bromide (0.78 mL, 9.05 mmol) were added neat and sequentially. The reaction was stirred under $N_2(g)$ for 18 hours then poured into 50% aqueous $NH_4Cl$ and extracted with EtOAc (2×50 mL). The combined organic extracts were washed (2×$H_2O$ and 3×brine), dried ($MgSO_4$), and concentrated in vacuo to yield 273 mg of a viscous, yellow oil. This was purified by chromatography (silica gel, 2% EtOAc/$CCl_4$) to yield 214 mg of allyl intermediate 24.1 as a viscous oil.

To a stirring THF (17 mL) solution of 24.1 (1.80 g, 4.33 mmol) under $N_2(g)$, a 0.5M solution of 9-BBN in THF (43.3 mL, 21.7 mmol) was added rapidly, and the reaction allowed to stir 18 hours at room temperature. NaOH (868 mg, 21.7 mmol) in $H_2O$ (7 mL) was added all at once. The reaction was cooled to 0° C. (ice/$H_2O$ bath) and a 30% aqueous $H_2O_2$ solution (7.4 g, 65 mmol) added in three portions over a 5 minute period. The reaction was stirred for 10 minutes at 0° C. before diluting with brine (75 mL) and extracting with Et20 (2×100 mL). The $Et_2O$ extracts were combined, washed (2×50 mL, brine), dried ($Na_2SO_4$), and concentrated in vacuo to yield 1.12 g of hydroxy intermediate 24.2 as an orange, viscous oil after purification by chromatography (silica gel, 35% EtOAc/hexane).

To a stirring THF (10 mL) solution of 24.2 under $N_2(g)$ atmosphere, triphenylphosphine (810 mg, 3.09 mmol) and bis-N,O-tert-butyloxycarbonylhydroxylamine (665 mg, 2.85 mmol) were added neat and sequentially. The homogeneous solution was cooled to −10° C. (ice/EtOH bath) and diethylazodicarboxylate (0.49 mL, 3.09 mmol) in THF (2 mL) was added dropwise over a 5 minute interval. The reaction was allowed to warm to room temperature and stir 18 hours. The reaction was concentrated in vacuo and purified by chromatography (silica gel, 3% EtOAc/$CCl_4$) to obtain 702 mg of 24.3 as an amorphous solid.

To a stirring $CH_2Cl_2$ (5 mL) solution of 24.3, was added TFA (5 mL). The reaction was stirred 8 minutes and then immediately poured into a sat'd aqueous $Na_2CO_3$ solution and extracted with EtOAc (2×100 mL). The organic extracts were combined, washed (50% aqueous $NaHCO_3$, and brine), dried ($Na_2SO_4$), and concentrated in vacuo to yield 384 mg of the resulting hydroxylamine, 24.4. This was used without further purification.

To a stirring THF (3 mL) solution of 24.4 (355 mg, 0.791 mmol) under $N_2(g)$ atmosphere, trimethylsilyl isocyanate (0.63 mL, 3.96 mmol) was added. The reaction was stirred for 90 minutes, concentrated in vacuo, and purified by chromatography (silica gel, 3% MeOH/$CH_2Cl_2$) to yield 184 mg of 24 as an amorphous solid. m.p. 64° C.; $^1H$ NMR (300M Hz, DMSO-$d_6$); 1.10 (6H, s), 1.13–1.20 (12 H, m), 1.25 (6H, d, J=6.9 Hz), 1.81 (2H, quintet, J=6.9 Hz), 2.97 (1H, septet, J=6.9 Hz), 3.22–3.32 (4H, m), 4.06 (2H, quartet, J=6.9 Hz), 4.21 (2H, t, J=6.9 Hz), 6.33 (2H, s), 7.05 (1H, dd, J=1.5 and 8.25 Hz), 7.41 (1 H, d, J= 8.25 Hz), 7.43 (1H, d, J=1.5 Hz), 9.28 (1H, s); MS $(M+H)^+$=492 and $(M+NH_4)^+$= 509. Analysis calc'd for $C_{26}H_{41}N_3O_4S(0.5\ H_2O)$: C, 62.94; H, 8.43; N, 8.47; Found: C, 62.99; H, 8.49; N, 8.39.

Substituted indole N-hydroxyureas presented in Table 3 are prepared by the method used for Example 1 substituting N-methylhydroxylamine for the requisite N-substituted hydroxylamine, $R^2NHOH$.

TABLE 3

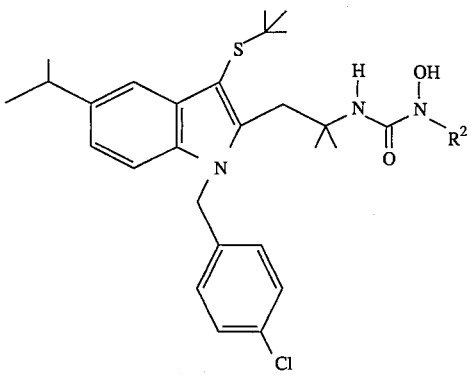

| Example | $R^2$ |
|---|---|
| 25 | —$CH_2CH_3$ |
| 26 | —$CH_2CH_2C_6H_5$ |
| 27 | —$CH_2CH_2COOCH_3$ |
| 28 | —$CH_2CH_2CONH_2$ |
| 29 | —$CH_2CH_2CH_2OH$ |
| 30 | —$CH_2CH_2OH$ |
| 31 | —$CH_2CH_2OCH_3$ |
| 32 | —$CH_2CH_2OC_6H_5$ |
| 33 | —$CH_2CH_2OCOCH_3$ |
| 34 | —$CH_2CH_2$-2-pyridyl |
| 35 | —$CH_2CH_2$-3-pyridyl |
| 36 | —$CH_2CH_2$-4-pyridyl |

Substituted indole N-hydroxyurea compounds of the present invention presented in Table 4 are prepared by the method used for Example 3 substituting trimethylsilylisocyanate with the requisite N-substituted isocyanate, $R^3$—N=C=O.

TABLE 4

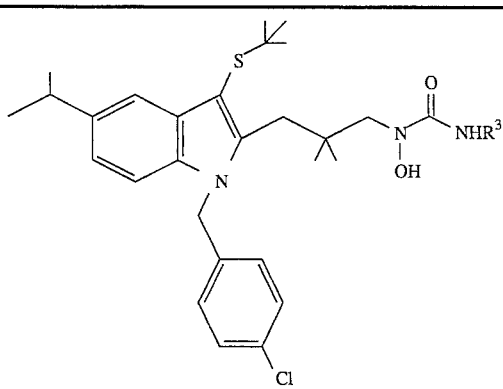

| Example | R³ |
|---|---|
| 37 | —CH₂CH₃ |
| 38 | —CH₂CH₂C₆H₅ |
| 39 | —CH₂CH₂COOCH₃ |
| 40 | —CH₂CH₂CONH₂ |
| 41 | —CH₂CH₂CH₂COOCH₃ |
| 42 | —(CH₂)₄COOCH₃ |
| 43 | —CH₂C₆H₅ |
| 44 | —CH₂CH₂OCH₃ |
| 45 | —CH₂CH₂OC₆H₅ |
| 46 | —CH₂CH₂OC(O)CH₃ |
| 47 | —CH₂CH₂-2-pyridyl |
| 48 | —CH₂CH₂-3-pyridyl |
| 49 | —CH₂CH₂-4-pyridyl |
| 50 | —C₆H₅ |
| 51 | -3-pyridyl |
| 52 | -2-furyl |
| 53 | -3-thienyl |
| 54 | -2-benzo[b]thienyl |
| 55 | -2-benzo[b]furyl |
| 56 | -2-thiazoyl |

Substituted indole urea compounds in accordance with the present invention presented in Table 5 are prepared by the method used for Example 5 by deoxygenation of the N-hydroxyurea examples shown in Table 4.

TABLE 5

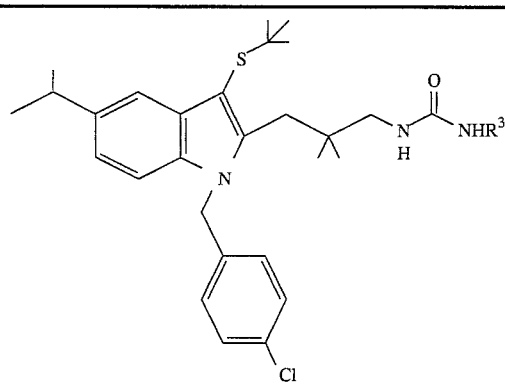

| Example | R³ |
|---|---|
| 57 | —CH₂CH₃ |
| 58 | —CH₂CH₂C₆H₅ |
| 59 | —CH₂CH₂COOCH₃ |
| 60 | —CH₂CH₂CONH₂ |
| 61 | —CH₂CH₂CH₂COOCH₃ |
| 62 | —(CH₂)₄COOCH₃ |
| 63 | —CH₂C₆H₅ |
| 64 | —CH₂CH₂OCH₃ |
| 65 | —CH₂CH₂OC₆H₅ |
| 66 | —CH₂CH₂OCOCH₃ |

TABLE 5-continued

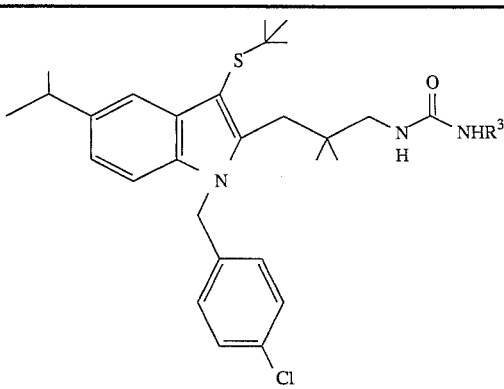

| Example | R³ |
|---|---|
| 67 | —CH₂CH₂-2-pyridyl |
| 68 | —CH₂CH₂-3-pyridyl |
| 69 | —CH₂CH₂-4-pyridyl |
| 70 | —C₆H₅ |
| 71 | -3-pyridyl |
| 72 | -2-furyl |
| 73 | -3-thienyl |
| 74 | -2-benzo[b]thienyl |
| 75 | -2-benzo[b]furyl |
| 76 | -2-thiazoyl |

Substituted indole oxime derivatives presented in Table 6 are prepared by the method used for Example 2 substituting hydroxylamine with the requisite O substituted hydroxylamine R²ONH₂.

TABLE 6

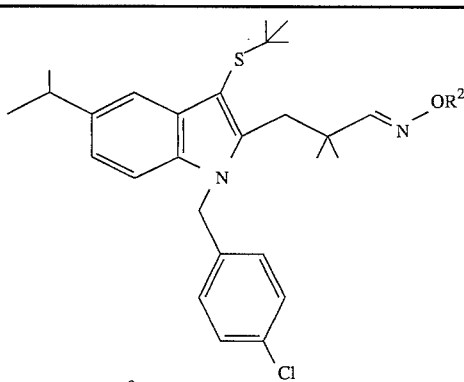

| Example | R² |
|---|---|
| 77 | —CH₂CH₃ |
| 78 | —CH₂CH₂C₆H₅ |
| 79 | —CH₂CH₂COOCH₃ |
| 80 | —CH₂CH₂CONH₂ |
| 81 | —CH₂CONH₂ |
| 82 | —(CH₂)₂CON(Et)₂ |
| 83 | —CH₂—(N-morpholine) |
| 84 | —CH₂—(N-priperidine) |
| 85 | —CH₂—(N-priperazine) |
| 86 | —CH₂—COO—CH₂CH₂NH₂ |
| 87 | —CH₂—COO—CH₂CH(OH)CH₂OH |
| 88 | —CH₂—COOCH(CH₃)O(O)CC(CH₃)₃ |
| 89 | —CH₂—COO—CH₂—N-succinimide |
| 90 | —(CH₂)₃COOCH₃ |
| 91 | —(CH₂)₄COOCH₃ |
| 92 | —(CH₂)₂COOH |
| 93 | —(CH₂)₃COOH |
| 94 | —(CH₂)₄COOH |
| 95 | —(CH₂)₂CH₂OH |
| 96 | —(CH₂)₃CH₂OH |
| 97 | —(CH₂)₄CH₂OH |

TABLE 6-continued

| Example | R² |
|---------|-----|
| 98 | —CH₂CON(OH)CH₃ |
| 99 | —(CH₂)₂CON(OH)CH₃ |
| 100 | —CH(COOCH₃)₂ |
| 101 | —CH(COOH)₂ |
| 102 | —CH₂C₆H₅ |
| 103 | —CH₂CH₂OCH₃ |
| 104 | —CH₂CH₂OC₆H₅ |
| 105 | —CH₂CH₂OCOCH₃ |
| 106 | —CH₂CH₂-2-pyridyl |
| 107 | —CH₂CH₂-3-pyridyl |
| 108 | —CH₂CH₂-4-pyridyl |
| 109 | —CH₂-3-benzoic acid |
| 110 | —CH₂-3-pyridyl |
| 111 | —CH₂-2-furyl |
| 112 | —CH₂-3-thienyl |
| 113 | —CH₂-2-benzo[b]thienyl |
| 114 | —CH₂-2-benzo[b]furyl |
| 115 | —CH₂-2-thiazoyl |
| 116 | —CH₂-5-tetrazoyl |
| 117 | —CH₂-5-triazoyl |
| 118 | —CH₂-2-imidazoyl |
| 119 | —CH₂-2-pyrimidyl |

Substituted indole acid derivatives presented in Table 7 are prepared by the method used for Example 15 substituting 4-pyridylmethanol with the requisite heteroarylmethanol intermediate B—OH.

TABLE 7

| Example | B |
|---------|-----|
| 120 | —CH₂-2-pryidyl |
| 121 | —CH₂-3-pyridyl |
| 122 | —CH₂-4-pyridyl |
| 123 | —CH₂-2-furyl |
| 124 | —CH₂-3-furyl |
| 125 | —CH₂-2-thienyl |
| 126 | —CH₂-3-thienyl |
| 127 | —CH₂-2-benzo[b]thienyl |
| 128 | —CH₂-2-benzo[b]furyl |
| 129 | —CH₂-2-thiazoyl |
| 130 | —CH₂-2-imidazoyl |
| 131 | —CH₂-2-pyrimidyl |

Substituted indole oxime derivatives as shown in Table 8 are prepared by the method used for Example 2 substituting compound 1.1 with the indole acid compounds described in Table 7 and reaction of the requisite aldehyde with the appropriate hydroxylamine, R²ONH₂.

TABLE 8

| Example | B | R² |
|---------|-----|-----|
| 132 | —CH₂-2-pyridyl | —CH₂COOH |
| 133 | —CH₂-3-pyridyl | —CH₂COOH |
| 134 | —CH₂-4-pyridyl | —CH₂COOH |
| 135 | —CH₂-2-furyl | —(CH₂)₂COOH |
| 136 | —CH₂-3-furyl | —(CH₂)₂COOH |
| 137 | —CH₂-2-thienyl | —CH₂COOH |
| 138 | —CH₂-3-thienyl | —CH₂COOH |
| 139 | —CH₂-2-benzo[b]thienyl | —CH₂COOH |
| 140 | —CH₂-2-benzo[b]furyl | —CH₂COOH |
| 141 | —CH₂-2-thiazoyl | —CH₂COOH |
| 142 | —CH₂-2-imidazoyl | —CH₂COOH |
| 143 | —CH₂-2-pyrimidyl | —CH₂COOH |

Substituted indole oxime derivatives as shown in Table 9 are prepared by the method used for Example 11 where 11.1 is desulfurized to provide the indole intermediate 11.2 and then 11.2 is converted to various oxime derivatives by the method of Example 2 substituting hydroxylamine with the requisite 0-substituted hydroxylamine, R²ONH₂.

TABLE 9

| Example | R² |
|---------|-----|
| 144 | —CH₂COOH |
| 145 | —CH₂CH₂OH |
| 146 | —CH₂CH₃ |
| 147 | —CH₂CH₂C₆H₅ |
| 148 | —CH₂CH₂COOCH₃ |
| 149 | —CH₂CH₂CONH₂ |
| 150 | —CH₂CONH₂ |
| 151 | —(CH₂)₂CON(Et)₂ |
| 152 | —CH₂-morpholinylamide |
| 153 | —CH₂-piperidinylamide |
| 154 | —CH₂-1,5-piperizinylamide |
| 155 | —CH₂—COO—CH₂CH₂NH₂ |
| 156 | —CH₂—COO—CH₂CH(OH)CH₂OH |
| 157 | —CH₂—COO—CH(CH₃)OOC(CH₃)₃ |
| 158 | —CH₂—COO—CH₂—N-succinimide |
| 159 | —(CH₂)₃COOCH₃ |
| 160 | —(CH₂)₄COOCH₃ |
| 161 | —(CH₂)₂COOH |
| 162 | —(CH₂)₃COOH |
| 163 | —(CH₂)₄COOH |
| 164 | —(CH₂)₂CH₂OH |
| 165 | —(CH₂)₃CH₂OH |

TABLE 9-continued

[Structure: 5-isopropyl-1-(4-chlorobenzyl)indole with 2-substituent CH₂C(CH₃)₂CH=N-OR²]

| Example | R² |
|---|---|
| 166 | —(CH₂)₄CH₂OH |
| 167 | —CH₂CON(OH)CH₃ |
| 168 | —(CH₂)₂CON(OH)CH₃ |
| 169 | —CH(COOCH₃)₂ |
| 170 | —CH(COOH)₂ |
| 171 | —CH₂C₆H₅ |
| 172 | —CH₂CH₂OCH₃ |
| 173 | —CH₂CH₂OC₆H₅ |
| 174 | —CH₂CH₂OCOCH₃ |
| 175 | —CH₂CH₂-2-pyridyl |
| 176 | —CH₂CH₂-3-pyridyl |
| 177 | —CH₂CH₂-4-pyridyl |
| 178 | —CH₂-3-benzoic acid |
| 179 | —CH₂-3-pyridyl |
| 180 | —CH₂-2-furyl |
| 181 | —CH₂-3-thienyl |
| 182 | —CH₂-2-benzo[b]thienyl |
| 183 | —CH₂-2-benzo[b]furyl |
| 184 | —CH₂-2-thiazoyl |
| 185 | —CH₂-5-tetrazoyl |
| 186 | —CH₂-5-triazoyl |
| 187 | —CH₂-2-imidazoyl |
| 188 | —CH₂-2-pyrimidyl |

Substituted indole amine derivatives presented in Table 10 are prepared by reductive amination (with for example sodium cyanoborohydride) of the aldehyde 2.2 using the requisite amine.

TABLE 10

[Structure: 5-isopropyl-3-(tert-butylthio)-1-(4-chlorobenzyl)indole with 2-substituent CH₂C(CH₃)₂CH₂NHR²]

| Example | R² |
|---|---|
| 189 | —CH₂COOCH₃ |
| 190 | —CH₂CH₂OH |

TABLE 10-continued

[Structure: 5-isopropyl-3-(tert-butylthio)-1-(4-chlorobenzyl)indole with 2-substituent CH₂C(CH₃)₂CH₂NHR²]

| Example | R² |
|---|---|
| 191 | —CH₂CH₃ |
| 192 | —CH₂CH₂C₆H₅ |
| 193 | —CH₂CH₂COOCH₃ |
| 194 | —CH₂CH₂CONH₂ |
| 195 | —CH₂CONH₂ |
| 196 | —(CH₂)₂CON(Et)₂ |
| 197 | —CH₂—COO—CH₂CH₂NH₂ |
| 198 | —CH₂—COO—CH₂CH(OH)CH₂OH |
| 199 | —CH₂—COO—CH(CH₃)OOC(CH₃)₃ |
| 200 | —CH₂—COO—CH₂—N-succinimide |
| 201 | —(CH₂)₃COOCH₃ |
| 202 | —(CH₂)₄COOCH₃ |
| 203 | —(CH₂)₂CH₂OH |
| 204 | —(CH₂)₃CH₂OH |
| 205 | —(CH₂)₄CH₂OH |
| 206 | —CH₂CON(OH)CH₃ |
| 207 | —(CH₂)₂CON(OH)CH₃ |
| 208 | —CH(COOCH₃)₂ |
| 209 | —CH₂C₆H₅ |
| 210 | —CH₂CH₂OCH₃ |
| 211 | —CH₂CH₂OC₆H₅ |
| 212 | —CH₂CH₂OCOCH₃ |
| 213 | —CH₂CH₂-2-pyridyl |
| 214 | —CH₂CH₂-3-pyridyl |
| 215 | —CH₂CH₂-4-pyridyl |
| 216 | —CH₂-3-benzoic acid |
| 217 | —CH₂-3-pyridyl |
| 218 | —CH₂-2-furyl |
| 219 | —CH₂-3-thienyl |
| 220 | —CH₂-2-benzo[b]thienyl |
| 221 | —CH₂-2-benzo[b]furyl |
| 222 | —CH₂-2-thiazoyl |
| 223 | —CH₂-5-tetrazoyl |
| 224 | —CH₂-5-triazoyl |
| 225 | —CH₂-2-imidazoyl |
| 226 | —CH₂-2-pyrimidyl |
| 227 | —C₆H₅ |
| 228 | -2-furyl |
| 229 | -3-thienyl |
| 230 | -2-benzo[b]thienyl |
| 231 | -2-benzo[b]furyl |
| 232 | -2-thiazoyl |

Substituted indole hydroxamic acid derivatives as shown in Table 11 are prepared by the method of Example 3 substituting trimethylsilylisocyanate with the requisite carboxylic acid chloride or anhydride and suitable base such as pyridine or triethylamine.

TABLE 11

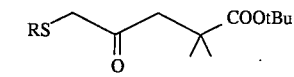

| Example | R₂ |
|---|---|
| 233 | —CH₂COOCH₃ |
| 234 | —CH(CH₃)OCH₃ |
| 235 | —CH₂CH₃ |
| 236 | —CH₂CH₂C₆H₅ |
| 238 | —CH(CH₃)COOCH₃ |
| 238 | —CH₂CH₂CONH₂ |
| 239 | —CH₂CONH₂ |
| 240 | —(CH₂)₂CON(Et)₂ |
| 241 | —CH₂COOCH(CH₃)O(O)CC(CH₃)₃ |
| 242 | —CH(CH₃)COOCH₃ |
| 243 | —(CH₂)₄COOCH₃ |
| 244 | —(CH₂)₂COOCH₃ |
| 245 | —(CH₂)₂CH₂OCH₃ |
| 246 | —(CH₂)₃CH₂OCH₃ |
| 247 | —(CH₂)₄CH₂OCH₃ |
| 248 | —CH(COOCH₃)₂ |
| 249 | —CH₂C₆H₅ |
| 250 | —CH₂CH₂OCH₃ |
| 251 | —CH₂CH₂OC₆H₅ |
| 252 | —CH₂CH₂OCOCH₃ |
| 253 | —CH₂-2-furyl |
| 254 | —CH₂-3-thienyl |
| 255 | —CH₂-2-benzo[b]thienyl |
| 256 | —CH₂-2-benzo[b]furyl |
| 257 | —CH₂-2-thiazoyl |
| 258 | —CH₂-5-tetrazoyl |
| 259 | —CH₂-5-triazoyl |
| 260 | —CH₂-2-imidazoyl |
| 261 | —CH₂-2-pyrimidyl |
| 262 | —C₆H₅ |
| 263 | -2-furyl |
| 264 | -3-thienyl |
| 265 | -2-benzo[b]thienyl |
| 266 | -2-benzo[b]furyl |
| 267 | -2-thiazoyl |

Substituted indole hydroxamic acid derivatives X presented in Table 12 are prepared by the method of Example 4 substituting the intermediate 4.1 with the requisite alpha-substituted ketone intermediate VIII to provide the indole intermediate IX which is then converted to the corresponding oxime derivatives X.

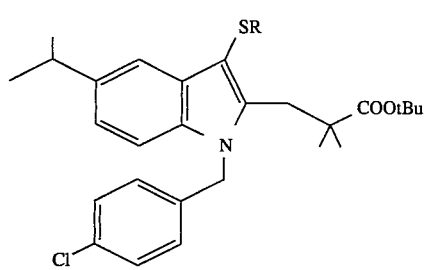

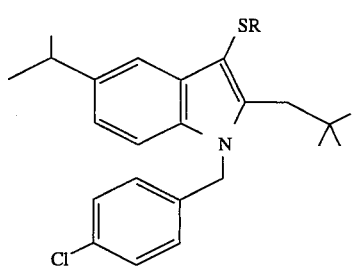

TABLE 12

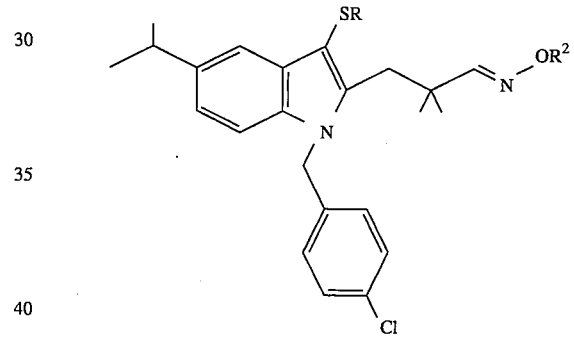

| Example | R | R² |
|---|---|---|
| 268 | 2-pyridyl | —CH₂COOH |
| 269 | 3-pyridyl | —CH₂COOH |
| 270 | 4-pyridyl | —CH₂COOH |
| 271 | 4-fluorophenyl | —CH₂COOH |
| 272 | 2-thiazoyl | —CH₂COOH |
| 273 | 1-methyl-1-ethylphenyl | —CH₂COOH |
| 274 | benzyl | —CH₂COOH |
| 275 | —CH₂-2-pyridyl | —CH₂COOH |
| 276 | isopropyl | —CH₂COOH |
| 277 | 2-thienyl | —CH₂COOH |
| 278 | 3-thienyl | —CH₂COOH |

EXAMPLE 279

Preparation of 2,2-dimethyl-3-[1-(2-thiophenylmethyl)-3-(1,1-dimethylethylthio)-5-(1-methylethyl)indol-2-yl]propionaldehyde oxime

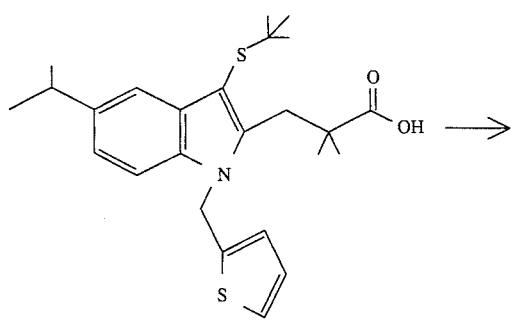

16

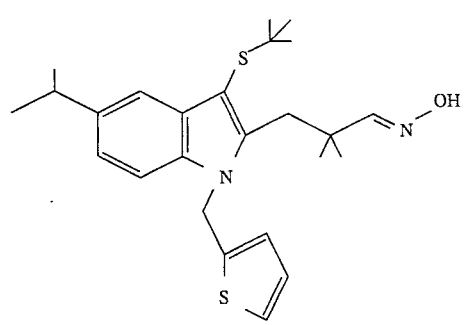

279

Starting with the product of Example 16 (2.36 g, 5.49 mmol) and adapting the procedure described in Example 2, 3.12 g of crude oxime (containing pyridinium hydrochloride) was obtained. A portion (165 mg) of this product was purified by chromatography (silica gel, 5/95 EtOAc/hexanes) to yield 25 mg of 279 as a solid. m.p. 115.5°–117° C.; $^1$H NMR (300 MHz, DMSO-$d_6$); 1.10 (6H, s), 1.18 (9H, s), 1.23 (6H, d), 2.95 (1H, septet, J=7 Hz), 3.17 (2H, bs), 5.62 (2H, bs), 6.92 (1H, dd, J=4 and 5 Hz), 6.95–7.05 (2H, m), 7.33 (1H, dd, J=1.5 and 5 Hz), 7.38–7.45 (3H, m), 10.44 (1H, s); MS $(M+H)^+$=443 and $(M+NH_4)$=460. Analysis calc'd for $C_{25}H_{34}N_2OS_2$: C, 67.83; H, 7.74; N, 6.33; Found: C, 67.50; H, 7.81; N, 6.18.

EXAMPLE 280

Preparation of N-2,2-dimethyl-3-[(1-(2-thiophenylmethyl)-3-(1,1-dimethylethyl-thio)-5-(1-methylethyl)indol-2-yl]propyl urea

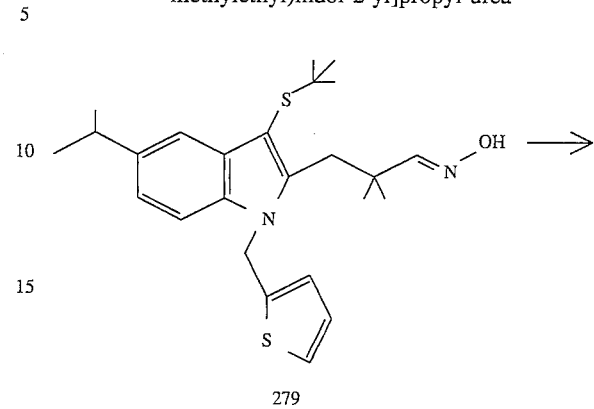

279

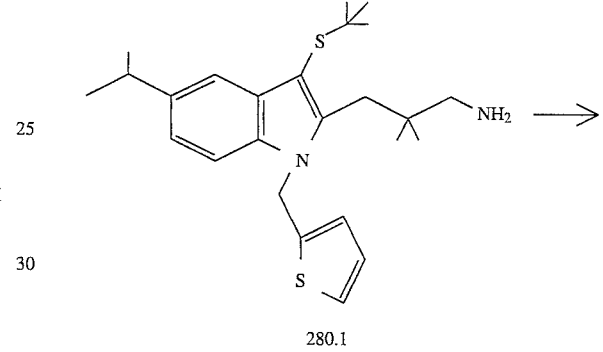

280.1

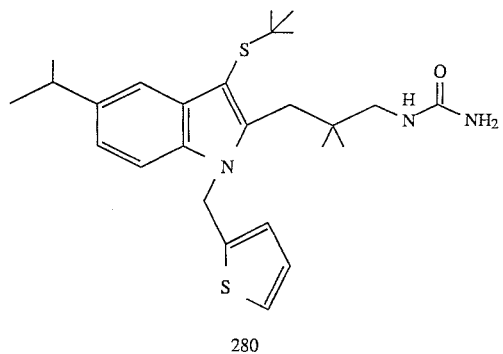

280

Starting with the product of Example 279 (1.31 g, 2.95 mmol) and adapting the procedure described in Example 21, 0.63 g of Compound 280.1 was obtained after purification by chromatography (silica gel, 20/78/2 EtOAc/hexanes/isopropylamine and 10/90 MeOH/CH$_2$Cl$_2$). Compound 280 was prepared from 280.1 (0.24 g, 0.57 mmol) by adapting the procedure of Example 3. After purification by chromatography (silica gel, 75/25 THF/hexanes) and recrystallization from EtOAc/hexanes/MeOH, 19 mg of Compound 280.1 was obtained as a white solid. m.p. 163.5°–164.5° C.; $^1$H NMR (300M Hz, DMSO-$d_6$); 0.83 (6H, s), 1.18 (9H, s), 1.22 (6H, d, J=7 Hz), 2.88–3.00 (5H, m), 5.45 (2H, bs), 5.67 (2H, bs), 6.07 (1H, bt, J=6 Hz), 6.91 (1H, dd, J=4 and 5.3 Hz), 6.96–7.02 (2H, m), 7.32 (1H, dd, J=1,5 and 5.3 Hz), 7.37–7.46 (2H, m); MS (M+H)$^+$=472. Analysis calc'd for $C_{26}H_{37}N_3OS_2$: C, 66.20; H, 7.91; N, 8.91; Found: C, 66.53; H, 8.00; N, 8.93.

EXAMPLE 281

Preparation of 3-[1-(4-chlorophenylmethyl)-3-(1,1-dimethylethylthio)-5-(methoxy)indol-2-yl]-2,2-dimethylpropionaldehyde oxime-O-2-acetic acid

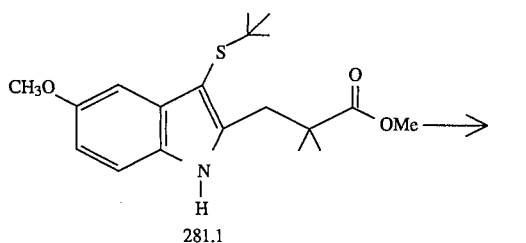
281.1

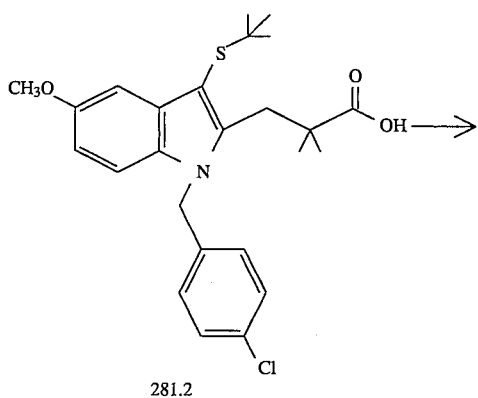
281.2

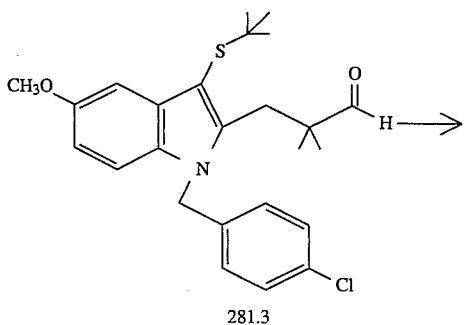
281.3

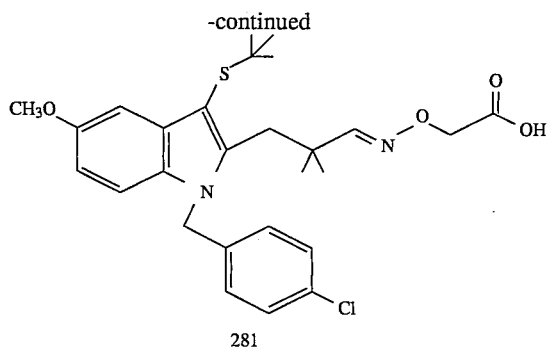
281

Compound 281.1 was prepared by adapting the procedure reported in EPA 87311031.6 using 4-methoxyphenylhydrazine hydrochloride hydrate.

Starting with 281.1 (8.0 g, 23 mmol) and adapting the procedure described in Example 15, in which 4-chlorobenzyl bromide was substituted for 4-pyridinemethanol, 6.17 g of crude 281.2 was obtained. A portion (1.05 g) of this crude material was purified by recrystallization from EtOAc/hexanes to yield 0.87 g of Compound 281.2 as a white solid. m.p. 193.5°–194.5° C.; $^1$H NMR (300M Hz, DMSO-$d_6$); 1.06 (6H, s), 1.17 (9H, s), 3.15 (2H, bs), 3.72 (3H, s), 5.43 (2H, s), 6.68 (1H, dd, J= 2.25 and 9 Hz), 6.78 (2H, d, J=9 Hz), 7.06 (1H, d, J=2.25 Hz), 7.25 (1H, d, J=9 Hz), 7.28 (2H, d, J=9 Hz), 12.42 (1H, bs); MS (M+H)$^+$=460 and (M+Na)$^+$ =482. Analysis calc'd for $C_{25}H_{30}ClNO_3S(0.25\ H_2O)$: C, 64.64; H, 6.62; N, 3.02; Found: C, 64.57; H, 6.39; N, 3.02.

Starting with 281.2 (5.1 g, 11 mmol) and adapting the procedure described in Example 2, 4.1 g of 281.3 was obtained after purification by chromatography (silica gel, 10/90 and 20/80 EtOAc/hexanes).

Compound 281 was prepared by following the procedure detailed in Example 20. After purification by chromatography (silica gel, 20/78/2 EtOAc/hexanes/HOAc) and recrystallization from benzene/hexanes, 0.57 g of 281 was obtained as a white powder. m.p. 138°–139° C.; $^1$H NMR (300M Hz, DMSO-$d_6$); 1.08 (6H, s), 1.22 (9H, s), 3.07 (2H, bs), 3.75 (3H, s), 4.42 (2H, s), 5.47 (2H, s), 6.72 (1H, dd, J=1.5 and 9 Hz), 6.85 (2H, d, J=9 Hz), 7.08 (1H, d, J=1.5 Hz), 7.23 (1H, d, J=9 Hz), 7.32 (2H, d, J=9 Hz), 7.55 (1H, s); MS (M+H)$^+$=516. Analysis calc'd for $C_{27}H_{33}ClN_2O_4S$: C, 62.72; H, 6.43; N, 5.42; Found: C, 62.68; H, 6.43; N, 5.34.

EXAMPLE 282

Preparation of
3-[1-(4-chlorophenylmethyl)-3-(1,1-dimethylethylthio-5-(1-methylethyl)
indol-2-yl]-2,2-dimethylpropionaldehyde oxime-O-3-propionic acid

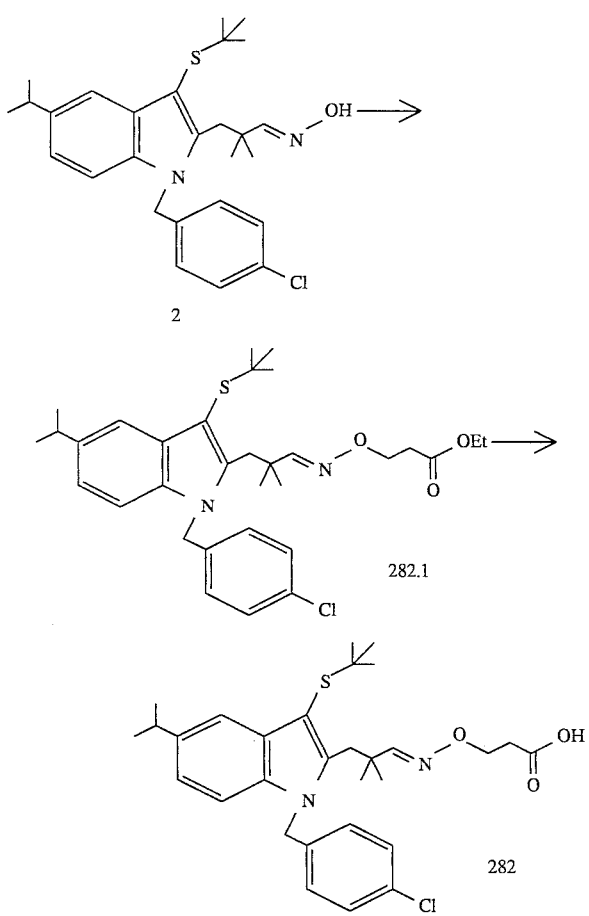

To a stirring EtOH (6.5 mL) solution of the product of Example 2, ethyl acrylate (0.27 mL, 2.5 mmol) and 0.25 mL of 2N KOH (EtOH) were added. The reaction was heated to 60° C. under N₂(g) for 18 hours. The reaction was cooled to room temperature, concentrated in vacuo and diluted with Et₂O. The Et₂O solution was washed with 50% (aq) NaHCO₃. The layers were separated and the aqueous layer back-extracted with Et₂O. The combined organic extracts were washed (1×brine), dried (MgSO₄), concentrated in vacuo, and purified by chromatography (silica gel, 10/90 Et₂O/hexanes and 20/80 EtOAc/hexanes) to yield 0.64 g of recovered 2 and 0.58 g of 282.1 as a pale yellow oil.

Compound 282 was prepared by the methodology in Example 6 used to convert 6.1 to 6.2. After purification by chromatography (silica gel, 20/80 EtOAc/hexanes and 20/78/2 EtOAc/hexanes/HOAc) and recrystallization from benzene/petroleum ether, 0.20 g of 282 as a white solid was obtained. m.p. 50°–70° C.; ¹H NMR (300 MHz, DMSO-d₆); 1.04 (6H, s), 1.16 (9H, s), 1.18 (6H, d, J=7 Hz), 2.43 (2H, t, J=6 Hz), 2.91 (1H, septet, J=7 Hz), 3.06 (2H, bs), 4.02 (2H, t, J=6 Hz), 5.39 (2H, s), 6.85(2H, d, J=9Hz),6.93 (1H, dd, J=1.5and 9Hz), 7.18 (1H, d, J= 9 Hz), 7.29 (2H, d, J=9 Hz), 7.43 (2H, s), 12.26 (1H, bs); MS (M+H)⁺= 542. Analysis calc'd for C₃₀H39ClN₂O₃S: C, 66.34; H, 7.24; N, 5.16; Found: C, 66.37; H, 7.28; N, 5.08.

EXAMPLE 283

Preparation of
N-{3-[1-(4-chlorophenylmethyl-3-(1,1-dimethylethylthio)-5-(1-methylethyl)indol-2-yl]-2,2-dimethylpropionaldehyde oxime-O} -methyl urea

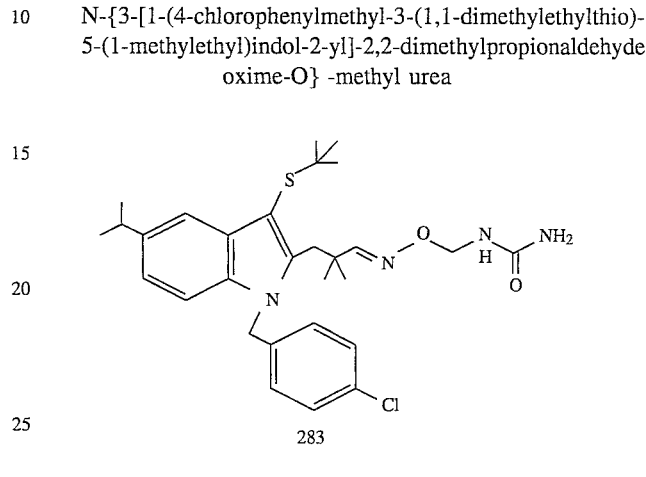

Starting with 282 (0.49 g, 0.92 mmol) and adapting the procedure described in Example 1, substituting ammonium chloride for ammonium hydroxide, 59 mg of 283 was obtained as a white amorphous solid after purification by chromatography (silica gel, 50/50 EtOAc/hexanes and EtOAc). m.p. 90°–110° C.; ¹H NMR (300M Hz, DMSO-d₆); 1.05 (6H, s), 1.16 (9H, s),1.18 (6H, d, J=7 Hz), 2.91 (1H, septet, J=7 Hz), 3.07 (2H, bs), 4.79 (2H, d, J=7 Hz), 5.37 (2H, s), 5.72 (2H, s), 6.84 (2H, d, J=9 Hz), 6.88–6.96 (2H, m), 7.18 (1H, d, J=9 Hz), 7.30 (2H, d, J=9 Hz), 7.43 (1H, d, J=1.5 Hz), 7.45 (1H, s); MS (M+H)⁺=542 and (M+Na)⁺= 565. Analysis calc'd for C₂₉H₃₉ClN₄O₂S: C, 64.13; H, 7.24; N, 10.31; Found: C, 63.86; H, 7.34; N, 10.01.

EXAMPLE 284

Preparation of
N-2-[1-(4-chlorophenylmethyl)-3-(1,1-dimethylethylthio)-5-(1-methylethyl)indol-2-yl)-2,2-dimethylpropionyl-amino]ethyl urea

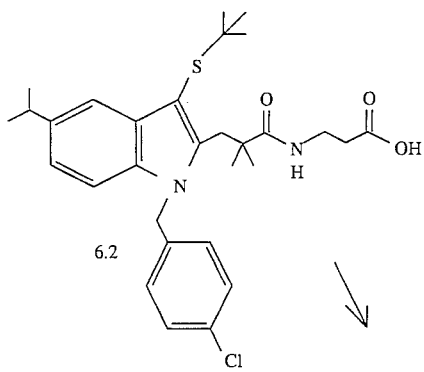

-continued

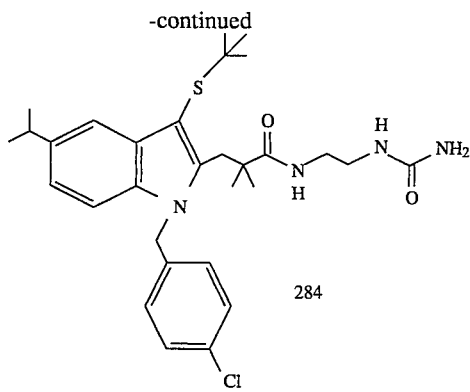
284

Starting with Compound 6.2 (0.99 g, 1.82 mmol) and adapting the procedure described in Example 1, substituting ammonium chloride for ammonium hydroxide, 0.43 g of Compound 284 was obtained as a white amorphous solid after purification by chromatography (silica gel, 5/95 MeOH/CH$_2$Cl$_2$). m.p. 100°–111° C.; $^1$H NMR (300 MHz, DMSO-d$_6$); 1.08(6H, s), 1.19 (9H, s), 1.24 (6H, d, J=7 Hz), 2.88–3.12 (6H, m), 3.16 (2H, s), 5.44 (2H, s), 5.52 (2H, s), 6.03 (1H, t, J=4.5 Hz), 6.85 (2H, d, J= 8 Hz), 7.25 (1H, d, J=8 Hz), 7.33 (2H, d, J=8 Hz), 7.47 (1H, d, J=1.5 Hz), 7.67 (1H, t, J=4.5 Hz); MS (M+H)$^+$=557/559. Analysis calc'd for C$_{30}$H$_{41}$ClN$_4$O$_2$S(0.25 H$_2$O): C, 64.15; H, 7.45; N, 9.97; Found: C, 64.13; H, 7.33; N, 9.94.

EXAMPLE 285

Preparation of
3-[1-(4-fluorophenylmethyl-3-(1,1-dimethylethylthio)-5-(1-methylethyl) indol-2-yl]-2,2-dimethylpropionaldehyde oxime-O-2-acetic acid

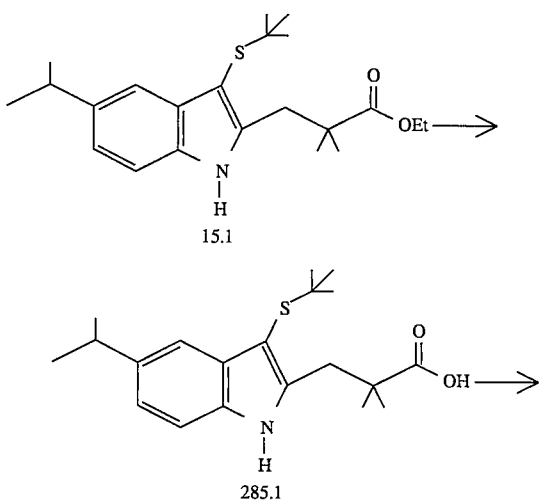

-continued

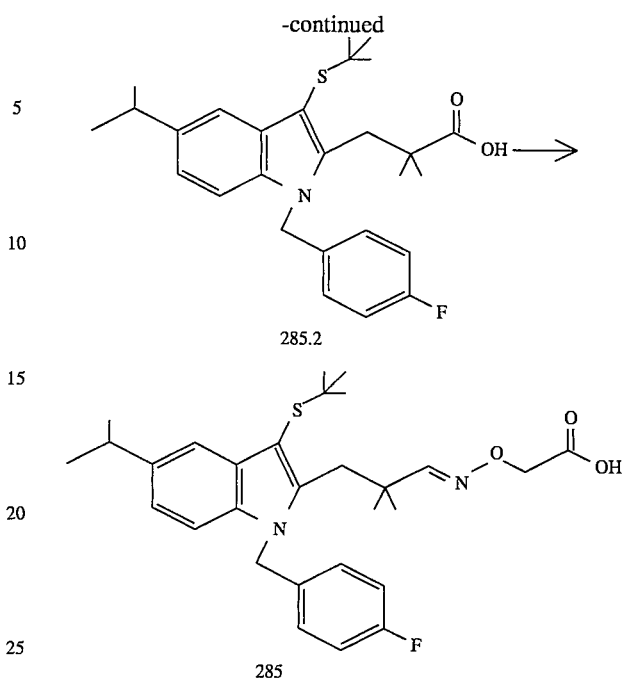

Compound 285.1 was obtained from Compound 15.1 by adapting the hydrolysis procedure reported in EPA 87311031.6.

Using compound 285.1 (0.11 g, 0.33 mmol) and adapting the procedure used to convert 15.1 to 15.2, substituting 4-fluorobenzyl bromide for 4-pyridinemethanol, 43 mg of Compound 285.2 was obtained as a white solid after purification by chromatography (silica gel, 5/93/2 EtOAc/CCl$_4$/HOAc) followed by recrystallization from benzene/hexanes. m.p. 180°–181° C.; $^1$H NMR (300 MHz, DMSO-d$_6$); 1.10 (6H, s), 1.19 (9H, s), 1.22 (6H, d, J=7 Hz), 2.96 (1H, septet, J=7 Hz), 3.22 (2H, bs), 5.47 (2H, s), 6.88 (2H, dd, J=6 and 9 Hz), 6.99 (1H, dd, J=1.5 and 9 Hz), 7.11 (2H, t, J=9 Hz), 7.29 (1H, d, J=9 Hz), 7.47 (1H, d, J=1.5 Hz), 12.45 (1H, bs); MS (M+H)$^+$=456 and (M+Na)$^+$=478. Analysis calc'd for C$_{27}$H$_{34}$FNO$_2$S(0.25 H$_2$O): C, 70.48; H, 7.56; N, 3.04; Found: C, 70.67; H, 7.37 N, 3.05.

Starting with Compound 285.2 and adapting the procedure described in Example 281, 0.82 g of 285 was obtained as a white powder after purification by chromatography (silica gel, 20/78/2 EtOAc/hexanes/HOAc) followed by recrystallization from hexanes. m.p. 124°–125° C.; $^1$H NMR (300M Hz, DMSO-d$_6$); 1.06 (6H, s), 1.13–1.30 (15H, m), 2.95 (1H, m), 3.10 (2H, bs), 4.43 (2H, s), 5.47 (2H, bs), 6.87–7.02 (3H, m), 7.10 (2H, bt, J=9 Hz), 7.25 (1H, d, J=9 Hz), 7.47 (1H, s), 7.56 (1H, s), 12.67 (1H, bs); MS (M+H)$^+$=512 and (M+Na)$^+$=535. Analysis calc'd for C$_{29}$H$_{37}$FN$_2$O$_3$S: C, 67.94; H, 7.27; N, 5.46; Found: C, 68.45; H, 7.29 N, 5.48.

EXAMPLE 286

Preparation of 3-[1-(4-chlorophenylmethyl)-3-(1,1-dimethylethylthio)-5-(1-methylethyl)indol-2-yl]-2,2-dimethylpropionaldehyde oxime-O-2-acetic acid, sodium salt

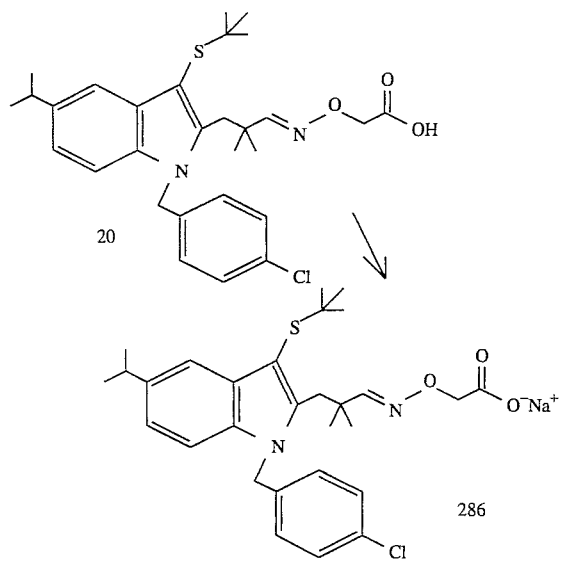

Starting with 20 (1.16 g, 2.19 mmol) and adapting the procedure described in Example 13, 0.51 g of 286 was obtained as a pale pink solid. m.p. 218°–220° C.; $^1$H NMR (300M Hz, DMSO-$d_6$); 1.06 (6H, s), 1.19 (9H, s),1.23 (6H, d, J=6 Hz), 2.95 (1H, septet, J=6 Hz), 3.05 (2H, bs), 4.12 (2H, s), 5.50 (2H, s), 6.90 (2H, d, J=9 Hz), 6.97 (1H, dd, J=1.5 and 9 Hz), 7.25 (1H, d, J=9 Hz), 7.32 (2H, d, J=9 Hz), 7.41 (1H, s), 7.47 (1H, d, J=1.5 Hz); MS (M+H)$^+$=551. Analysis calc'd for $C_{29}H_{36}ClN_2O_3SNa$: C, 63.20; H, 6.58; N, 5.08; Found: C, 63.09; H, 6.59; N, 5.04.

EXAMPLE 287

Preparation of 3-[1-(4-chlorophenylmethyl)-3-(1,1-dimethylethylthio)-5-(1-methylethyl)indol-2-yl]-2,2-dimethylpropionaldehyde oxime-O-2-propionic acid

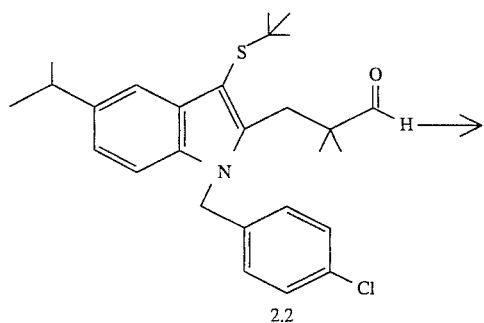

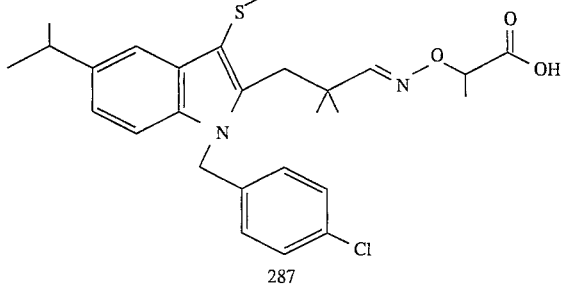

Starting with 2.2 and adapting the procedure described in Example 20, substituting carboxy-1-ethyoxylamine hydrochloride for carboxymethoxylamine hemihydrochloride, 0.20 g of Compound 287 was obtained as a white amorphous solid after purification by chromatography (silica gel, 20/78/2 EtOAc/hexanes/HOAc). m.p. 70°–90° C.; $^1$H NMR (300M Hz, DMSO-$d_6$); 1.07 (6H, d, J=7 Hz), 1.20 (9H, s), 1.22 (6H, d, J=7 Hz), 1.28 (3H, d, J=7 Hz), 2.95 (septet, J=7 Hz), 3.08 (1H, bs), 4.45 (1H, quartet, J=7 Hz), 5.45 (2H, bs), 6.87 (2H, d, J=9 Hz), 6.97 (1H, dd, J=1.5 and 9 Hz), 7.24 (1H, J=9 Hz), 7.33 (2H, J=9 Hz), 7.47 (1H, J=1.5 Hz), 7.50 (1H, s), 12.61 (1H, bs); MS (M+H)$^+$=543 and (M+NH$_4$)$^+$= 560. Analysis calc'd for $C_{30}H_{39}ClN_2O_3S$: C, 66.34; H, 7.24; N, 5.16; Found: C, 66.46; H, 7.39; N, 5.08.

EXAMPLE 288

Preparation of 3-[3-(1,1-dimethylethylthio-5-(quinolin-2-ylmethoxy)-1-(4-chlorophenylmethyl)indol-2-yl]-2,2-dimethylpropionaldehyde oxime-O-2-acetic acid

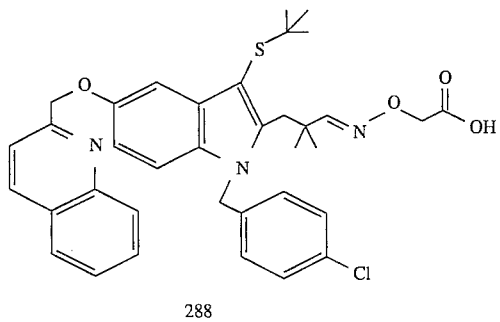

A solution of 4-acetamidophenol (14.28g, 94.4 mmol), 2-(chloromethyl)quinoline monohydrochloride (20.22 g, 94.4 mmol) and freshly powdered $K_2CO_3$ (39.14 g, 283.2 mmol) in DMF (250 mls) for 4 days. It was then poured into 1:1 ice:$H_2O$ (600 mls). The resulting precipitate was collected and washed with water. It was then crystallized in 95% ethanol to afford 25.31 g (91% ) of 4-(quinolin-2-ylmethoxy)acetanilide.

A suspension of 4-(quinolin-2-ylmethoxy)acetanilide (25.29 g, 86.6 mmol) in 95% ethanol (200 mls) containing 10M KOH (25 mls) was heated at reflux for 3 days. It was then cooled to r.t. and the ethanol was stripped off in vacuo. The resulting residue was diluted with water (40 mls) and the precipitate collected and washed well with water. It was then taken up in hot ethylacetate (500 mls) and decolorized with charcoal. The solution was boiled to leave a volume of 200 mls, and hexane was added (200 mls). The solution was allowed to cool to r.t. and the crystals collected to afford 16.63 g (77%) of 4-(quinolin-2-ylmethoxy)aniline.

To a suspension of 4-(quinolin-2-ylmethoxy)aniline (10.62 g, 42.5 mmol) in $H_2O$ (40 mls) was added concentrated HCl (10.63 mls, 127.5 mmol) and the suspension was vigorously stirred to obtain a fine white suspension, then cooled to 0° C.. A solution of sodium nitrite (3.02 g, 43.78 mmol) in $H_2O$ (9 mls) was then added dropwise. Upon completion of addition, the reaction was stirred for I hr at 0° C. to afford the diazonium salt as a clear orange/yellow solution.

To a solution of $Na_2S_2O_4$ (56.20 g of an 85% purity sample, 274.35 mmol) in water (250 mls ), and ether (250 mls) containing NaOH (1.90 mls of a 2N solution, 3.79 mmol) at 0° C., was added the solution of the diazonium salt from above, dropwise and with vigorous stirring. Upon completion of addition, NaOH (75.89 mls of a 2N solution, 151.8 mmol) was added dropwise. The cooling bath was removed and the reaction allowed to warm to r.t. and stirred for 1 hr. The orange solid was then collected, washed well with ether and finally with water. The resulting solid was freeze dried for 18 hrs to afford 9.84 g (87%) of 4 -(quinolin-2-ylmethoxy)phenylhydrazine as a pale orange solid.

To a solution of diisopropylethylamine (7.67 g, 59.36 mmol) in $CH_2Cl_2$ (150 mls) was added 4-(quinolin-2-ylmethoxy)phenylhydrazine (9.83 g, 37.1 mmol). This was followed by the addition of 4-chlorobenzyl chloride (8.96 g, 55.65 mmol), tetrabutylammonium bromide (3.59 g, 11.13 mmol) and an additional 50 mls of $CH_2Cl_2$ and the reaction was stirred for 24 hrs. It was then diluted with $H_2O$ (200 mls) and the layers were separated. The aqueous was extracted with $CH_2Cl_2$ (2×200 mls). The organics were combined, dried with $MgSO_4$ and concentrated. The resulting solid was washed with 9:1 ether:methanol (250 mls) to afford 8.89 g (64%) of 1-(4-chlorophenylmethyl)-1-4-(quinolin-2-ylmethoxy)phenyl)hydrazine as a pale yellow solid.

To a solution of methyl 2,2-dimethyl-4-keto-5-(1,1-dimethylethylthio)pentenoate (5.29 g, 21.5 mmol) in toluene (50 mls) and acetic acid (25 mls) was added sodium acetate (2.03 g, 24.73 mmol) followed by 1-(4 -chlorophenylmethyl)-1-(4-(quinolin-2-ylmethoxy)phenyl)hydrazine (8.88 g, 22.8 mmol) and the reaction was stirred for 5 days in the dark. It was then poured into water (500 mls) and extracted with ethylacetate (3×100 mls). The combined organics were then washed with water (3×100 mls). Solid $NaHCO_3$ (10 g) was added to the organics and the mixture was filtered and finally washed with water (2×100 mls). It was then dried with $MgSO_4$ and concentrated. The resulting residue was chromatographed (silica gel, ether:hexanes, 2:8 to 3:7) to afford methyl 3-[3-(1,1-dimethylethylthio)-5-(quinolin-2-ylmethoxy)-1-(4 -chlorophenylmethyl)indol-2-yl]-2,2-dimethylpropionate.

A solution of methyl 3-[3-(1,1-dimethylethylthio)-5-(quinolin-2 -ylmethoxy)-1-(4-chlorophenylmethyl)indol-2-yl]-2,2-dimethylpropionate (3.48 g, 5.8 mmol) in 1:2:1 THF:methanol:1N LiOH (80 mls) was heated at 80° C. for 3 hrs. It was then cooled to r.t., diluted with water (50 mls) and washed with ether (1×60 mls). The aqueous layer was then acidified to pH5 by the addition of solid citric acid and extracted with ethylacetate (3×60 mls). The organics were combined, dried with $MgSO_4$, decolorized with charcoal and concentrated. Crystallization in ethylacetate/hexanes afforded 3-[3-(1,1-dimethylethylthio)-5 -(quinolin-2-ylmethoxy)-1-(4-chlorophenylmethyl)indol-2-yl]-2,2-methylpropionic acid.

To a solution of 3-[3-(1,1-dimethylethylthio)-5-(quinolin-2-ylmethoxy)-1-( 4-chlorophenylmethyl)indol-2-yl]-2,2-dimethylpropionic acid (2.57 g, 4.4 mmol) in THF (20 mls) was added borane dimethyl sulfide complex (1.06 g, 14.0 mmol) dropwise. Upon completion of addition, the reaction was stirred for 18 hrs. It was then quenched slowly and dropwise with aqueous sat'd $NaHCO_3$ (30 mls). The THF was stripped off in vacuo and the aqueous residue was extracted with ethylacetate (3×50 mls). The organics were combined, dried with $MgSO_4$ and concentrated. The resulting residue was chromatographed (silica gel, ether:hexanes, 1:1) to afford 1.82 g (72%) of 3-[3-(1,1-dimethylethylthio)-5 -(quinolin-2-ylmethoxy)-1-(4-chlorophenylmethyl)indol-2-yl]-2,2-dimethylpropanol as a white foam.

To a solution of oxalyl chloride (461 mg, 3.6 mmol) in $CH_2Cl_2$ (10 mls) at −78° C. was added dimethylsulfoxide (600 mg, 7.68 mmol) dropwise and the resulting mixture was stirred for 5 mins. A solution of 3-[3-(1,1 -dimethylethylthio)-5-(quinolin-2-ylmethoxy)-1-(4-chlorophenylmethyl)indol-2yl] -2,2-dimethylpropanol (1.81 g, 3.2 mmol) in $CH_2Cl_2$ (5 mls) was then added dropwise and the reaction was stirred for 20 mins at −78° C. Triethylamine (1,62 g, 16.0 mmol) was then added dropwise, the cooling bath was withdrawn and the reaction allowed to warm to r.t. It was then diluted with aqueous sat'd $NaHCO_3$ (20 mls) and the layers were separated. The aqueous was extracted with $CH_2Cl_2$ (2×20 mls). The organics were combined, dried with $MgSO_4$ and concentrated. The resulting residue was chromatographed (silica gel, ether:hexanes, 1:1) to afford 1.58 g (86%) of 3-[3-(1,1-dimethylethylthio)-5-(quinolin-2-ylmethoxy)-1-( 4-chlorophenylmethyl)indol-2-yl]-2,2-dimethylpropionaldehyde as a lemon yellow solid.

A solution of 3-[3-(1,1 -dimethylethylthio)-5-(quinolin-2-ylmethoxy)-1-(4 -chlorophenylmethyl)indol-2-yl]-2,2-dimethylpropionaldehyde (1.57 g, 2.7 mmol) and carboxymethoxylamine hemihydrochloride (361 gm, 1.6 mmol)in 1:1 ethanol:pyridine (15 mls) was stirred for 18 hrs. The reaction was then concentrated in vacuo. The resulting residue was taken up in water (20 mls) and extracted with ethylacetate (3×20 mls). The organics were combined, dried with $MgSO_4$ and concentrated. The sample was chromatographed (silica gel, ether:hexanes containing 2% HOAc, 1:1) to afford 3-[3-(1,1-dimethylethylthio )-5 -(quinolin-2-ylmethoxy)-1-(4-chlorophenylmethyl)indol-2-yl]-2,2-dimethylpropionaldehyde oxime-O-2-acetic acid as a foam. $^1$H NMR (300 MHz, DMSO-$d_6$): 0.98m (s, 9H), 1.05 (s, 6H), 3.04 (bs, 2H), 4.42 (s, 2H), 5.39 (s, 2H), 5.45 (s, 2H), 6.85 (m, 3H), 7.13 (d, 1H, J=2.5 Hz), 7.30 (m, 3H), 7.53 (s, 1H), 7.58–7.68 (m, 2H), 7.79 (m, 1H), 7.97 (m, 1H), 8.05 (d, 1H, J=8.5 Hz), 8.37 (d, 1H, J=8.5 Hz); MS (M+H)$^+$=644; Analysis calc'd for $C_{36}H_{38}ClN_3O_4S\cdot\frac{1}{2}H_2O$: C, 66.19, H, 6.02, N, 6.43; Found: C, 66.30, H, 6.12, N, 6.22.

EXAMPLE 289

Preparation of Sodium 3-[1-(4-chlorophenylmethyl)-3-(1,1-imethylethylthio)-5-(1-methylethyl) indol-2-yl]-2,2-dimethylpropionaldehyde oxime-O-2-propionate The desired product 289 is prepared from 287 according to the procedure of Example 12.

EXAMPLE 290

Preparation of Sodium
3-[3-(1,1-dimethylethylthio)-5-(quinolin-2-ylmethoxy)-1
-(4-chlorophenyl methyl)
indol-2-yl]-2,2-dimethylpropionaldehyde
oxime-O-2-acetate The desired product 290 is prepared from 288 according to the procedure of Example 12.

EXAMPLE 291

Preparation of 3-[1-(4-chlorophenylmethyl)-3-(1,1-dimethylethylthio)-5
-(methoxy)indol-2-yl]-2,2-dimethylpropionaldehyde
oxime-O-2-propionic acid

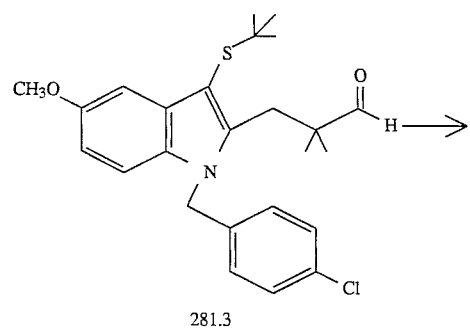

281.3

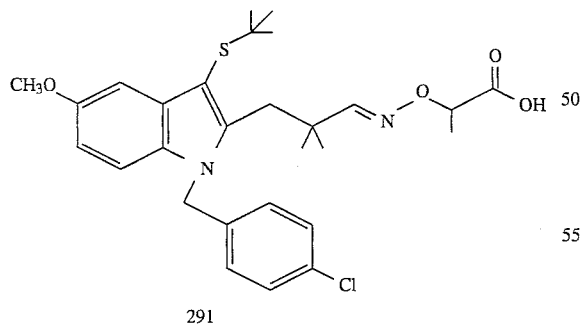

291

The desired product 291 is prepared from 281.3 by the procedure of Example 287.

EXAMPLE 292

Preparation of
3-[1-(4-fluorophenylmethyl)-3-(1,1-dimethylethylthio)-5
-(1-methylethyl)
indol-2-yl]-2,2-dimethylpropionaldehyde oxime-O-2
-propionic acid

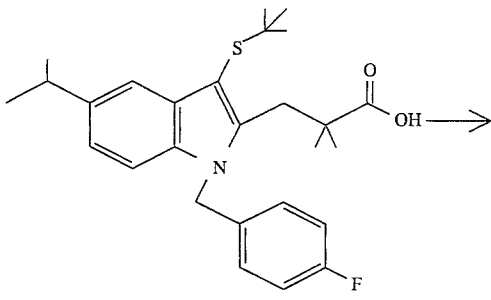

285.2

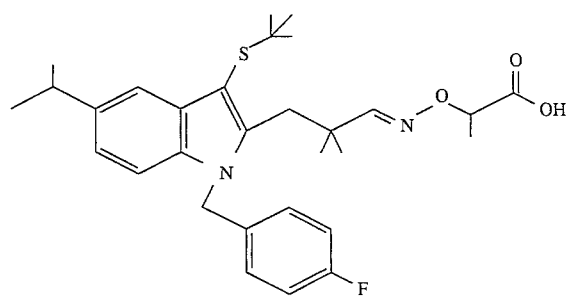

292

The desired product 292 is prepared from 285.2 by the procedure of Example 285 substituting carboxy-1-ethoxylamine hydrochloride for carboxymethoxylamine hemihydrochloride.

EXAMPLE 293

Preparation of
3-[3-(1,1-dimethylethylthio)-5-(quinolin-2-ylmethoxy)-
1-(4-chlorophenylmethyl)
indol-2-yl]-2,2-dimethylpropionaldehyde oxime-O-2
-propionic acid

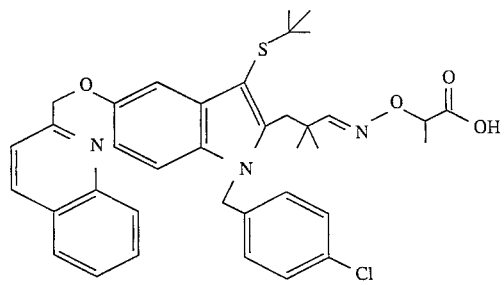

The desired product 293 is prepared by the procedure of Example 288 substituting carboxy-1-ethoxylamine hydrochloride for carboxymethoxylamine hemihydrochloride.

Additional examples of the present invention are prepared by the procedure of Example 288 utilizing the requisite hydrazine and carboxyalkoxyamine as indicated in Table 13.

TABLE 13

| Example | Hydrazine | Carboxyalkoxyamine | Product |
|---|---|---|---|
| 294 | | | |
| 295 | | | |
| 296 | | | |

TABLE 13-continued

| Example | Hydrazine | Carboxyalkoxyamine | Product |
|---|---|---|---|
| 297 | | | |
| 298 | | | |
| 299 | | | |

TABLE 13-continued

TABLE 13-continued

| Example | Hydrazine | Carboxyalkoxyamine | Product |
|---|---|---|---|
| 303 | | | |
| 304 | | | |

The foregoing examples are provided to enable one skilled in the art to practice the present invention. These examples are merely illustrative, however, and should not be read as limiting the scope of the invention as it is claimed in the appended claims.

We claim:

1. A compound of Formula I:

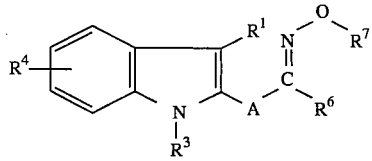

or a pharmaceutically acceptable salt thereof, wherein

A is selected from the group consisting of
straight or branched divalent alkylene of one to twelve carbon atoms,
straight or branched divalent alkenylene of two to twelve carbon atoms, and
divalent cycloalkylene of three to eight carbon atoms;

$R^1$ is alkylthio of one to six carbon atoms;

$R^6$ is selected from the group consisting of hydrogen and alkyl of one to six carbon atoms;

$R^7$ is selected from the group consisting of
(carboxyl)alkyl in which the alkyl portion is of one to six carbon atoms,
(alkoxycarbonyl)alkyl in which the alkoxycarbonyl portion is of two to six carbon atoms and the alkyl portion is of one to six carbon atoms,
(aminocarbonyl)alkyl in which the alkyl portion is of one to six carbon atoms,
((alkylamino)carbonyl)alkyl in which each alkyl portion independently is of one to six carbon atoms, and
((dialkylamino)carbonyl)alkyl in which each alkyl portion independently is of one to six carbon atoms;

$R^3$ is phenylalkyl in which the alkyl portion is of one to six carbon atoms;

$R^4$ is 2-, 3- or 6-quinolylmethoxy, optionally substituted with
alkyl of one to six carbon atoms,
haloalkyl of one to six carbon atoms,
alkoxy of one to twelve carbon atoms,
halogen, or
hydroxy.

2. A compound as defined by claim 1 selected from the group consisting of

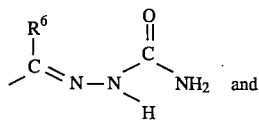

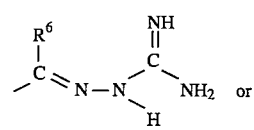

a pharmaceutically acceptable salt thereof, wherein $R^6$ is as defined therein.

3. A compound as defined by claim 1 selected from the group consisting of 3-(3-1,1-dimethylethylthio)-5-(quinolin-2-ylmethoxy-1-(4 -chlorophenylmethyl)-indol-2-yl)-2,2-dimethyl-propionaldehyde oxime-O-2 acetic acid;

3-(3-(1,1-dimethylethylthio)-5-(quinolin-2-ylmethoxy)-1-(4 -chloro-phenylmethyl) indol-2-yl)-2,2-dimethyl-propionaldehyde oxime-O-2 -(3-methyl)butyric acid;

3-(3-(1,1-dimethylethylthio)-5-(6,7-dichloroquinolin-2-ylmethoxy)- 1-(4-chlorophenylmethyl) indol-2-yl)-2,2-dimethylpropionaldehyde oxime-O- 2-acetic acid; and 3-(3-(1,1-dimethylethylthio)-5-(6-fluoroquinolin-2-ylmethoxy)-1-(4chlorophenylmethyl) indol-2-yl)-2,2-dimethylpropionaldehyde oxime-O- 2-propionic acid; or a pharmaceutically acceptable salt or ester thereof.

4. A pharmaceutical composition comprising a therapeutically effective amount of a compound as defined by claim 1 in combination with a pharmaceutically acceptable carrier.

5. A method of inhibiting lipoxygenase enzymes in a host mammal in need of such treatment comprising administering a therapeutically effective amount of a compound as defined by claim 1.

* * * * *

UNITED STATES PATENT AND TRADEMARK OFFICE
CERTIFICATE OF CORRECTION

PATENT NO. : 5,459,150  
DATED : October 17, 1995  
INVENTOR(S) : Dee W. Brooks, *et al.*

Page 1 of 7

It is certified that error appears in the above-indentified patent and that said Letters Patent is hereby corrected as shown below:

Column 1, Line 34, change "Arachidonie" to --Arachidonic--.

Column 1, Line 42, change "hydroxyeicosatetraenoic" to -- 5-hydroxyeicosatetraenoic--.

Column 1, Line 48, change "proteolyfic" to --proteolytic--

Column 1, Line 49, change "LTF$_4$" to --LTE$_4$--.

Column 2, Line 10, change "ethyt" to --ethyl--.

Column 2, Line 14, change "carboxarnides" to --carboxamides--.

Column 2, Line 24, change "antiphlogisfic" to --antiphlogistic--.

Column 2, Line 38, change "carboxarnido" to --carboxamido--.

Column 2, Line 62, change "divaient" to --divalent--.

Column 3, Line 19, change "phenylaikylthio" to --phenylalkylthio--.

UNITED STATES PATENT AND TRADEMARK OFFICE
CERTIFICATE OF CORRECTION

PATENT NO. : 5,459,150
DATED : October 17, 1995
INVENTOR(S) : Dee W. Brooks, *et al.*

It is certified that error appears in the above-indentified patent and that said Letters Patent is hereby corrected as shown below:

Column 4, Line 48, change "a/koxycarbonyl" to --alkoxycarbonyl--.

Column 6, Line 24, change "hydroxy phenyl" to --hydroxy; phenyl--.

Column 6, Line 37, change "-$(CH_2)_nN(OH)C(O)NRSR^6$" to -- -$(CH_2)_nN(OH)C(O)NR^5R^6$ --.

Column 6, Line 38, change "-$(CH_2)_nN(RS)C(O)N(OM)R^6$" to-- -$(CH_2)_nN(R^5)C(O)N(OM)R^6$ --.

Column 6, Line 39, change "-$(CH_2)_nN(OH)C(O)NRSR^6$" to -- -$(CH_2)_nN(OH)C(O)NR^5R^6$ --.

Column 6, Line 50, change "ting" to --ring--.

Column 6, Line 63, change "ting" to --ring--.

Column 7, Line 37, change "ting" to --ring--.

Column 7, Line 40, change "-pyrimidyl" to --pyrimidyl--.

Column 10, Line 13, change "-$(CH_2)_nN(OH)C(O)NRSR^6$" to -- -$(CH_2)_nN(OH)C(O)NR^5R^6$ --.

UNITED STATES PATENT AND TRADEMARK OFFICE
CERTIFICATE OF CORRECTION

PATENT NO. : 5,459,150            Page 3 of 7
DATED : October 17, 1995
INVENTOR(S) : Dee W. Brooks, *et al.*

It is certified that error appears in the above-indentified patent and that said Letters Patent is hereby corrected as shown below:

Column 10, Line 41, change "2,2dimethylpropionylamino" to
-- 2,2-dimethylpropionylamino --.

Column 10, Line 65, change "l" to
-- 1 --.

Column 12, Line 45, change "titrate" to
--citrate--.

Column 13, Line 9, change "mutes" to
--routes--.

Column 13, Line 14, change "85" to
--1985--.

Column 14, Line 27, change "rain" to
--min--.

Column 15, Line 14, change "garage" to
--gavage--.

Column 17, Line 24, change "bentonitc" to
--bentonite--.

Column 18, Line 49, change "hour:," to
--hour;--.

UNITED STATES PATENT AND TRADEMARK OFFICE
CERTIFICATE OF CORRECTION

PATENT NO. : 5,459,150
DATED : October 17, 1995
INVENTOR(S) : Dee W. Brooks, et al.

It is certified that error appears in the above-indentified patent and that said Letters Patent is hereby corrected as shown below:

Column 18, Line 62, change "(1H, s)" to --6.35 (1H, s)--.

Column 18, Line 64, change ".[=8.4" to --J=8.4--.

Column 18, Line 64, change "(1H, d, 9Hz)" to --(1H, d, J=9Hz)--.

Column 20, Line 23, change "retool)." to --mmol).--.

Column 26, Line 60, change "rag" to --mg--.

Column 27, Line 64, change "(2H, br t, Hz)" to --(2H, br t, J=6.0 Hz)--.

Column 29, Line 59, change "$C_{32}H_{44}ClN_3O_{35}$" to --$C_{32}H_{44}ClN_3O_3S$--.

Column 30, Line 51, change "J-6.9" to --J=6.9--.

Column 30, Line 54, change "J-6.25" to --J=6.25--.

UNITED STATES PATENT AND TRADEMARK OFFICE
CERTIFICATE OF CORRECTION

PATENT NO. : 5,459,150
DATED : October 17, 1995
INVENTOR(S) : Dee W. Brooks, et al.

It is certified that error appears in the above-indentified patent and that said Letters Patent is hereby corrected as shown below:

Column 32, Line 53, change "$C_{30}H_{38}ClN_3OS$" to

--$C_{30}H_{38}ClN_3O_5$--.

Column 33, Line 8, change "propyl]-" to

-- propyl]-5- --.

Column 34, Line 43, change "MeOH/CH$_2$C$_2$" to

--MeOH/CH$_2$Cl$_2$--.

Column 34, Line 49, change "J=8.2 Hz" to

--J=8.25 Hz--.

Column 34, Line 53, change "$C_{30}H_{39}ClN_3o_3$" to

--$C_{30}H_{39}ClN_3O_3$--.

Column 37, Line 5, change "ice/cone." to

--ice/conc.--.

Column 38, Line 9, change "rain" to

--min--.

Column 38, Line 15, change "3.21 (m, 1 H)" to

--3.66 (dd, 1H, J=5 Hz, J=14 Hz), 5.58 (br s, 2H), 6.30 (br s, 2H), 6.98 (m, 3H),--.

Column 40, Line 44, change "indol-yl" to

-- indol-2-yl --.

Column 42, Line 49, change "3-(4-chlorophenylmethyl)" to

-- 3-[1-(4-chlorophenylmethyl)--.

UNITED STATES PATENT AND TRADEMARK OFFICE
CERTIFICATE OF CORRECTION

PATENT NO. : 5,459,150  
DATED : October 17, 1995  
INVENTOR(S) : Dee W. Brooks, et al.

It is certified that error appears in the above-indentified patent and that said Letters Patent is hereby corrected as shown below:

Column 44, Line 21, change "EtOH-EtOAc" to --EtOH/EtOAc--.

Column 44, Line 27, change "3.3/96.5" to --3.5/96.5--.

Column 44, Line 34, change "J=8.23 Hz)" to --J=8.25 Hz)--.

Column 45, Line 24, change "10-%" to --10%--.

Column 47, Line 49, change "Et20" to --$Et_2O$--.

Column 52, Line 30, change "convened" to --converted--.

Column 59, Line 3, change "280.1" to --280--.

Column 59, Line 9, change "$C_{26}H37N_3OS_2$" to --$C_{26}H_{37}N_3OS_2$--.

Column 61, Line 45, change "stiffing" to --stirring--.

UNITED STATES PATENT AND TRADEMARK OFFICE
CERTIFICATE OF CORRECTION

PATENT NO. : 5,459,150
DATED : October 17, 1995
INVENTOR(S) : Dee W. Brooks, et al.

It is certified that error appears in the above-indentified patent and that said Letters Patent is hereby corrected as shown below:

Column 62, Line 1, change "$C_{30}H_{39}ClN_2O_3S$" to --$C_{30}H_{39}ClN_2O_3S$--.

Column 63, Line 25, change "2.88-3.12 (6H, m)" to --2.88-3.12 (5H, m)--.

Column 63, Line 29, change "$C_{30}H_{41}ClN_4O_2S(0.25\ H_2O)$" to --$C_{30}H_{41}ClN_4O_2S(0.25\ H_2O)$--.

Column 64, Line 46, change "$C_{27}H_{34}FNO_2S(0.25\ H_2O)$" to --$C_{27}H_{34}FNO_2S(0.25\ H_2O)$--.

Column 64, Line 59, change "$C_{29}H_{37}FN_2O_3S$" to --$C_{29}H_{37}FN_2O_3S$--.

Column 65 Line 41, change "$C_{29}H_{36}ClN_2O_3SNa$" to --$C_{29}H_{36}ClN_2O_3SNa$--.

Signed and Sealed this

Twenty-fourth Day of December, 1996

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,459,150
DATED : October 17, 1995
INVENTOR(S) : D.W. Brooks, et al.

It is certified that error appears in the above-indentified patent and that said Letters Patent is hereby corrected as shown below:

Column 80, line 17, change "salt thereof" to --salt, ester or amide thereof--.

Column 80, line 36, delete the word "ester".

Signed and Sealed this

Eleventh Day of February, 1997

Attest:

BRUCE LEHMAN

*Attesting Officer*   *Commissioner of Patents and Trademarks*